US011273177B2

(12) United States Patent
Chapman et al.

(10) Patent No.: US 11,273,177 B2
(45) Date of Patent: Mar. 15, 2022

(54) TUMOR INFILTRATING CELLS ENGINEERED TO EXPRESS A PRO-INFLAMMATORY POLYPEPTIDE

(71) Applicant: Berkeley Lights, Inc., Emeryville, CA (US)

(72) Inventors: Kevin T Chapman, Emeryville, CA (US); Xiaohua Wang, Pomona, NY (US); Xiao Guan Radstrom, San Rafael, CA (US); Yelena Bronevetsky, Alameda, CA (US); Guido K Stadler, San Francisco, CA (US); Gregory G Lavieu, Vitry sur Seine (FR); Annamaria Mocciaro, San Francisco, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 870 days.

(21) Appl. No.: 15/488,139

(22) Filed: Apr. 14, 2017

(65) Prior Publication Data

US 2017/0224734 A1 Aug. 10, 2017

Related U.S. Application Data

(63) Continuation of application No. PCT/US2016/069468, filed on Dec. 30, 2016.

(60) Provisional application No. 62/274,059, filed on Dec. 31, 2015.

(51) Int. Cl.
| | |
|---|---|
| *A61K 35/17* | (2015.01) |
| *C07K 14/55* | (2006.01) |
| *C12N 9/24* | (2006.01) |
| *C07K 16/28* | (2006.01) |
| *B01L 3/00* | (2006.01) |
| *C07K 14/195* | (2006.01) |
| *C12N 5/0783* | (2010.01) |
| *A61K 31/65* | (2006.01) |
| *C12N 5/00* | (2006.01) |
| *C12N 5/0781* | (2010.01) |
| *C07K 14/47* | (2006.01) |
| *C07K 14/52* | (2006.01) |
| *A61K 39/00* | (2006.01) |

(52) U.S. Cl.
CPC ............. *A61K 35/17* (2013.01); *A61K 31/65* (2013.01); *A61K 39/0011* (2013.01); *B01L 3/50273* (2013.01); *B01L 3/502761* (2013.01); *C07K 14/195* (2013.01); *C07K 14/4748* (2013.01); *C07K 14/52* (2013.01); *C07K 14/55* (2013.01); *C07K 16/2818* (2013.01); *C12N 5/00* (2013.01); *C12N 5/0635* (2013.01); *C12N 5/0636* (2013.01); *C12N 5/0637* (2013.01); *C12N 5/0638* (2013.01); *C12N 9/2402* (2013.01); *C12Y 302/01166* (2013.01); *B01L 2300/0861* (2013.01); *B01L 2300/0896* (2013.01); *B01L 2400/0424* (2013.01); *C07K 2317/14* (2013.01); *C07K 2319/00* (2013.01); *C12N 2501/04* (2013.01); *C12N 2510/00* (2013.01)

(58) Field of Classification Search
None
See application file for complete search history.

(56) References Cited

U.S. PATENT DOCUMENTS

| | | |
|---|---|---|
| 6,294,063 B1 | 9/2001 | Becker et al. |
| 6,767,535 B1 | 7/2004 | Rollins et al. |
| 6,942,776 B2 | 9/2005 | Medoro |
| 7,090,759 B1 | 8/2006 | Seul |
| 7,312,085 B2 | 12/2007 | Chou et al. |
| 7,442,339 B2 | 10/2008 | Sundararajan et al. |
| 8,921,041 B2 | 12/2014 | Wang et al. |
| 10,239,058 B2 | 3/2019 | Lavieu et al. |
| 2003/0008364 A1 | 1/2003 | Wang et al. |
| 2004/0072278 A1 | 4/2004 | Chou et al. |
| 2004/0191789 A1 | 9/2004 | Manaresi et al. |
| 2004/0197905 A1 | 10/2004 | Hafeman |
| 2005/0112548 A1 | 5/2005 | Segawa et al. |
| 2005/0129581 A1 | 6/2005 | McBride et al. |
| 2005/0175981 A1 | 8/2005 | Voldman et al. |
| 2005/0221333 A1 | 10/2005 | Sundararajan et al. |
| 2006/0091015 A1 | 5/2006 | Lau |

(Continued)

FOREIGN PATENT DOCUMENTS

| | | |
|---|---|---|
| CN | 101772580 A | 7/2010 |
| EP | 0421380 B1 | 12/1995 |

(Continued)

OTHER PUBLICATIONS

Gilham et al., Trends in Molecular Medicine, 2012(18)377-384 (Year: 2012).*

(Continued)

*Primary Examiner* — James D Schultz

(74) *Attorney, Agent, or Firm* — McNeill Baur PLLC

(57) ABSTRACT

The present disclosure provides methods of preparing tumor infiltrating cells engineered to express a pro-inflammatory polypeptide. The pro-inflammatory polypeptide is expressed from the tumor infiltrating cell to counter a generally immunosuppressive state in and around tumors resulting from an imbalance between the number and activation state of immune effector cells versus those of suppressor cells. Delivering the proinflammatory polypeptide via expression from the TICs, as distinct from systemic administration, reduces side effects from increased inflammation at sides remote from a tumor to be treated.

9 Claims, 14 Drawing Sheets

(56) References Cited

U.S. PATENT DOCUMENTS

| | | |
|---|---|---|
| 2006/0154361 A1 | 7/2006 | Wikswo et al. |
| 2007/0095669 A1 | 5/2007 | Lau et al. |
| 2007/0183934 A1 | 8/2007 | Diercks et al. |
| 2007/0242105 A1 | 10/2007 | Srinivasan et al. |
| 2008/0302732 A1 | 12/2008 | Soh et al. |
| 2009/0023608 A1 | 1/2009 | Hung et al. |
| 2009/0170186 A1 | 7/2009 | Wu et al. |
| 2010/0003666 A1 | 1/2010 | Lee et al. |
| 2010/0101960 A1 | 4/2010 | Ohta et al. |
| 2010/0273681 A1 | 10/2010 | Cerrina et al. |
| 2010/0330056 A1* | 12/2010 | Yee ........................ A61K 31/41 424/93.71 |
| 2011/0053151 A1 | 3/2011 | Hansen et al. |
| 2011/0117634 A1 | 5/2011 | Halamish et al. |
| 2011/0143964 A1 | 6/2011 | Zhou et al. |
| 2011/0217274 A1 | 9/2011 | Reid |
| 2011/0262906 A1 | 10/2011 | Dimov et al. |
| 2012/0009671 A1 | 1/2012 | Hansen et al. |
| 2012/0015347 A1 | 1/2012 | Singhal et al. |
| 2012/0015382 A1 | 1/2012 | Weitz et al. |
| 2012/0118740 A1 | 5/2012 | Garcia et al. |
| 2012/0156675 A1 | 6/2012 | Lueerssen et al. |
| 2012/0208266 A1 | 8/2012 | Bookbinder et al. |
| 2012/0325665 A1 | 12/2012 | Chiou et al. |
| 2013/0071403 A1 | 3/2013 | Rolland et al. |
| 2013/0118905 A1 | 5/2013 | Morimoto et al. |
| 2013/0171628 A1 | 7/2013 | Carlo et al. |
| 2013/0190212 A1 | 7/2013 | Handique et al. |
| 2013/0204076 A1 | 8/2013 | Han et al. |
| 2013/0261021 A1 | 10/2013 | Bocchi et al. |
| 2013/0288065 A1 | 10/2013 | Chen et al. |
| 2014/0017791 A1 | 1/2014 | Chapman et al. |
| 2014/0116881 A1 | 5/2014 | Chapman et al. |
| 2014/0124370 A1 | 5/2014 | Short et al. |
| 2014/0186295 A1 | 7/2014 | Kupper et al. |
| 2015/0018226 A1 | 1/2015 | Hansen et al. |
| 2015/0151298 A1 | 6/2015 | Hobbs et al. |
| 2015/0151307 A1 | 6/2015 | Breinlinger et al. |
| 2015/0165436 A1 | 6/2015 | Chapman et al. |
| 2015/0166326 A1 | 6/2015 | Chapman et al. |
| 2015/0306599 A1 | 10/2015 | Khandros et al. |
| 2016/0158757 A1 | 6/2016 | Breinlinger et al. |
| 2016/0171686 A1 | 6/2016 | Du et al. |
| 2016/0184821 A1 | 6/2016 | Hobbs et al. |
| 2016/0193604 A1 | 7/2016 | McFarland et al. |
| 2016/0199837 A1 | 7/2016 | Breinlinger et al. |
| 2016/0252495 A1 | 9/2016 | Ricicova et al. |
| 2016/0312165 A1 | 10/2016 | Lowe et al. |
| 2018/0147576 A1 | 5/2018 | Lavieu et al. |
| 2018/0298318 A1 | 10/2018 | Kurz et al. |
| 2019/0217297 A1 | 7/2019 | Lavieu et al. |
| 2019/0240665 A1 | 8/2019 | Lionberger et al. |
| 2020/0048606 A1 | 2/2020 | Marson et al. |

FOREIGN PATENT DOCUMENTS

| | | | |
|---|---|---|---|
| EP | 0981408 B1 | | 4/2004 |
| KR | 20100008222 A | | 1/2010 |
| WO | 2002088702 A2 | | 11/2002 |
| WO | 2004040001 A2 | | 5/2004 |
| WO | 2004089810 A2 | | 10/2004 |
| WO | 2005100541 A2 | | 10/2005 |
| WO | 2007008609 A2 | | 1/2007 |
| WO | 2007024701 A2 | | 3/2007 |
| WO | 2008119066 A1 | | 10/2008 |
| WO | 2008150814 A2 | | 12/2008 |
| WO | 2009130694 A2 | | 10/2009 |
| WO | 2010040851 A2 | | 4/2010 |
| WO | 2010115167 A2 | | 10/2010 |
| WO | 2010147078 A1 | | 12/2010 |
| WO | 2011160430 A1 | | 12/2011 |
| WO | 2012024658 A2 | | 2/2012 |
| WO | 2012037030 A2 | | 3/2012 |
| WO | 2012072823 A1 | | 6/2012 |
| WO | 2012162779 A1 | | 12/2012 |
| WO | 2013019491 A1 | | 2/2013 |
| WO | 2013130714 A1 | | 9/2013 |
| WO | WO 2014/138315 | * | 9/2014 |
| WO | 2015039100 A1 | | 3/2015 |
| WO | 2016100977 A1 | | 6/2016 |
| WO | 2017123978 A1 | | 7/2017 |

OTHER PUBLICATIONS

Zeng et al., J Exp Med (2005) 201 (1): 139-148 (Year: 2005).*
Bachleitner-Hoffmann et al., Stimulation of Autologous Antitumor T-Cell Responses Against Medullary Thyroid Carcinoma Using Tumor Lysate-Pulsed Dendritic Cells, J. Clin. Endo. & Metabl. 87(3): 1098-1104 (2002).
Chen et al., Microfluidic approaches for cancer cell detection, characterization, and separation, Lab on a Chip 12:1753 (2012).
Chiou et al., Massively parallel manipulation of single cells and microparticles using optical images, Nature 436:370-73 (2005).
Chung et al., Imaging single-cell signaling dynamics with a deterministic high-density single-cell trap array, Anal. Chem.83(18):7044-7052 (2011).
Collarini et al., Potent High-Affinity Antibodies for Treatment and Prophylaxis of Respiratory Synctial Virus Derived from B Cells of Infected Patients, J. Immunol., 183: 6338-6345 (2009).
Curran et al., Chimeric antigen receptors for T cell immunotherapy: current understanding and future directions. J Gene Med. 14:405-415 (2012).
Germain et al., Tertiary lymphoid structure-associated B cells are key players in anti-tumor immunity, Frontiers in Immunology, 6: Article 67, 1-14 (2015).
Goc et al., Characteristics of tertiary lymphoid structures in primary cancers. OncoImmunology. 2(12):e26836 (Dec. 2013).
He et al., In vitro generation of cytotoxic T lymphocyte response using dendritic cell immunotherapy in osteosarcoma, Oncology Letters 12: 1101-1106 (2016).
International Search Report and Written Opinion for PCT Application Serial No. PCT/US2016/069468 dated Mar. 17, 2017; 9 pages.
Maheswaran et al., Ex Vivo Culture of CTCs: An Emerging Resource to Guide Cancer Therapy, Cancer Research 75(12) (2015).
Martucci et al., "Nanoparticle-based strategy for personalized B-cell lymphoma therapy", International Journal of Nanomedicine, 11:6089-6101 (2016).
Nevill et al., Integrated microfluidic cell culture and lysis on a chip, Lab on A Chip 7:1689-95 (2007).
Nishio et al. Armed Oncolytic Virus Enhances Immune Functions of Chimeric Antigen Receptor—Modified T Cells in Solid Tumors. Cancer Res. 74(18):5195-205 (2014).
Parker et al., gentleMACS™ Dissociation of melanoma tumors for the generation of tumor-infiltrating lymphocyte cultures foradoptive cell therapy. MACS: Milteyi Biotec. (2011).
Pule et al., A Chimeric T Cell Antigen Receptor That Augments Cytokine Release and Supports Clonal Expansion of Primary Human T Cells. Molecular Therapeutics. 12(5):933-941 (2005).
Schena et al., Dependence of Immunoglobin Class Switch Recombinatino in B Cells on Vesicular Release of ATP and CD73 Ectonucleotidase Activity, Cell Reports, 3:1824-1831 (2013).
Schumacher et al., Neoantigens in cancer immunotherapy, Science 348:69-74 (2015).
Smith et al., Sorting Out Cell Sorting: Flow Cytometry, Magnetic Beads or Microchips?, downloaded from http:// www.biocompare.com/Editorial- Articles/126327- Cell-Sorting (2013).
Topfer et al., DAP12-Based Activating Chimeric Antigen Receptor for NK Cell Tumor Immunotherapy, J. Immunology 194:3201-3212 (2015).
Valley et al., Optoelectronic Tweezers as a Tool for Parallel Single-Cell Manipulation and Stimulation, IEEE Transactions on Biomedical Circuits and Systems 3(6):424-30 (2009).
Van Dongen et al., EuroFlow antibody panels for standarized n-dimensional flow cytometric immunophenotyping of normal, reactive and malignant leukocytes, Handout at 14th EHA Congress, Berlin, DE, 18 pages (Jun. 4, 2009).

(56) References Cited

OTHER PUBLICATIONS

Vera, et al., T lymphocytes redirected against the light chain of human immunoglobulin efficiently kill mature B lymphocyte-derived malignant cells, Blood 108:3890-3897 (2006).
Watkins, et al., Video Article: Isolation of Immune Cells from Primary Tumors. Journal of Visualized Experiments. vol. 64:e3952, www.jove.com/video/3952/ (2012).
Wang et al., Manufacture of tumor- and virus-specific T lymphocytes for adoptive cell therapies, Cancer Gene Ther. 22(2):85-94 (2015).
Chiou, "Massively parallel optical manipulation of cells, micro- and nano-particles on optoelectronic devices," Dissertation, University of California at Berkeley, 2005 (147 pages).
Cho et al., Targeted genome engineering in human cells with the Cas9 RNA-guided endonuclease, Nautre Biotechnology, vol. 31, No. 3, Mar. 2013, pp. 230-232. (Year: 2013).
Chung et al., "DNA-Tethered Membranes Formed by Giant Vesicle Rupture," Journal of Structural Biology, 2009, 168:190-199.
Cong et al., "Multiplex Genome Engineering Using CRISPR/Cas Systems," Science, 2013, 339:819-23.
Di Carlo et al., "Dynamic Single Cell Analysis for Quantitative Biology," Analytical Chemistry, 2006, 7918-7925.
Gel et al., "Microorifice-Based High-Yield Cell Fusion on Microfluidic Chip: Electrofusion of Selected Pairs and Fusant Viability," IEEE Transactions on Nanobioscience, 2009, 8(4):300-305.
Han et al., "CRISPR-Cas9 Delivery to Hard-to-Transfect Cells via Membrane Deformation," Sci. Adv., 2015, 1(7):1-8.
He, et al., "Knock-in of Large Reporter Genes in Human Cells via CRISPR/Cas9-Induced Homology-Dependent and Independent DNA Repair," Nucleic Acids Research, 2016, 44(9):e85.
Hsu et al., "Sorting of Differentiated Neurons using Phototransistor-Based Optoelectronic Tweezers for Cell Replacement Therapy of Neurodegenerative Diseases," IEEE Conference on Transducers, 2009, 4 pages.
Hu et al., "A High-Throughput Dielectrophoresis-Based Cell Electrofusion Microfluidic Device," Electrophoresis, 2011, 32:2488-2495.
Hultquist et al., "A Cas9 Ribonucleoprotein Platform for Functional Genetic Studies of HIV-Host Interactions in Primary Human T Cells," Cell Reports, 2016, 17(5):1438-52.
Hung et al., "Continuous Perfusion Microfluidic Cell Culture Array for High-Throughput Cell-Based Assays," Biotech and Bioengineering, 2004, 89(1):1-8.
International Search Report and Written Opinion for PCT/US2017/069084, dated May 4, 2018, 72 pages.
International Search Report and Written Opinion for PCT/US2017/022518, dated Aug. 7, 2017, 19 pages.
Jinek et al., "RNA-Programmed Genome Editing in Human Cells," eLife, 2013, 2:e00471.
Liang et al., "Rapid and Highly Efficient Mammalian Cell Engineering via Cas9 Protein Transfection," J. Biotechnol., 2015, 208:44-53.
Lin et al., "An Optically Induced Cell Lysis Device Using Dielectrophoresis," Applied Physics Letters, 2009, 94:033901.
Lowe, Jr. et al., "Deposition of Dense Siloxane Monolayers from Water and Trimethoxyorganosilane Vapor," Langmuir, 2011, 27:9928-9935.
Lowe, Jr., "Controlled Vapor Deposition of Azide-Terminated Siloxane Monolayers: A Platform for Tailoring Oxide Surfaces," Dissertation, Stanford University, Aug. 2011, 152 pages.
Mali et al., "RNA-Guided Human Genome Engineering via Cas9," Science, 2013, 339:823-26.
Mocciaro, A. et al., Light-Activated Cell Identification and Sorting (LACIS): A New Method to Identify and Select Edited Clones on a Microfluidic Device. BioRxiv. Oct. 17, 2017; pp. 1-20.

Peterson et al., "Long-Term Multilineage Engraftment of Autologous Genome-Edited Hematopoietic Stem Cells in Nonhuman Primates," Blood, 2016,127(20):2416-26.
Poirot et al., "Multiplex Genome Edited T-Cell Manufacturing Platform for "off-the-shelf" Adoptive T-Cell Immunotherapies," Cancer Research, 2015, 75(18):3853-64.
Schumann et al., "Generation of Knock-In Primary Human T Cells using Cas9 Ribonucleoproteins," PNAS, 2015, 112(33):10437-42.
Somaweera et al., "Generation of a Chemical Gradient Across an Array of 256 Cell Cultures in a Single Chip," Analyst, 2013, 138(19):5566-5571.
Wickham et al., "Targeted Adenovirus-Mediated Gene Delivery to T Cells via CD3," J Virology, 1997, 71(10):7663-69.
Yi et al., "Microfluidics Technology for Manipulation and Analysis of Biological Cells," Analytica Chimica Acta, 2006, 560:1-23.
File History of U.S. Appl. No. 15/802,174, filed Nov. 2, 2017, by Gregory G. Lavieu, Annamaria Mocciaro, Xiao Guan Radsliom, Jason M. McEwen, Magali Soumillon, J, Tanner Nevill, Volker L.S. Kurz, Patricia A. Dyck,and Ravi K. Ramenani.
File History of U.S. Appl. No. 16/259,538, filed Jan. 28, 2019, by Gregory G. Lavieu, Annamaria Mocciaro, Xiao Guan Radstrom, Jason M. McEwen, Magali Soumillon, J, Tanner Nevill, Volker L.S. Kurz, Patricia A. Dyck,and Ravi K. Ramenani.
File History of U.S. Appl. No. 16/455,118, filed Jun. 27, 2019, by Alexander Marson, Gregory G. Lavieu, Annamaria Mocciaro, Theodore L. Roth, Magali Soumillon, and Hayley M. Bennett.
Feldman et al., "Adoptive Cell Therapy—Tumor-Infiltrating Lymphocytes, T-Cell Receptors, and Chimeric Antigen Receptors," Semin. Oncol., 2015, 42(4):626-639.
Levi et al., "Characterization of tumor infiltrating Natural Killer cell subset," Oncotarget, 2015, 6(15):13835-13843.
Li et al., "Impact of chemokine receptor CXCR3 on tumor-infiltrating lymphocyte recruitment associated with favorable prognosis in advanced gastric cancer," Int J Clin Exp Pathol, 2015, 8(11):14725-14732.
Rathore et al., "CD3+, CD4+ & CD8+ tumour infiltrating lymphocytes (TILs) are predictors of favourable survival outcome in infiltrating ductal carcinoma of breast," Indian J Med Res, 2014, 140:361-369.
Santegoets et al., "IL-21 promotes the expansion of CD27+CD28+ tumor infiltrating lymphocytes with high cytotoxic potential and low collateral expansion of regulatory T cells," J Transl Med, 2013, 11:37-47.
Takeha et al., "Stromal Expression of MMP-9 and Urokinase Receptor is Inversely Associated with Liver Metastasis and with Infiltrating Growth in Human Colorectal Cancer: A Novel Approach from Immune/Inflammatory Aspect," Jpn. J. Cancer Res., 1997, 88:72-81.
Cho et al., "Targeted Genome Engineering in Human Cells with RNA-Guided Endonucleases," Nature Biotechnology, Supplemental Information, Jan. 11, 2013.
Liescu et al., Continuous Field-Flow Separation of Particle Populations in a Dielectrophoretic Chip with Three Dimensional Electrodes, Applied Physics Letters 90:234104 (2007).
Lecault et al., "Microfluidic single cell analysis: from promise to practice" Current Opinion in Chemical Biology, vol. 16, No. 3-4, Aug. 1, 2012, pp. 381-390.
Lee et al., "Microchip-based one step DNA extraction and real-time PCR in one chamber for rapid pathogen identification" Lab on Chip 2006.
Ramadan, Q. et al., Simultaneous cell lysis and bead trapping in a continuous flow microfluidic device. Sensors and Actuators B, Jun. 6, 2005, vol. 113, No. 2, pp. 944-955.
WO2010147078, University of Tokyo, Machine Translation, Dec. 23, 2010, 12 pages.
Xu, Guoling et al.,. Recent Trends in Dielectrophoresis, Informacije MIDEM, 2010, vol. 40, Issue No. 4, pp. 253-262.

* cited by examiner

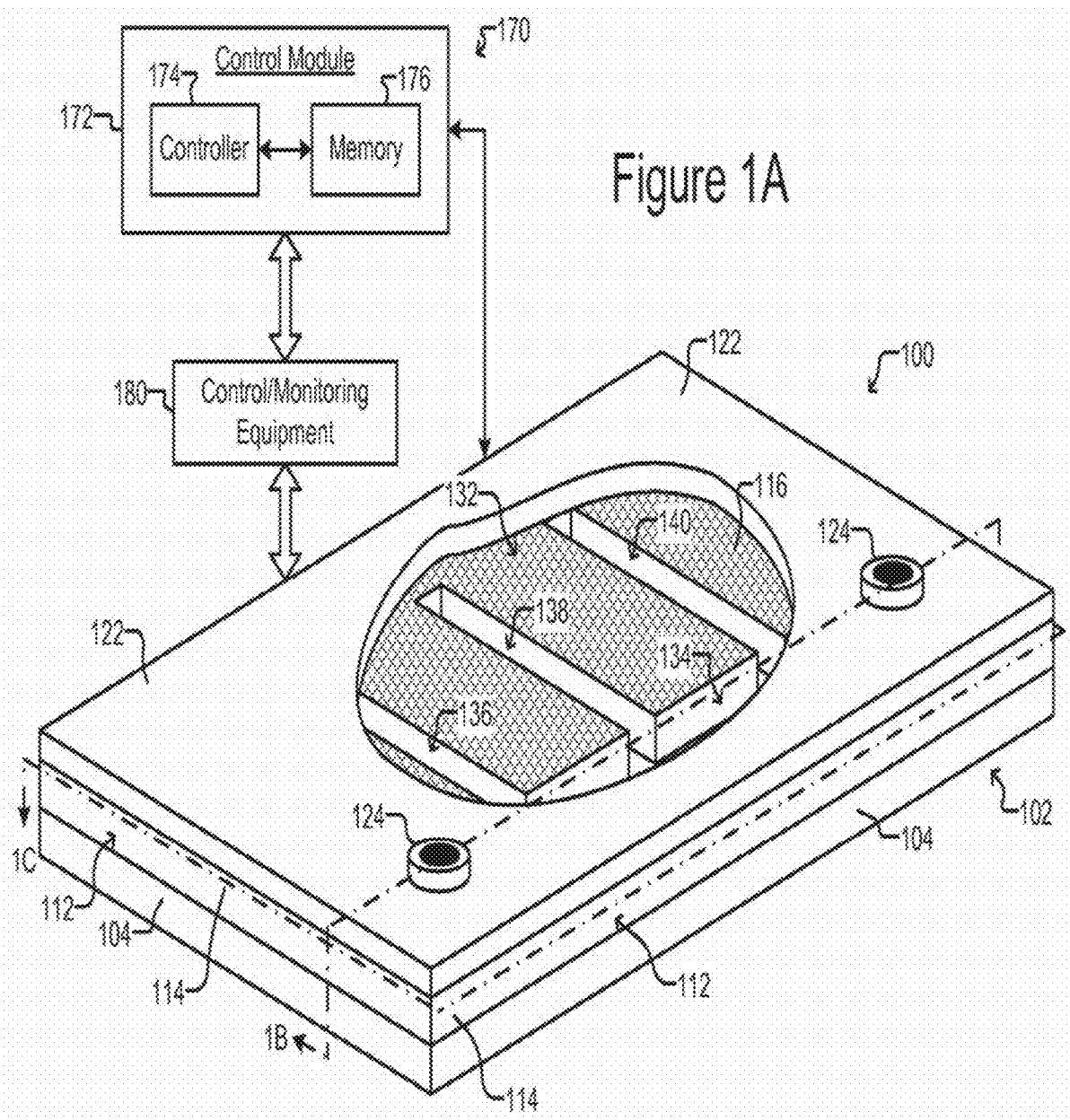

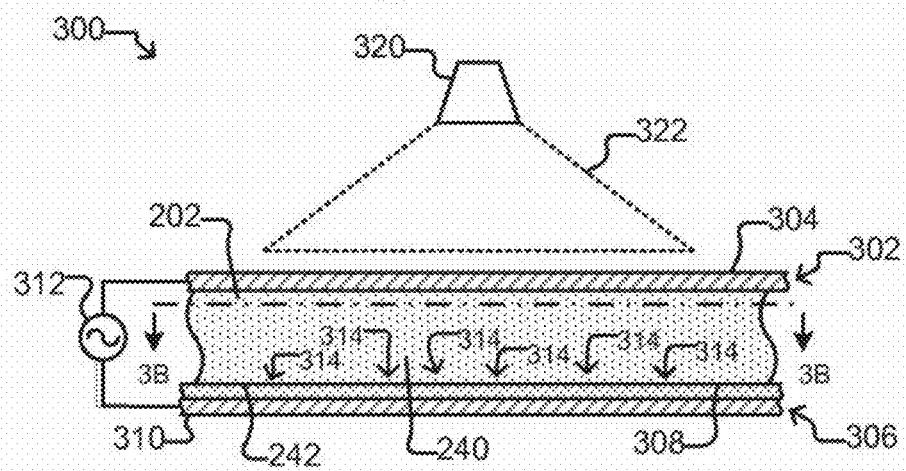
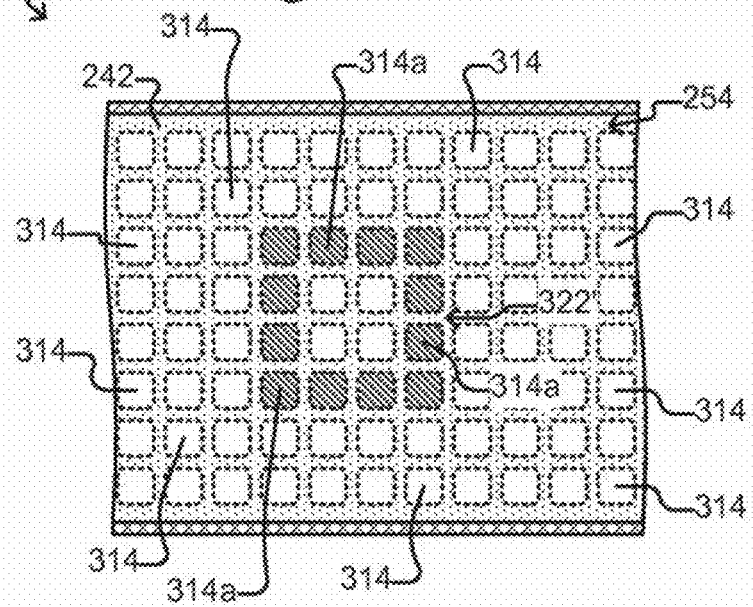

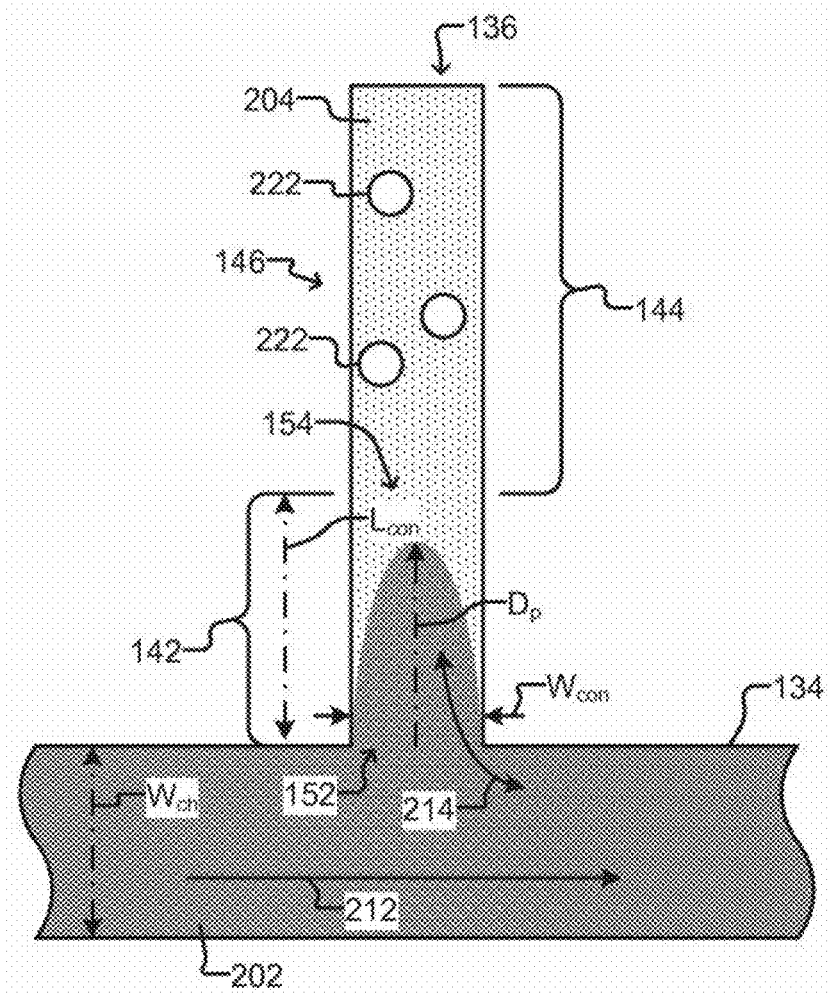

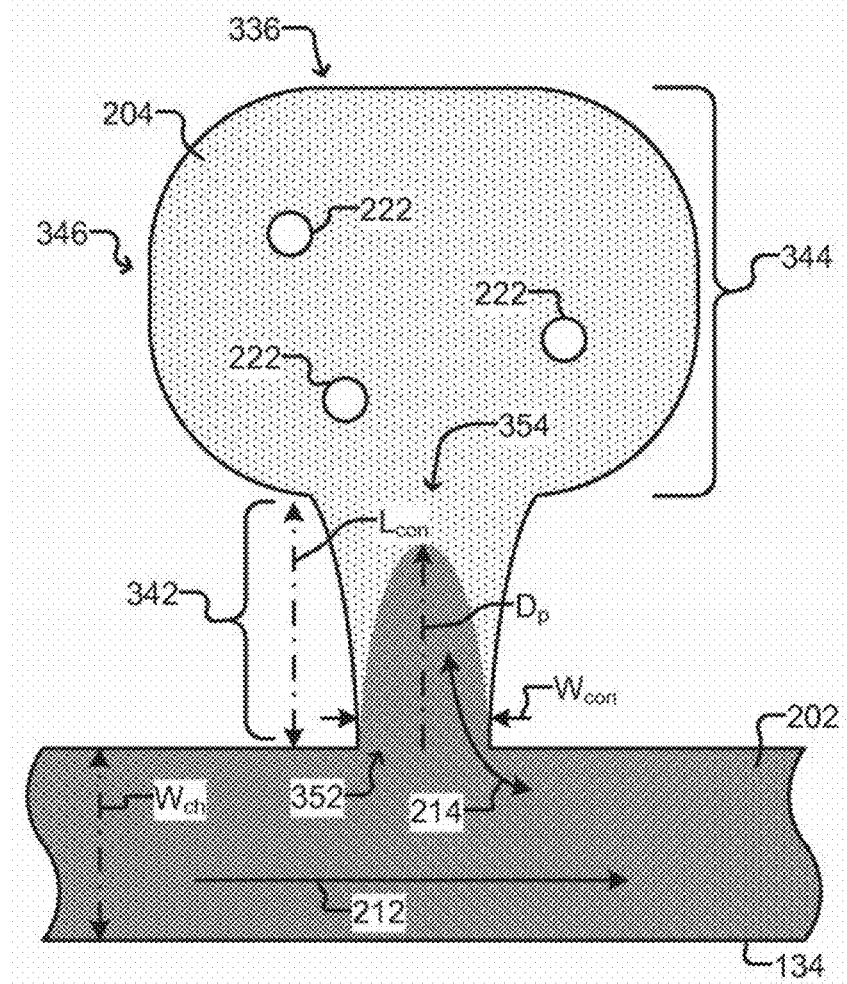

Hours of culture

Hours of culture

Figure 13A
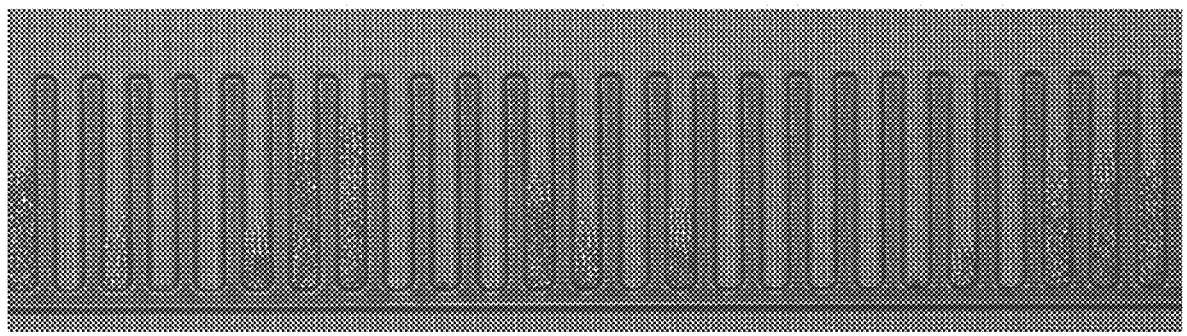
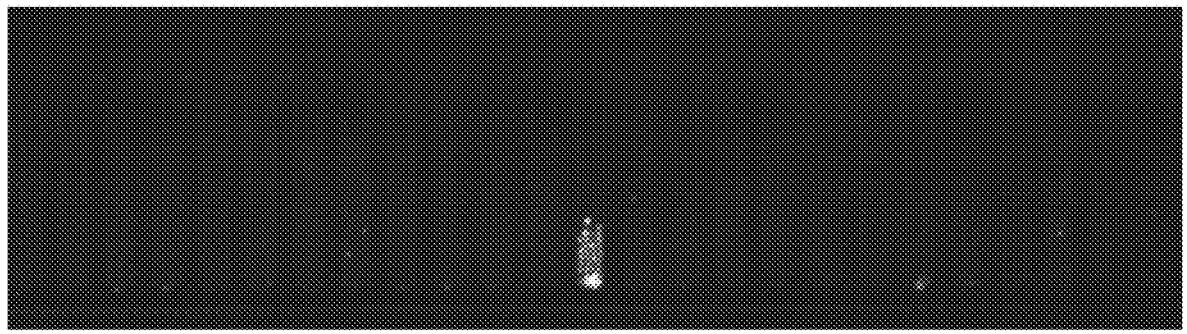
Figure 13B

TUMOR INFILTRATING CELLS ENGINEERED TO EXPRESS A PRO-INFLAMMATORY POLYPEPTIDE

This application is a continuation of application of PCT/US2016/069468, which was filed on Dec. 30, 2016, and claims priority to U.S. Provisional Application No. 62/274,059, filed Dec. 31, 2015, which applications are incorporated herein by reference in their entirety.

FIELD OF THE INVENTION

The present disclosure relates to genetically engineered cell populations and, in particular, genetically engineered cells that can target tumors and deliver a pro-inflammatory agent to the site of the tumor.

BACKGROUND

T cells have been developed as a therapeutic agent for many years (see, e.g., Sharpe et al., Disease Models & Mechanisms 8, 337-350 (2015); Maus et al., Annul. Rev. Immunol. 32, 289-225 (2014), Wu et al., Cancer J. 18, 160-175 (2012)). Moreover, antigen specificity of T cells has been genetically manipulated to be redirected against target antigens expressed by tumors. In particular, T cells have been engineered to express modified TCRs (so-called TCR therapies) or protein-fusion-derived chimeric antigen receptors (CARs) that have enhanced specificity for a target antigen. CARs combine antibody-like recognition with a T-cell-activating function (Maher, ISRN Oncol. 2012 278093). They include an antigen-binding region, derived from an antibody, ligand or receptor (Eshhar et al., PNAS 90, 720-724 (1993)), a transmembrane domain to anchor the CAR to the T cell (Bridgeman et al., J. Immunol. 184 6938-6949 (2010)), and one or more intracellular signaling domains that induce persistence, trafficking and effector functions in transduced T cells (Finney et al., J. Immunol. 161, 2791-2797 (1998); Krause et al., J. Exp. Med. 188, 619-626 (1998)). The targeting domain, often a single-chain FV fragment is linked via a flexible spacer region to an intracellular signaling domain, typically the transmembrane and endodomain of the CD3ζ or FCRγ receptor.

Tumor infiltrating lymphocytes (TILs) are thought to be the result of naturally occurring T cell responses to a tumor. TILs, which can be isolated from tumor tissue, have an innate ability to infiltrate and target specific types of tumors. Isolated TILs can be cultivated, activated and expanded ex vivo. On reinfusion into patients, TILs have shown therapeutic activity in clinical trials, particularly in the treatment of melanoma (Rosenberg et al., Adv Exp Med Biol. 1988; 233:459-467, Besser et al., Clin Cancer Res. 2010; 16(9): 2646-2655; Kvistborg et al., J Immunother. 2011; 34(9):677; Dudley, J Cancer. 2011; 2:360-362)). Positive response rates in humans have approached 50%, with durable and complete regression in about 13% of human patients. Such response rates highlight the promise of the technique, as well as room for improvement.

PARTIAL SUMMARY OF THE INVENTION

An isolated tumor-infiltrating cell (TIC) genetically engineered to provide increased expression of a pro-inflammatory protein other than a chimeric antigen receptor (CAR) is provided. Optionally, the TIC is genetically engineered for expression of an exogenous nucleic acid encoding a transcriptional activator that increases expression of the pro-inflammatory protein or for expression of an exogenous nucleic acid encoding the pro-inflammatory protein. Optionally, the TIC also includes a nucleic acid encoding a CAR. Optionally, the TIC is derived from a cell isolated from a solid tumor biopsy. Optionally, the TIC is derived from a cell isolated from peripheral blood or a lymphoid tissue. Optionally, the TIC is a leukocyte. Optionally, the TIC is a T cell, B cell, macrophage, or NK cell. Optionally, the TIC expresses at least one marker selected from the group of CD3, CD4, CD8, T-bet, GATA-3, CD25, Foxp3, and ROR-gammaT. Optionally, the cell expresses at least one marker selected from the group of CD1d, CD5, CD19, CD20, CD21, CD22, CD23, CD24, CD38, CD40, CD72, and CD79a,b. Optionally, the cell expresses at least one marker selected from the group of CD56, CD16, F480, siglec3, and gamma receptor. Optionally, the exogenous nucleic acid encodes a cytokine. Optionally, the cytokine is selected from the group consisting of IL-2, IL-7, IL-15, IFN (type 1 or 2), CSF, GM-CSF, IL-21, and TNF-alpha. Optionally, the exogenous nucleic acid encodes an antibody, which may be a single-chain antibody. Optionally, the antibody specifically recognizes (e.g., specifically inhibits) a checkpoint protein. Optionally, the antibody is selected from the group of anti-CTLA-4, anti-PD-1, and anti-PD-L1. Optionally, the exogenous nucleic acid encodes a chemokine. Optionally, the chemokine is selected from the group of RANTES, IP-10, CXCL9, and CXCL10. Optionally, the exogenous nucleic acid encodes a microbial antigen. Optionally, the microbial antigen is selected from the group of SEA, SEA/E-120, and a bacterial flagellar protein. Optionally, the pro-inflammatory protein is expressed as a fusion protein. Optionally, the exogenous nucleic acid is operably linked to an inducible promoter. Optionally, the inducible promoter is a tetracycline-inducible promoter. Optionally, the TIC further comprises a nucleic acid encoding a matrix degrading enzyme. Optionally, the matrix degrading enzyme is selected from the group of heparinase, collagenase, a matrix metalloproteinase, and plasminogen activator. Optionally, the matrix degrading enzyme is MMP9 or urokinase.

Also provided is a method of preparing a tumor-infiltrating cell, the method comprising: obtaining a sample from a patient; isolating tumor-infiltrating cells from the sample; and transforming the tumor-infiltrating cells with an exogenous nucleic acid encoding a pro-inflammatory polypeptide other than a chimeric antigen receptor (CAR) or a transcription factor that induces expression of the pro-inflammatory polypeptide. Optionally, the sample comprises a tumor biopsy or a fine needle aspirate (FNA). The FNA can be from in a tumor or from around the tumor. Optionally, the sample comprises peripheral blood or a lymphoid tissue, such as a tumor-draining lymph node biopsy or FNA. Optionally, the step of isolating tumor-infiltrating cells from the sample comprises dissociating the sample (e.g., partially or substantially completely) into single cells. Optionally, the TIC is a tumor-infiltrating lymphocyte (TIL). Optionally, the TIC is a cytotoxic T cell, T helper cell, and/or B cell. Optionally, isolating the tumor-infiltrating cells comprises contacting the cells with an agent that specifically binds to a cell type-specific cell surface marker. The cell surface marker can be specific to a desirable cell type, such as T cells, NK cells, or macrophages. For example, the agent can be an anti-CD4 and/or anti-CD8 antibody. Alternatively, the cell surface marker can be specific to non-immunological cell types, which may provide for a negative selection. Optionally, the agent is attached to a solid support. Optionally, isolating tumor-infiltrating cells comprises performing FACS or MACS. Optionally, isolating the tumor-infiltrating cells comprises introducing the cells into a microfluidic device and placing one or more cells into each of a plurality of isolation chambers located within the microfluidic device. Optionally, the microfluidic device is a nanofluidic device. Optionally, the microfluidic or nanofluidic device comprises at least one internal surface that is conditioned to support cell growth and/or maintenance. Optionally, the conditioned surface is a surface described herein. For example, the conditioned surface may comprise covalently linked polymers. Optionally, the polymers may comprise polyethylene glycol (PEG), one or more monosaccharides, disaccharides, or polysaccharides, or one or more peptides or proteins. Optionally, the conditioned surface may comprise a combination of different types of covalently linked polymers (e.g., polymers comprising PEG in combination with polymers comprising peptides or proteins). Optionally, placing the one or more cells into isolation chambers comprises using an electrokinetic force to move the cells into the plurality of isolation chambers. Optionally, the electrokinetic force is a dielectrophoretic force. Optionally, the steps of introducing the cells into the microfluidic device and placing one or more cells into each of a plurality of isolation chambers are performed after the step of transforming the tumor-infiltrating cells. Optionally, transforming the tumor-infiltrating cells comprises transforming the cells with a viral vector. Optionally, the viral vector is a lentiviral vector. Optionally, transforming the tumor-infiltrating cells comprises introducing CRISPR-Cas9, a TALEN, or a zinc finger protein into the cells. Optionally, the method also includes culturing the transformed cells within the isolation chambers of the microfluidic device. Optionally, the transformed cells are cultured individually in separate isolation chambers to thereby produce clonal populations of transformed cells. Optionally, the method also includes culturing the transformed cells in the presence of rapamycin. Optionally, the method also includes administering a transformed cell to a patient. Optionally, the transformed cell is the same patient from whom the sample was obtained.

Also provided is a method of treating a patient having a cancer, the method comprising administering to the patient an effective regime of a genetically engineered tumor-infiltrating cell as described above. Optionally, the cancer is a melanoma, a breast cancer, a genitourinary cancer, a cancer of the nervous system, an intestinal cancer, or a lung cancer. Optionally, the method also includes administering to the patient an agent capable of inducing expression of the exogenous nucleic acid. Optionally, the exogenous nucleic acid comprises a tetracycline-inducible promoter and the agent administered to the patient is tetracycline. Optionally, at least $10^3$ genetically engineered tumor-infiltrating cells are administered to the patient. Optionally, $10^3$-$10^5$ genetically engineered tumor-infiltrating cells are administered to the patient. Optionally, the genetically engineered tumor-infiltrating cells administered to the patient comprise a mixture of genetically engineered tumor-infiltrating cell populations, each population clonally derived from a single genetically engineered tumor-infiltrating cell.

Also provided are compositions comprising a mixture of genetically engineered tumor-infiltrating cell populations. Each population can be clonally derived from a single type of genetically engineered tumor-infiltrating cell described herein. Optionally, the composition contains substantially no cells other than the cells from one of the clonal populations of genetically engineered tumor-infiltrating cells described herein. Optionally, at least 50% (e.g., at least 60%, at least 70%, at least 75%, at least 80%, at least 85%, at least 90%, at least 95%, at least 96%, at least 97%, at least 98%, at least 99%, at least 99.5%, or more) of the cells in the mixture are from one of the clonal populations of genetically engineered tumor-infiltrating cells described herein. Optionally, the composition comprises at least $10^3$ cells (e.g., at least $10^4$ cells, at least $10^5$ cells, or at least $10^6$ cells). Optionally, the composition further comprises a pharmaceutically acceptable carrier.

BRIEF DESCRIPTION OF THE DRAWINGS

FIG. 1A is a perspective view of an exemplary microfluidic device for separating tumor infiltrating cells.

FIG. 1D is side cross-sectional view of an exemplary microfluidic device having a dielectrophoresis (DEP) configuration.

FIG. 1E is a top, cross-sectional view of the microfluidic device of FIG. 1D.

FIG. 2 illustrates an example of a portion of a microfluidic device having a flow channel and an isolation chamber, and in which a length of a connection region from the flow channel to an isolation region in the isolation chamber is greater than a penetration depth of medium flowing in the flow channel.

FIG. 3 is another example of a portion of a microfluidic device having a flow channel and an isolation chamber, and in which the isolation chamber comprises a connection region from the flow channel to an isolation region that is longer than a penetration depth of medium flowing in the flow channel.

FIGS. 13A and 13B are photographic representations of an embodiment of genetically modified T cells cultured in a microfluidic device (FIG. 13A) and the same cells stained with a fluorescently-labeled antibody specific to the protein normally produced by the gene targeted in the genetic modification.

Figure 1B:
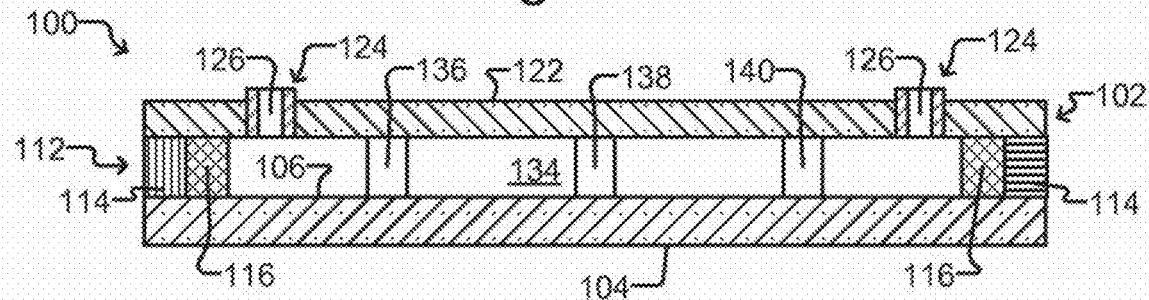
FIG. 1B is a side, cross-sectional view of the microfluidic device of FIG. 1A.

The figures may show simplified or partial views, and the dimensions of elements in the Figures may be exaggerated or otherwise not in proportion for clarity.

DEFINITIONS

A polypeptide is pro-inflammatory if it causes a systemic or localized increase in inflammation. The increase in inflammation can be characterized by, for example: an increased ratio of activation states or numbers of immune cells with effector functions compared with immune cells with regulatory functions; increased level of one or more pro-inflammatory cytokines and/or chemokines (other than the polypeptide administered); decreased level of one or more anti-inflammatory cytokines; increased levels of antibodies; release of histamine; and/or increased body temperature. Examples of pro-inflammatory cytokines include IL-1, IL-2, IL-6, IL-7, IL-8, IL-15, IL-21, TNF alpha, IFN-gamma, CSF, and GM-CSF. Examples of pro-inflammatory chemokines include CXCL-8, CCL2, CCL3, CCL4, CCL5, CCL11, and CXCL10. Examples of anti-inflammatory cytokines include IL4, IL10, IL13, IL16, IL35, IFN-alpha, TGF-beta, IL1ra, and G-CSF.

Tumor infiltrating cells can be provided in an isolated form. This means that the tumor infiltrating cells are provided as an ex vivo population of cells which has been processed to remove certain biological molecules and/or cell types normally associated with the tumor infiltrating cells in vivo. Such processing can include partial digestion of extracellular protein, cellular dissociation, fractionation, cell culture, cell amplification, and/or cell enrichment. Cell amplification can include targeted amplification, such as occurs when immune cells are amplified in response to an antigenic stimulus (e.g., an antigenic stimulus associated with tumor cells). Cell enrichment can include the marker-based enrichment (e.g., using cell surface markers) for desirable immunological cell types. Optionally, tumor infiltrating cells are at least 20%, 30%, 40%, 50%, 60%, 70%, 75%, 80%, 85%, 90%, 95%, 98%, or 99% of the total cells in the ex vivo population.

Specific binding of a monoclonal antibody or tumor infiltrating cell to its target antigen means an affinity of at least $10^6$, $10^7$, $10^8$, $10^9$, or $10^{10}$ M$^{-1}$. Specific binding is detectably higher in magnitude and distinguishable from non-specific binding occurring to at least one unrelated target. Specific binding can be the result of formation of bonds between particular functional groups or a particular spatial fit (e.g., lock and key type), whereas nonspecific binding is usually the result of van der Waals forces. Specific binding does not however necessarily imply that a monoclonal antibody or tumor infiltrating cell binds one and only one target.

A tumor infiltrating cell has "targeting" capacity for a tumor if it binds to the tumor (or cancer cells within the tumor) with greater affinity than it binds to normal tissue of the same type (or non-cancer cells within the normal tissue) and/or, after systemic introduction into a patient, is found in greater concentration in at least one tumor than in non-tumor tissues of the patient.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region, means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, Fundamental Immunology (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md., 1987 and 1991), or Chothia & Lesk, J. Mol. Biol. 196:901-917 (1987); Chothia et al., Nature 342:878-883 (1989). Kabat also provides a widely used numbering convention (Kabat numbering) in which corresponding residues between different heavy chains or between different light chains are assigned the same number.

The term "antibody" includes intact antibodies and binding fragments thereof. Typically, fragments compete with the intact antibody from which they were derived for specific binding to the target. Such antibody fragments can include separate heavy chains, separate light chains, Fab, Fab', F(ab')2, F(ab)c, Dabs, nanobodies, and Fv. Antibody fragments can be produced by recombinant DNA techniques, or by enzymatic or chemical separation of intact immunoglobulins. The term "antibody" also includes a bispecific antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of either the ABC2 or ABC 101 antibody are included in the invention.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. Nos. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly, a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly, a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 80%, 85%, 90%, 95%, or 100% of corresponding residues defined by Kabat are identical.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

A polypeptide refers to any polymer of amino acids regardless of length, and thus includes for example, natural proteins, engineered proteins, such as an scFV, protein fragments that include at least one structural domain or protein fold, and short peptides, such as an immunogenic peptide from a microbial antigen.

The term "patient" includes human and other mammalian subjects that receive either prophylactic or therapeutic treatment. Thus, for example, a patient can include a xenographic model in which human cancer cells are implanted into a rodent to test the effect of a therapy.

Compositions or methods "comprising" one or more recited elements may include other elements not specifically recited. For example, a composition that comprises antibody may contain the antibody alone or in combination with other ingredients.

"About" refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

"Substantially" means sufficient to work for the intended purpose. The term "substantially" thus allows for minor, insignificant variations from an absolute or perfect state, dimension, measurement, result, or the like such as would be expected but that do not appreciably affect overall performance. When used with respect to numerical values or parameters or characteristics that can be expressed as numerical values, "substantially" means within ten percent.

The term "micro-object" refers generally to any microscopic object that may be isolated and/or manipulated in accordance with the present disclosure. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells; biological organelles; vesicles, or complexes; synthetic vesicles; liposomes (e.g., synthetic or derived from membrane preparations); lipid nanorafts, and the like; or a combination of inanimate micro-objects and biological micro-objects (e.g., microbeads attached to cells, liposome-coated micro-beads, liposome-coated magnetic beads, or the like). Beads may include moieties/molecules covalently or non-covalently attached, such as fluorescent labels, proteins, carbohydrates, antigens, small molecule signaling moieties, or other chemical/biological species capable of use in an assay. Lipid nanorafts have been described, for example, in Ritchie et al. (2009) "Reconstitution of Membrane Proteins in Phospholipid Bilayer Nanodiscs," Methods Enzymol., 464:211-231.

"Cell" is used interchangeably with the term "biological cell." Non-limiting examples of biological cells include eukaryotic cells, plant cells, animal cells, such as mammalian cells, reptilian cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell can be, for example, from a human, a mouse, a rat, a horse, a goat, a sheep, a cow, a primate, or the like.

A colony of biological cells is "clonal" if all of the living cells in the colony that are capable of reproducing are daughter cells derived from a single parent cell. In certain embodiments, all the daughter cells in a clonal colony are derived from the single parent cell by no more than 10 divisions. In other embodiments, all the daughter cells in a clonal colony are derived from the single parent cell by no more than 14 divisions. In other embodiments, all the daughter cells in a clonal colony are derived from the single parent cell by no more than 17 divisions. In other embodiments, all the daughter cells in a clonal colony are derived from the single parent cell by no more than 20 divisions. The term "clonal cells" refers to cells of the same clonal colony.

A "colony" of biological cells refers to 2 or more cells (e.g. about 2 to about 20, about 4 to about 40, about 6 to about 60, about 8 to about 80, about 10 to about 100, about 20 about 200, about 40 about 400, about 60 about 600, about 80 about 800, about 100 about 1000, or greater than 1000 cells).

The term "maintaining (a) cell(s)" refers to providing an environment comprising both fluidic and gaseous components and, optionally a surface, that provides the conditions necessary to keep the cells viable and/or expanding.

A "component" of a fluidic medium is any chemical or biochemical molecule present in the medium, including solvent molecules, ions, small molecules, antibiotics, nucleotides and nucleosides, nucleic acids, amino acids, peptides, proteins, antibodies, sugars, carbohydrates, lipids, fatty acids, cholesterol, metabolites, or the like.

When used in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

Used in reference to a fluidic device, particularly a microfluidic or nanofluidic device, "fluidically connected" means that, when different regions of the device are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a fluidic device can have different compositions (e.g., different concentrations of solutes, such as proteins, carbohydrates, ions, or other molecules) which are in flux as solutes move down their respective concentration gradients and/or fluids flow through the device.

DETAILED DESCRIPTION

I. General

The disclosure provides methods of preparing tumor infiltrating cells (TICS) engineered to express a pro-inflammatory polypeptide. The pro-inflammatory polypeptide is expressed from the tumor infiltrating cell to counter a generally immunosuppressive state within and/or around tumors resulting from an imbalance between the number and activation state of immune effector cells versus those of suppressor cells. Delivering the proinflammatory polypeptide via expression from the TICs as distinct from systemic administration reduces side effects from increasing inflammation at sites remote from a tumor to be treated. The pro-inflammatory polypeptide can be endogenous to the TICs, but can exhibit increased expression or efficacy as a result of the expression of a transcription factor from an exogenous nucleic acid sequence or cassette that increases expression of the pro-inflammatory polypeptide or decreases production of an anti-inflammatory polypeptide. Alternatively, the pro-inflammatory polypeptide can be expressed from an exogenous nucleic acid sequence or cassette. The pro-inflammatory polypeptide can be a pro-inflammatory chemokine or cytokine. Such polypeptides can stimulate immune responses within and/or around a tumor and lead to propagation of the tumor infiltrating cell. The pro-inflammatory polypeptide can be an antibody, such as a checkpoint inhibitor, e.g., anti-PD-1, anti-PD-L1, or anti-CTLA-4. Alternatively, the polypeptide can be an antigen that stimulates an immune response against the antigen and thereby creates a more pro-inflammatory environment within and/or around a tumor. Although understanding of mechanism is not required for practice of the invention, it is believed that tumor infiltrating cells act against a tumor by direct cytotoxicity and/or indirectly via release of cytokines or chemokines that stimulate other components of the immune system to kill tumor cells.

II. Types of Tumors

The tumor can be breast cancer, genitourinary cancer, a cancer of the nervous system, intestinal cancer, lung cancer, melanoma, or another type of cancer. An exemplary breast cancer is medullary breast cancer. A genitourinary cancer may be a cancer originating in the urinary tract, such as in the kidneys (e.g., renal cell carcinoma), ureters, bladder, or urethra. A genitourinary cancer may be a cancer of the male reproductive tract (e.g., testicular cancer, prostate cancer, or a cancer of the seminal vesicles, seminal ducts, or penis) or of the female reproductive tract (e.g., ovarian cancer, uterine cancer, cervical cancer, vaginal cancer, or a cancer of the fallopian tubes). A cancer of the nervous system may be neuroblastoma or glioblastoma. An intestinal cancer may be a colon, rectal or stomach cancer. A lung cancer may be mesothelioma.

Cancers are often characterized by specific markers. One or more of these markers can be used to select for or against cancer cells during the separation of tumor infiltrating cells.

For breast cancer, CD44, HLA-DR, Ki-67 (or MK167), aldehyde dehydrogenase 1 (ALDH1), and ganglioside GD2 tend to be present and/or elevated in cancer cells, whereas estrogen receptor (ER), progesterone receptor (PR), human epidermal growth factor receptor 2 (HER2), and CD24 tend to be absent or reduced in cancer cells; ER-/PR-/HER2-/HLA-DR+ can be used to identify medullary breast cancer cells; and CD44hi/CD24lo/ALDH1hi or CD44hi/CD24lo/GD2hi can be used to identify breast cancer stem cells.

For renal cancer, C-reactive protein, aquaporin-1 (AQP1), adipophilin (ADFP), insulin-like growth factor II mRNA binding protein 3 (IGF2BP3 or IMP3), B7-H1 (or PD-L1), and Ki-67 (MK167) tend to be present and/or elevated in cancer cells.

For bladder cancer, nuclear mitotic apparatus protein (NMP22), bladder tumor antigen (BTA), and fibrin/fibrinogen degradation products tend to be present and/or elevated in cancer cells, while adipocyte fatty acid binding protein (A-FABP), glutathione S-transferase mu (GST-μ), prostaglandin dehydrogenase (PGDH), and keratin 13 tend to be absent or reduced relative to normal cells; at the genetic level, the p16 tumor suppressor gene or the 9p21 locus may be deleted in bladder cancer cells.

For urothelial cancer, complement factor H-related protein (CFHrp) may exhibit increased levels and/or secretion in cancer cells; at the nuclear level, telomerase reverse transcriptase (TERT) tends to exhibit increased mRNA expression in cancer cells.

For endometrial cancer, cancer antigen 15-3 (CA15-3), cancer antigen 125 (CA125), cancer antigen 19.9 (CA19.9), cancer antigen 72.4 (CA72.4), and carcinoembryonic antigen (CEA) tend to be present and/or elevated in cancer cells.

For ovarian cancer, tumor-associated trypsin inhibitor (TATI), cancer antigen 125 (CA125), Claudin5, human epidydmis protein 4 (HE4), carcinoembryonic antigen (CEA), VCAM-1, and miR-181a tend to be present and/or elevated in cancer cells; TATI, CA125, and Claudin 5 have been used in combination to diagnose ovarian cancer, as have HE4 and CA125, optionally in conjunction with CEA and VCAM-1; STAT1 can be used to distinguish between ovarian cancers that are responsive to chemotherapy and those that are not.

For cervical cancer, human papilloma virus (HPV) (e.g., types 16, 18, 31, 33, 35, 39, 45, 51, 52, 56, 58, 59, 68, 6, 11, 42, 43, and 44), p16INK4a, and insulin-like growth factor II mRNA binding protein 3 (IGF2BP3 or IMP3) tend to be present and/or elevated in cancer cells.

For prostate cancer, prostate specific antigen (PSA), sarcosine (a metabolite), prostate cancer gene 3 (PCA3), and TMPRSS2:ERG fusion product tend to be present and/or elevated in cancer cells, while prostatic acid phosphatase, fibrinogen a chain precursor, collagen α-1 (III), collagen α-1 (I), psoriasis susceptibility 1 candidate gene 2 protein, hepatocellular carcinoma associated protein TB6, histone H2BB, osteopontin, polymeric Ig receptor, Na/K-transporting ATPase γ, transmembrane secretory component, and semenogelin 1 tend to be absent or reduced relative to normal cells.

For neuroblastoma, increased levels and/or secretion of vanillylmandelic acid (VMA), homovanillic acid (HVA), and ferritin are associated with cancer cells, and neuron-specific enolase (NSE), lactate dehydrogenase (LDH), and ganglioside GD2 tend to be present and/or elevated in cancer cells; at the genomic level, deletions in parts of chromosomes 1p and 11q and duplication of a part of 17q are associated with cancer cells.

For colorectal cancer, carcinoembryonic antigen (CEA), cancer antigen 19-9 (CA19-9), colon-cancer-specific antigen 3 (CCSA-3), colon-cancer-specific antigen 4 (CCSA-4), and B-Raf mutation V600E tend to be present and/or elevated in cancer cells; at the genetic level, colorectal cancer cells exhibit microsatellite instability and various K-Ras mutations.

For small cell lung carcinoma, ganglioside GD2 tends to be present and/or elevated in cancer cells; for non-small cell lung carcinoma, B-Raf mutation V600E tends to be present in cancer cells; for mesothelioma, calretinin, cytokeratin 5/6, and WT1 tend to be present and/or elevated in cancer cells, while carcinoembryonic antigen (CEA), epithelial cell adhesion molecule (Ep-CAM)(e.g., as detected by the MOC-31 or Ber-EP4 antibodies), Lewis Y blood group (e.g., as detected by the BG-8 antibody), and the tumor associated glycoprotein detected by the B72.3 antibody tend to be absent or reduced; and, conversely, for pulmonary adenocarcinoma, CEA, Ep-CAM (e.g., as detected by the MOC-31 or Ber-EP4 antibodies), Lewis Y blood group (e.g., as detected by the BG-8 antibody), and the tumor associated glycoprotein detected by the B72.3 antibody tend to be present and/or elevated in cancer cells, while calretinin, cytokeratin 5/6, and WT1 tend to be absent or reduced.

For melanoma, the human endogenous retrovirus (HERV-K), ganglioside GD2, B-Raf mutation V600E, Hsp90, regulator of G-protein signaling 1 (RGS1), Osteopontin, human epidermal growth factor receptor 3 (HER3), nuclear receptor coactivator 3 (NCOA3), and minichromosome maintenance complex components 4 and 6 (MCM4 and MCM6, respectively) tend to be present and/or elevated in cancer cells, while inhibitor or growth proteins 3 and 4 (ING3 and ING4, respectively) tend to be absent or reduced relative to normal cells.

III. Tumor Infiltrating Cells

Tumor infiltrating cells (TICs) are noncancerous cells of the immune system that are capable of targeting at least one type of tumor (e.g., a tumor described herein). In some embodiments, the TICs are isolated from a tumor (e.g., a tumor described herein) or are progeny resulting from propagation of primary tumor cells that substantially retain tumor targeting capacity. In other embodiments, the TICs are isolated from a tissue source other than a tumor (e.g., peripheral blood, particularly PBMCs, or a lymphoid tissue, particularly bone marrow or peripheral lymph nodes) or are progeny resulting from propagation of primary cell isolates from such non-tumor tissues. Regardless of the tissue from which the TICs are isolated, they possess targeting capability for at least one type of tumor. Tumor infiltrating cells of the invention include progeny cells that have been genetically engineered to express a proinflammatory polypeptide. The genetically engineered TICs can have enhanced activity, such as enhanced tumor targeting and/or enhanced effector function(s). In addition, the genetically engineered TICs can substantially retain the morphology and/or genetic markers of the TICs from which they are derived. Tumor infiltrating cells are often referred to as TILs in the scientific literature, for tumor infiltrating lymphocytes. However, not all tumor infiltrating cells are necessarily lymphocytes. Thus, the term TICs is used more generally herein to refer to any tumor infiltrating immune cell.

TICs can be part of the innate or adaptive immune system. TICs include leukocytes (e.g., neutrophils, esoninophils, basophils, lymphocytes, monocytes, and macrophages) and dendritic cells. Lymphocytes include T-cells, T memory stem cells (TSCM), T effector memory cells (TEMC), γδ T cells, B cells, plasma cells, and natural killer (NK) cells. The TICs can be one or more types of T helper cells, such as Th1 cells, CD3+/CD4+/T-bet+ cells, Th2 cells, CD3+/CD4+/GATA-3+ cells, Treg cells, CD3+/CD4+/CD25+/Foxp3+ cells, Th17 cells, CD3+/CD4+/ROR-gammaT+ cells, or cytotoxic T cells (e.g., CD3+/CD8+ T cells). Alternatively, the TICs can be B cells (e.g., plasma B cells, memory B cells, regulatory B cells, CD5+CD1d+ cells, and CD24+CD38+ cells) or macrophages.

Some of the most important TICs have direct cytotoxic activity against tumor cells, including cytotoxic lymphocytes, natural killer cells, and lymphokine-activated killer cells.

Cytotoxic T lymphocytes (CTLs) are typically of the CD3+, CD8+, CD4-phenotype. They typically lyse cells that display fragments of foreign antigens associated with class I MHC molecules on their cell surfaces. CTLs typically recognize normal cells expressing antigens after infection by viruses or other pathogens; and tumor cells that have undergone transformation and are expressing mutated proteins or are over-expressing normal proteins. Cytotoxic lymphocytes are known to mediate antigen-specific cytolysis of tumor cells through the action of granzymes, which are serine proteases that cleave at aspartate residues, and perforin, which forms pores in the plasma membrane of tumor cells. Without intending to be bound by theory, perforins are believed to insert into the plasma membranes of target cells and form pores which allow granzymes to enter the target cells, whereupon the granzymes promote cellular apoptosis by activating capsases.

Natural killer cells are a subset of lymphocytes active in the immune system and representing an average 15% of mononuclear cells in human peripheral blood. Among the surface markers used to identify human NK cells is a receptor binding with low affinity to the Fc fragment of IgG antibodies, such as Fc-γ receptor III or CD16 antigen. NK cells have been demonstrated to play an important role in vivo in the defense against tumors, tumor metastases, and virus infection, and to regulate normal and malignant hematopoiesis.

Lymphokine-activated killer (LAK) cells are a cytotoxic population of cells which, in the presence of cytokines (e.g., IL2) are capable of lysing NK-cell resistant tumor cell lines.

In some methods, TICs are obtained from a single tumor in a single patient. In other methods, TICs are obtained from multiple tumors. In such methods, the tumors can be from the same organ (e.g., all breast cancer) or the same cell type (all carcinomas) or both the same organ and cell type. In some methods in which tumor infiltrating cells are obtained from multiple tumors, the tumors are from the same patient, and in other methods from multiple patients. If the tumor infiltrating cells are obtained from multiple patients, the patients are preferably immunologically matched (e.g., HLA matched) to avoid or at least reduce compatibility problems when the cells are introduced into a patient.

Tumor samples can be actively dissociated by obtaining at least one solid tumor sample and dissociating at least one single cell or passively dissociated by obtaining a sample that has been previously dissociated or grown in dissociated form. The dissociation may be conducted in a number of ways. For example, the tumor sample may be dissociated using a collagenase plus DNase digestion. The tumor sample may also be dissociated using a cell dissociator instrument, such as the gentleMACS™ instrument from Miltenyi Biotec.

In some methods, TICs are obtained from a single sample of non-tumor tissue from a single patient. The non-tumor tissue sample can comprise peripheral blood (e.g., PBMCs) or a lymphoid tissue (e.g., bone marrow or one or more peripheral lymph nodes). In other methods, TICs are obtained from multiple non-tumor tissue samples. In some methods in which tumor infiltrating cells are obtained from multiple non-tumor tissue samples, the samples are from the same patient, and in other methods from multiple patients. If the tumor infiltrating cells are obtained from multiple patients, the patients are preferably immunologically matched (e.g., HLA matched) to avoid or at least reduce compatibility problems when the cells are introduced into a patient.

Non-tumor tissue samples, such as peripheral blood or lymphoid tissue, can be actively dissociated by obtaining at least one such sample (e.g., particularly PBMCs, bone marrow, or peripheral lymph nodes) and dissociating at least one single cell or passively dissociated by obtaining a sample that has been previously dissociated or grown in dissociated form. The dissociation may be conducted in a number of ways. For example, the non-tumor tissue sample may be dissociated using a collagenase plus DNase digestion. The non-tumor tissue sample may also be dissociated using a tissue processing instrument, such as the COBE Spectra Apheresis System (e.g., for peripheral blood or bone marrow).

In some methods, a patient is immunized with an antigen from a tumor present in the patient before collecting a tumor sample to harvest TICs. Such immunization can increase representation of TICs with tumor targeting ability in the tumor.

IV. Selecting and Expanding Tumor Infiltrating Cells

Tumor infiltrating cells can be separated from other cells in the dissociated tumor (or blood or lymphoid tissue) by several techniques including affinity separation, FACS, MACs, microfluidics, and combinations thereof. Separation can result in a mixed population of tumor infiltrating cells of different clonal origins and/or different cell types, or can isolate individual cells. Tumor infiltrating cells can be separated from other cells in a tumor (or blood or lymphoid tissue) by selecting for a marker on the tumor infiltrating cells or against a marker on the other cells. Selection of tumor infiltrating cells can be performed before loading cells into a microfluidic (or nanofluidic) device, after genetic engineering of the cells, while the cells are in the microfluidic (or nanofluidic) device, or during two or more such times. Guidance for using technologies for sorting and/or isolating T cells or B cells is disclosed in the following references: Thiel et al, Clin. Immunol, 111(2): 155-161 (2004); Newman et al, J. Immunol. Meth., 272: 177-187 (2003): Hoven et al, J. Immunol. Meth., 117(2): 275-284 (1989); U.S. Pat. Nos. 5,213,960 and 5,326,696; Moody et al, Cytometry A, 73A: 1086-1092 (2008); Gratama et al, Cytometry A, 58A: 79-86 (2004); Davis et al, Nature Reviews Immunology, 11: 551-558 (2011); U.S. Pat. Nos. 8,053,235 and 8,309,312; Lee et al, Nature Medicine, 5(6): 677-685 (1999); Altman et al, Science, 274: 94-96 (1996); Leisner et al, PLosOne 3(2): e1678 (2008); "Pro5 MHC Pentamer Handbook," (Prolmmune, Ltd., United Kingdom, 2012). Analogous technologies for sorting and/or isolating T cell markers for selection include any of CD4, CD8, CD25, CD45RA, CD45RO, CD62L, CD69, and CD3. NK cell markers I CD16 include CD56 and. Macrophage cell markers include F480, siglec3, and gamma receptor. B cell markers include CD19, CD20, IgM, IgD, CD38, CD27, CD138, PNA, and GL7. Tumors cells can be selected for or against one or more tumor-specific antigens (e.g., one or more tumor-specific antigens noted above).

A. Loading and Moving TICs into and within the Microfluidic Device

A microfluidic (or nanofluidic) device can be used to separate individual cells from the dissociated tumor sample(s) (or blood or lymphoid tissue), and characterize the cells by their binding to or activation by a desired target (e.g., cancerous cells from a target tumor, such as a tumor from which the TICs were isolated, or one or more immunogenic antigens from such cancerous cells). TICs having the most desirable properties can be cloned and expanded ex vivo (e.g., within isolation chambers in a microfluidic device, optionally with additional expansion outside of the microfluidic device).

The dissociated cell sample (optionally fractionated as discussed above) can be loaded into the microfluidic (or nanofluidic) device by flowing the cells of the sample through an inlet in the device and into the flow region. In some embodiments, the flow region includes a flow channel, and loading the dissociated cell sample includes flowing the cells into the flow channel.

Once the dissociated cell sample is loaded into the flow region (or flow channel) of the microfluidic (or nanofluidic) device, tumor infiltrating cells in the sample can be moved into isolation regions of the device. For example, tumor infiltrating cells can be moved from the flow region (or flow channel) into one or more isolation regions, which may be located within isolation chambers that are fluidically connected with and open off of the flow region (or flow channel). The movement of the tumor infiltrating cells may be accomplished by a variety of means, including using gravity (such as by tipping the microfluidic device), inducing localized fluid flow (such as by depressing or pulling a deformable surface of the microfluidic device located adjacent or proximal to the isolation region), applying dielectrophoretic (DEP) force (such as the DEP force generated by optoelectronic tweezers (OET)), or any combination thereof.

Prior to loading the dissociated cell sample into the microfluidic (or nanofluidic device), tumor infiltrating cells in the dissociated cell sample can be labeled with at least one detectable marker, such as any of the markers disclosed above. The marker may aid in selecting TICs for selective movement (e.g., using DEP force) from the flow region (or flow channel) of the device to an isolation chamber or an isolation region thereof.

In some instances, only one tumor infiltrating cell is moved into each isolation region, whether all of the isolation regions are loaded or not. In other instances, the tumor infiltrating cells can be initially pooled into one or more isolation regions, and later separated into individual isolation regions (i.e., one tumor infiltrating cell per isolation region). The latter practice allows greater throughput when screening tumor infiltrating cells for desired antigen/target binding.

B. Loading of Cancer Cells, Cancer Cell-Derived Antigen(s), or Other Micro-Particles into the Microfluidic/Nanofluidic Device Cancer cells can be loaded into the microfluidic (or nanofluidic) device (e.g., for the purpose of detecting TIC binding, detecting cancer antigen-induced proliferation of TICs, and/or assaying TIC-dependent cancer cell killing) by flowing the cells or micro-particles through an inlet in the device and into the flow region. TICs can be loaded onto the device before, after, or at the same time as the cancer cells or micro-particles. Thus, for example, when using a combination of TICs and cancer cells from the same tumor, the TICs and cancer cells can be loaded without fractionating the TICs and cancer cells from each other).

In some embodiments, the cancer cells are loaded into the flow region (or flow channel) of the microfluidic (or nanofluidic) device and remain in the flow region (or flow channel) until exported from the device. In some embodiments, the cancer cells do not enter the isolation regions. In some embodiments, the cancer cells dip into the connection regions of isolation chambers in addition to residing in the flow region (or flow channel). In any of these embodiments, the cancer cells can be loaded into the flow region (or flow channel) at a concentration of at least about $1\times10^6$, $5\times10^6$, $1\times10^7$, $2.5\times10^7$, $5\times10^7$, $7.5\times10^7$, or $1\times10^8$ cells/ml.

In other embodiments, the cancer cells are moved into at least one isolation region in the microfluidic (or nanofluidic) device. As with the TICs, movement of the cancer cells can be accomplished by a variety of means, including using gravity (such as by tipping the device), inducing localized fluid flow (such as by depressing or pulling a deformable surface of the device located adjacent or proximal to the isolation region), applying dielectrophoretic (DEP) force (such as by optoelectronic tweezers (OET)), or any combination thereof. In some embodiments, one or more (e.g., only 1, about 2, 3, 4, 5, 6, 7, 8, 9, 10, or more, or from about 1 to 20, 1 to 10, 1 to 5, 1 to 3, 1 to 2) cancer cells can be moved into individual isolation regions in the microfluidic (or nanofluidic) device, thereby obtaining at least one isolation region having an isolated cancer cell or a group of isolated cancer cells. Thus, the isolated cancer cells may be placed in the same isolation regions. Alternatively, the isolated cancer cells/micro-particles and the TICs may be placed in different isolation regions (such as in adjacent isolation regions, which may be connected, e.g., by a narrow passage that allows for diffusion of proteins and other macromolecules or small molecules, but prevents contact between the TICs and the cancer cells). Having cancer cells/micro-particles and TICs in adjacent but connected isolation regions can be advantageous, for example, when assaying for TIC-dependent production of a cancer antigen-binding agent, such as an antibody, and/or for assaying the effect of such antigen-binding agents on cancer cells.

Irrespective of the desired location for the cancer cells in the microfluidic (or nanofluidic) device, the cancer cells may be labeled with one or more detectable markers prior to loading the cancer cells onto the device. If the desired mode includes moving at least one cancer cell into at least one isolation region, the detectable marker(s) may be used to select the at least one cancer cell for movement. Alternatively, or additionally, morphological assessments of the cell size, cell shape, nuclear size, or nuclear structure may be used to select the at least one cancer cell for movement. Cancer cells may also be chosen by the absence of a cellular marker, optionally in combination with morphological assessments.

The cancer cells can originate from the same dissociated cell sample from which the TICs were obtained or from another source. The cancer cells can be cultured and/or cloned prior to being used to assess TIC functionality (e.g., cancer cell-induced proliferation, TIC production of antibodies capable of binding to the cancer cells, TIC-induced cancer cell killing, etc.). Culturing and/or cloning the cancer cells can be performed within the microfluidic (or nanofluidic) device or prior to loading the cancer cells into the device (e.g., using conventional techniques for selecting, culturing, and/or cloning cancer cells from a tumor sample). Regardless, the cancer cells can be selected, cultured, and/or cloned to a concentration of at least about $1\times10^6$, $5\times10^6$, $1\times10^7$, $2.5\times10^7$, $5\times10^7$, $7.5\times10^7$, or $1\times10^8$ cells/ml.

A population of cancer cells derived from a tumor can be relatively heterogeneous with respect to the morphological and genetic characteristics of individual cells that make up the population. For example, the population may contain cancer stem cells (which may divide slowly) and more differentiated cancer cells (which may divide more rapidly and may contain differing subsets of pro-cancer mutations). Marker-based selection and/or cloning of cancer cells can be used to provide more homogeneous populations of cells. Accordingly, a plurality of heterogeneous cancer cells may be loaded onto the microfluidic (or nanofluidic) device. Alternatively, individual cancer cells may be selected and cloned before loading onto the microfluidic (or nanofluidic) device. Thus, a substantially homogeneous population of cancer cells can be loaded into the device and used to identify TICs capable of binding to and/or otherwise interacting with the cancer cells. The substantially homogeneous population can be a cancer cell line derived from the patient providing the at least one tumor sample, or from a different patient.

As an alternative to cancer cells, microparticles having cancer cell-derived antigen(s) or peptides including at least one B-cell or T-cell epitope from such antigen(s) can be used in the presently disclosed methods. The cancer cell-derived antigens can come from any source of cancer cells, including tumor-derived cancer cells (whether from the patient being treated or some other patient), or established cancer cell lines among other sources. Thus, all of the previous disclosure regarding cancer cells being loaded into the microfluidic (or nanofluidic) device (e.g., for the purpose of detecting TIC binding, detecting cancer antigen-induced proliferation of TICs, and/or assaying TIC-dependent cancer cell killing) by flowing the cells or micro-particles through an inlet in the device and into the flow region is equally applicable to microparticles having cancer-derived antigens.

As another alternative to cancer cells, dendritic cells (DCs) loaded with cancer cell-derived antigen(s) or peptides bearing at least one B cell or T cell epitope from such antigen(s) can be used in the presently disclosed methods. Thus, all of the previous disclosure regarding cancer cells being loaded into the microfluidic (or nanofluidic) device (e.g., for the purpose of detecting TIC binding, detecting cancer antigen-induced proliferation of TICs, and/or assaying TIC-dependent cancer cell killing) by flowing the cells or micro-particles through an inlet in the device and into the flow region is equally applicable to dendritic cells loaded with cancer-cell derived antigens.

C. Detection of Binding and Processing of TICs

Binding of TICs (or TIC-secreted agents) to cancer cells may be detected in a variety of ways. For example, cell clumping, such as may occur in an agglutination-type assay, can be used to detect TIC-cancer cell binding. Alternatively, TIC proliferation can be used to detect cell-cell binding between tumor infiltrating lymphocytes (TILS) and target cancer cells or DC cells that have been loaded with tumor-associated antigens. For TIC-secreted antibodies, a secondary antibody, such as an anti-human antibody conjugated to a label (e.g., a fluorescent or luminescent label), may be added to label the cancer cells that have primary antibody (i.e., TIC-secreted antibody) bound to them. As discussed in more detail below, the microfluidic (or nanofluidic) device may comprise an imaging device that allows for visualization of the signal (e.g., TIC-cancer cell clumping, TIC proliferation, or accumulation of label at the surface of the cancer cells). For example, the imaging device can periodically image the microfluidic device and any increases in such signal over time can be detected. The images can be obtain, for example, every few seconds (e.g., every 5, 10, 15, 20, 25, 30, 35, 40, 45, 50, 55, 60 seconds, or more) or every few minutes (e.g., every 2, 3, 4, 5, 6, 7, 8, 9, 10 minutes, or more). In some embodiments, a plurality of images can be overlaid on top of one another, thereby creating a "summed" image which has the general effect of averaging out background signal and creating better contrast between real signal and background signal. The detection of signal can be manual, such as occurs when a person reviews the images, or automated (e.g., using appropriate image analysis software).

Once binding has been detected between cancer cells and the tumor infiltrating cells, tumor infiltrating cells can be identified and their positions (e.g., the isolation regions or isolation chambers in which they are located) can be noted and/or recorded. Optionally, the flow region (or flow channel) may be flushed once tumor infiltrating cell binding to cancer cells has been detected. Such flushing may occur before or after the identification of tumor infiltrating cells that bind to the cancer cells. Tumor infiltrating cells that do not bind to the cancer cells may be discarded from the microfluidic (or nanofluidic) device.

In general, the same or similar methods of detecting binding between cancer cells and TICs can be used mutatis mutandis to detect binding of TICs to microparticles or dendritic cells bearing cancer-derived antigens, and the results of such tests likewise be used to sort TICs suitable for use in subsequent steps. The isolation of cancer cell lysates and the use of dendritic cells pulsed with such lysates to trigger activation of immunological cells has been described, for example, in He et al. (2016), Oncology Letter 12: 1101-06, and Bachleitner-Hoffmann et al. (2002), J. Clin. Endocrin. & Metab. 87(3):1098-1104.

As an optional step, the ability of TICs to bind to or interact with normal tissue or cells (i.e., non-cancerous tissue/cells) can be assessed, and TICs exhibiting more than a background level of binding to normal tissue can be discarded. The normal tissue can be, for example, non-cancerous cells (from the patient providing the TICs or someone else), micro-particles conjugated to non-cancerous cell-derived antigens, or dendritic cells (optionally loaded with non-cancerous cell-derived peptides).

Tumor infiltrating cells identified as binding to cancer cell antigen(s), whether via cancer cells, micro-particles conjugated to cancer cell-derived antigen(s), or dendritic cells loaded with cancer cell-derived antigen(s), may be cultured and/or cloned in the microfluidic (or nanofluidic) device. Such culturing may occur, for example, for at least about 12 hours (e.g., at least about 18, 24, 30, 36, 42, or 48 hours, or at least about 2, 3, 4, 5, 6, 7, 8, 9, 10, or more days (e.g., at least about 12-48 hours, or at least about 2-3 days, 2-4 days, 2-5 days, 2-7 days, 2-10 days, 3-4 days, 3-5 days, 3-7 days, 3-10 days, 4-5 days, 4-7 days, 4-10 days, 5-7 days, or 5-10 days)) and/or to a cell count of at least 2 cells (e.g., at least 3, 4, 5, 6, 7, 8, 9, 10, 12, 15, 20, or more cells (e.g., at least about 2-8 cells, 2-10 cells, 2-12 cells, 2-15 cells, 2-12 cells, 4-8 cells, 4-10 cells, 4-12 cells, 4-15 cells, 4-20 cells, 5-8 cells, 5-10 cells, 5-12 cells, 5-15 cells, 5-20 cells, 8-10 cells, 8-12 cells, 8-15 cells, or 8-20 cells)).

In certain embodiments, tumor infiltrating cells identified as binding to cancer cell-derived antigen(s) can be exported from the microfluidic (or nanofluidic) device. For example, one or more tumor infiltrating cells that bind (e.g., specifically bind) to cancer cell-derived antigen(s) can be exported from the device for nucleic acid sequencing (e.g., transcriptome sequencing, genomic sequencing, and/or sequencing of specific genes or markers, such as the T cell receptor (TCR)). Such sequencing can assist in verification of the cells as having a particular phenotype (e.g., expression of a gene encoding a protein/marker that is otherwise internal to the cell and is specific for a particular cell type, such as a T cell, NK cell, B cell, or macrophage cell type). Alternatively, or in addition, tumor infiltrating cells genetically altered within the microfluidic device or prior to being introduced into the microfluidic device, such nucleic acid sequencing can verify proper targeting of nucleic acid constructs and/or the absence of off-target genetic alterations. Additionally, tumor infiltrating cells that bind (e.g., specifically bind) to cancer cell antigen(s) (and, optionally, successfully engineered to provide increased expression of a pro-inflammatory protein) can be exported from the microfluidic device to prepare the cells for introduction into a patient. Alternatively, tumor infiltrating cells that bind (e.g., specifically bind) to cancer cell antigen(s) can be exported for genetic manipulation off chip. In some instances, each TIC or population of cloned TICs (or fraction thereof) is exported individually (e.g., serially)

V. Microfluidic and Nanofluidic Device

A. Microfluidic and Nanofluidic Device Terms

A "microfluidic device" is a device that includes one or more discrete microfluidic circuits configured to hold a fluid, each circuit comprised of fluidically interconnected circuit elements, including but not limited to region(s), channel(s), chamber(s), and/or pen(s), and at least two ports configured to allow the fluid (and, optionally, micro-objects suspended in the fluid) to flow into and/or out of the microfluidic device. Typically, a microfluidic circuit in a microfluidic device holds a volume of fluid of less than about 1 mL, e.g., less than about 750, 500, 250, 200, 150, 100, 75, 50, 25, 20, 15, 10, 9, 8, 7, 6, 5, 4, 3, or 2 μL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300μ.

A "nanofluidic device" is a type of microfluidic device having a microfluidic circuit that comprises at least one circuit element configured to hold a volume of fluid of less than about 1 μL, e.g., less than about 750, 500, 250, 200, 150, 100, 75, 50, 25, 20, 15, 10, 9, 8, 7, 6, 5, 4, 3, 2, 1 nL or less. Typically, a nanofluidic device will comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements is configured to hold a volume of fluid of about 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A microfluidic (or nanofluidic) device can comprise "swept" regions and "unswept" regions. A swept region is comprised of one or more fluidically interconnected circuit elements of a microfluidic circuit, each of which experiences a flux of fluid when fluid is flowing through the microfluidic circuit. The circuit elements of a swept region can include, for example, regions, channels, and chambers. An unswept region, in contrast, is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region.

The capability of biological micro-objects (e.g., biological cells) to produce specific biological materials (e.g., proteins, metabolites, secretions, etc.) can be assayed in such a microfluidic (or nanofluidic) device. For example, sample material comprising biological micro-objects (such as a T cell, B cell, or NK cell) to be assayed for production of an analyte of interest (such as a cytokine, an antibody, or other secretion) can be loaded into a swept region of the microfluidic device. The flow of fluid through the swept region can then be stopped, and ones of the biological micro-objects in the swept region can be disposed in unswept regions. Depending on the assay being performed, the biological micro-objects that get disposed in the unswept regions can be selected randomly or based on particular characteristics. The remaining sample material can then be flowed out of the swept region and an assay material flowed into the swept region. Because the selected biological micro-objects are in unswept regions, the selected biological micro-objects are not substantially affected (i.e., they remain sequestered in the unswept regions) by the flowing out of the remaining sample material or the flowing in of the assay material. The selected biological micro-objects can be allowed to produce the analyte of interest, which (if secreted) can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest. If the analyte of interest diffuses slowly or remains attached to the biological micro-object, the assay can be modified to include disposing the assay material in the unswept regions and/or by using assay material that diffuses into the unswept regions.

B. System Including a Microfluidic Device

Figure 1C:
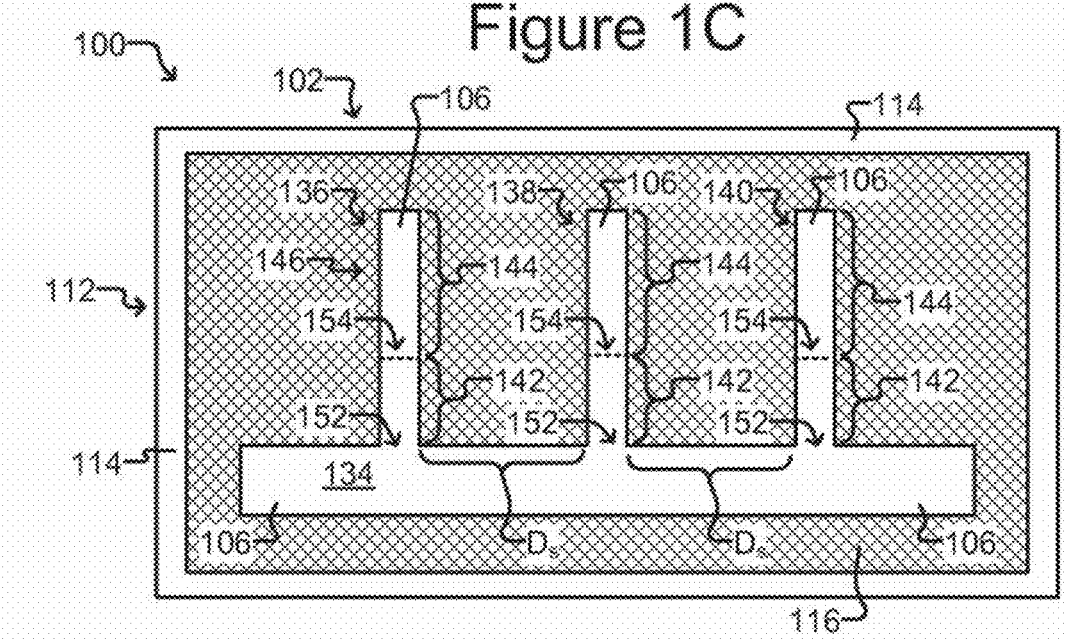
FIG. 1C is a top, cross-sectional view of the microfluidic device of FIG. 1A.

FIGS. 1A-1C illustrate an example of a system having a microfluidic device 100 which may be used in the methods described herein. As shown, the microfluidic device 100 encloses a microfluidic circuit 132 comprising a plurality of interconnected fluidic circuit elements. In the example illustrated in FIGS. 1A-1C, the microfluidic circuit 132 includes a flow channel 134 to which isolation chambers 136, 138, 140 are fluidically connected. Although one flow channel 134 and three isolation chambers 136, 138, 140 are shown in the illustrated embodiment, it should be understood that there may be more than one flow channel 134, and more or fewer than three isolation chambers 136, 138, 140, respectively, in alternate embodiments. The microfluidic circuit 132 can also include additional or different fluidic circuit elements such as fluidic chambers, reservoirs, and the like.

The microfluidic device 100 comprises an enclosure 102 enclosing the microfluidic circuit 132, which can contain one or more fluidic media. Although the device 100 can be physically structured in different ways, in the embodiment shown in FIGS. 1A-1C, the enclosure 102 includes a support structure 104 (e.g., a base), a microfluidic circuit structure 112, and a cover 122. The support structure 104, microfluidic circuit structure 112, and the cover 122 can be attached to each other. For example, the microfluidic circuit structure 112 can be disposed on the support structure 104, and the cover 122 can be disposed over the microfluidic circuit structure 112. With the support structure 104 and the cover 122, the microfluidic circuit structure 112 can define the microfluidic circuit 132. An inner surface of the microfluidic circuit 132 is identified in the figures as 106.

The support structure 104 can be at the bottom and the cover 122 at the top of the device 100 as illustrated in FIGS. 1A and 1B. Alternatively, the support structure 104 and cover 122 can be in other orientations. For example, the support structure 104 can be at the top and the cover 122 at the bottom of the device 100. Regardless of the configuration, one or more fluid access (i.e., ingress and egress) ports 124 are provided, each fluid access port 124 comprising a passage 126 in communication with the microfluidic circuit 132, which allow for a fluid material to be flowed into, or out of, the enclosure 102. The fluid passages 126 may include a valve, a gate, a pass-through hole, or the like. Although two fluid access ports 124 are shown in the illustrated embodiment, it should be understood that alternate embodiments of the device 100 can have only one or more than two fluid access ports 124 providing ingress and egress of fluid material into an out of the microfluidic circuit 132.

The microfluidic circuit structure 112 can define or otherwise accommodate circuit elements of the microfluidic circuit 132, or other types of circuits located within the enclosure 102. In the embodiment illustrated in FIGS. 1A-1C, the microfluidic circuit structure 112 comprises a frame 114 and a microfluidic circuit material 116.

The support structure 104 can comprise a substrate or a plurality of interconnected substrates. For example, the support structure 104 can comprise one or more interconnected semiconductor substrates, printed circuit boards (PCB), or the like, and combinations thereof (e.g. a semiconductor substrate mounted on a PCB). The frame 114 can partially or completely enclose the microfluidic circuit material 116. The frame 114 can be, for example, a relatively rigid structure substantially surrounding the microfluidic circuit material 116. For example the frame 114 can comprise a metal material.

The microfluidic circuit material 116 can be patterned with cavities or the like to define microfluidic circuit elements and interconnections of the microfluidic circuit 132. The microfluidic circuit material 116 can comprise a flexible material (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicon (e.g. photo-patternable silicon), photo-resist (e.g., SU8), or the like. In some embodiments, such materials—and thus the microfluidic circuit material 116—can be rigid and/or substantially impermeable to gas. Regardless of the material(s) used, microfluidic circuit material 116 is disposed on the support structure 104, within the frame 114.

The cover 122 can be an integral part of the frame 114 and/or the microfluidic circuit material 116. Alternatively, the cover 122 can be a structurally distinct element (as illustrated in FIGS. 1A and 1B). The cover 122 can comprise the same or different materials than the frame 114 and/or the microfluidic circuit material 116. Similarly, the support structure 104 can be a separate structure from the frame 114 or microfluidic circuit material 116 as illustrated or an integral part of the frame 114 or microfluidic circuit material 116. Likewise, the frame 114 and microfluidic circuit material 116 can be separate structures as shown in FIGS. 1A-1C or integral portions of the same structure. In some embodiments, the cover or lid 122 is made from a rigid material.

The rigid materials may be glass or the like. In some embodiments, the rigid material may be conductive (e.g. ITO-coated glass) and/or modified to support cell adhesion, viability and/or growth. The modification may include a coating of a synthetic or natural polymer. In some embodiments, a portion of the cover or lid 122 that is positioned over a respective isolation chamber 136, 138, 140 of FIGS. 1A-1C, or the equivalent in the below-described embodiments illustrated in FIGS. 2, 3, and 4, is made of a deformable material, including but not limited to PDMS. Thus, the cover or lid 122 may be a composite structure having both rigid and deformable portions. In some embodiments, the cover 122 and/or the support structure 104 can be transparent to light.

The cover 122 may also include at least one material that is gas permeable, including but not limited to PDMS.

C. Other System Components

FIG. 1A also illustrates simplified block diagram depictions of a control/monitoring system 170 that can be utilized in conjunction with the microfluidic device 100, which together provide a system for identifying B cells that produce antibodies that bind to cancer cells. As shown (schematically), the control/monitoring system 170 includes a control module 172 and control/monitoring equipment 180. The control module 172 can be configured to control and monitor the device 100 directly and/or through the control/monitoring equipment 180.

The control module 172 includes a controller 174 and a memory 176. The controller 174 can be, for example, a digital processor, computer, or the like, and the memory 176 can be, for example, a non-transitory digital memory for storing data and machine executable instructions (e.g., software, firmware, microcode, or the like) as non-transitory data or signals. The controller 174 can be configured to operate in accordance with such machine executable instructions stored in the memory 176. Alternatively, or in addition, the controller 174 can comprise hardwired digital circuitry and/or analog circuitry. The control module 172 can thus be configured to perform (either automatically or based on user-directed input) any process useful in the methods described herein, step of such a process, function, act, or the like discussed herein.

The control/monitoring equipment 180 can comprise any of a number of different types of devices for controlling or monitoring the microfluidic device 100 and processes performed with the microfluidic device 100. For example, the control/monitoring equipment 180 can include power sources (not shown) for providing power to the microfluidic device 100; fluidic media sources (not shown) for providing fluidic media to or removing media from the microfluidic device 100; motive modules such as, by way of example, a selector control module (described below) for controlling selection and movement of micro-objects (not shown) in the microfluidic circuit 132; image capture mechanisms such as, by way of example, a detector (described below) for capturing images (e.g., of micro-objects) inside the microfluidic circuit 132; stimulation mechanisms such as, by way of example, light source 320 of the embodiment illustrated in FIG. 1D, for directing energy into the microfluidic circuit 132 to stimulate reactions; and the like.

Figure 4A:
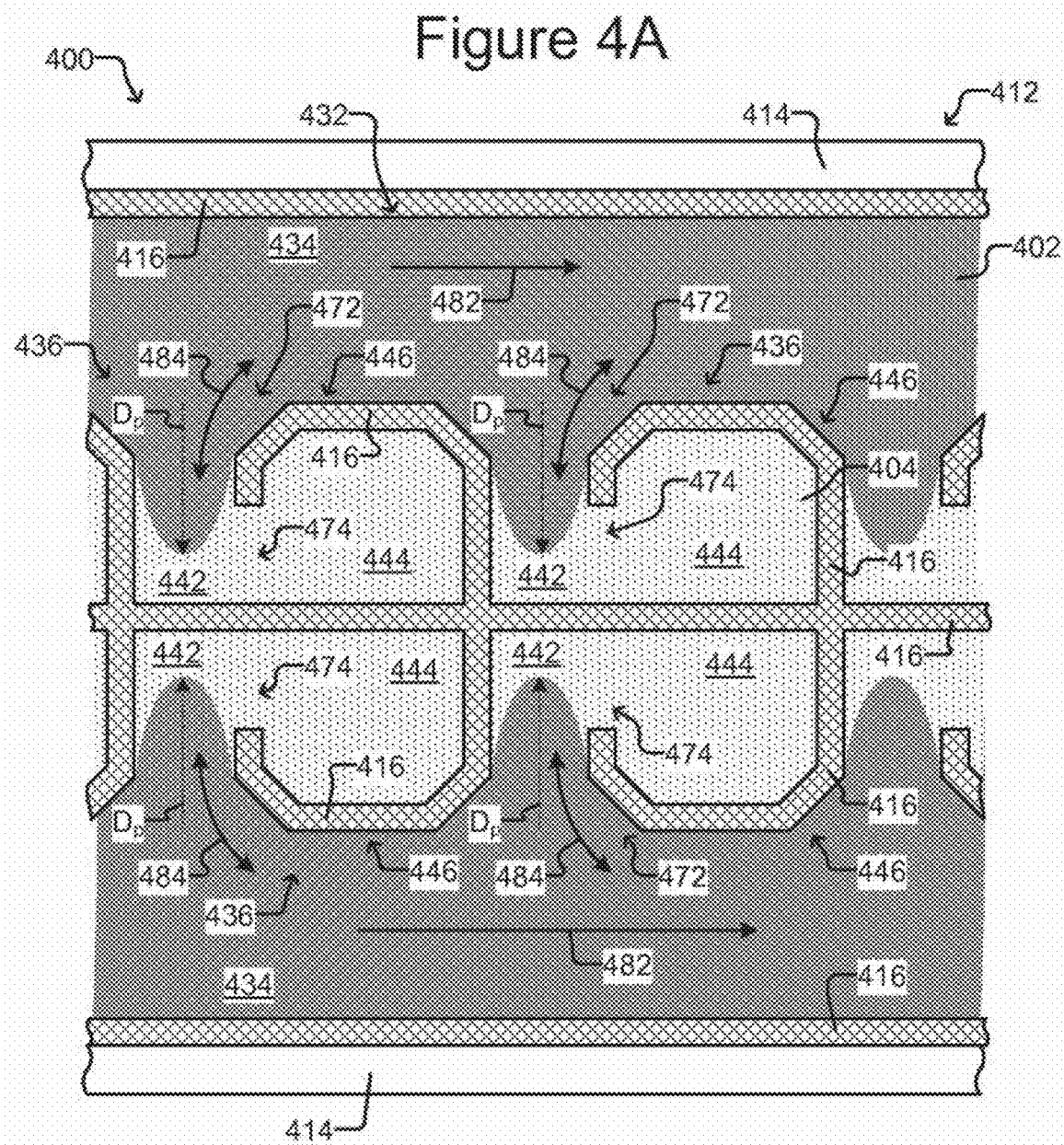
FIGS. 4A-4C show another example of a portion of a microfluidic device having a flow channel and an isolation chamber.
Figure 4B:
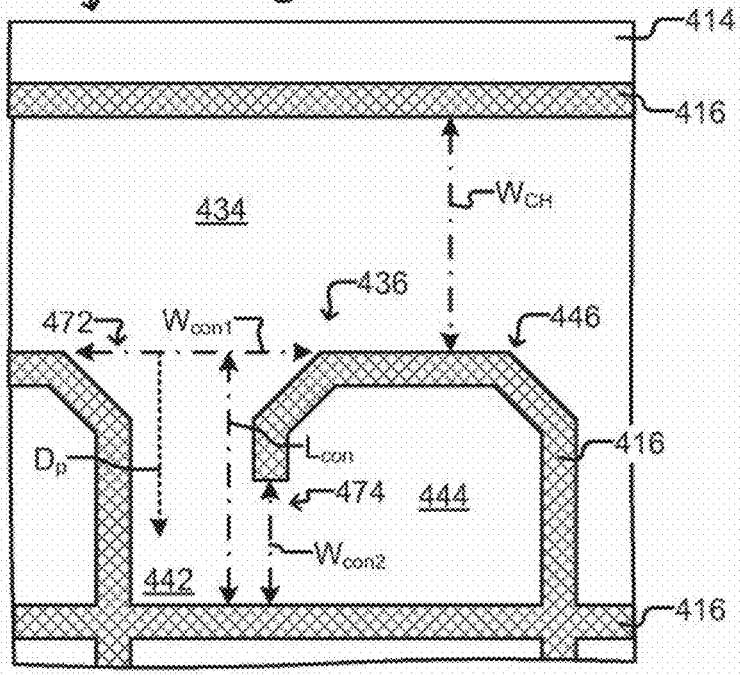
Figure 4C:
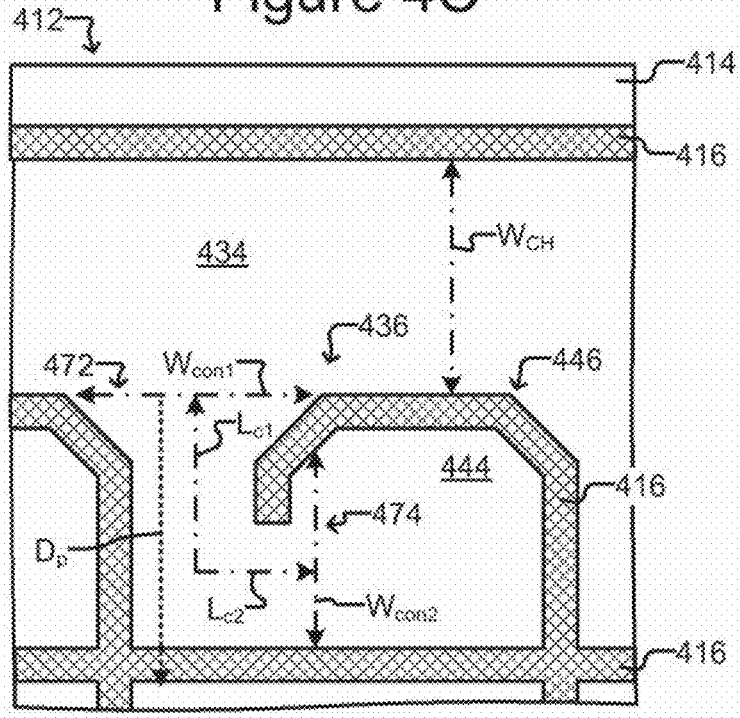

More particularly, an image capture detector can include one or more image capture devices and/or mechanisms for detecting events in the flow regions, including but not limited to flow channel 134 of the embodiments shown in FIGS. 1A-1C, 2, and 3, flow channel 434 of the embodiment shown in FIGS. 4A-4C, and flow region 240 of the embodiment shown in FIG. 1D-1E, and/or the isolation chambers of the respective illustrated microfluidic devices 100, 300, and 400, including micro-objects contained in a fluidic medium occupying the respective flow regions and/or isolation chambers. For example, the detector can comprise a photodetector capable of detecting one or more radiation characteristics (e.g., due to fluorescence or luminescence) of a micro-object (not shown) in the fluidic medium. Such a detector can be configured to detect, for example, that one or more micro-objects (not shown) in the medium are radiating electromagnetic radiation and/or the approximate wavelength, brightness, intensity, or the like of the radiation. The detector may capture images under visible, infrared, or ultraviolet wavelengths of light. Examples of suitable photodetectors include without limitation photomultiplier tube detectors and avalanche photodetectors.

Examples of suitable imaging devices that the detector can comprise include digital cameras or photosensors such as charge coupled devices and complementary metal-oxide-semiconductor (CMOS) imagers. Images can be captured with such devices and analyzed (e.g., by the control module 172 and/or a human operator).

A flow controller can be configured to control a flow of the fluidic medium in the flow regions/swept regions/channels of the respective illustrated microfluidic devices 100, 300, and 400. For example, the flow controller can control the direction and/or velocity of the flow. Examples of such flow control elements of the flow controller include one or more pumps or fluid actuators. In some embodiments, the flow controller can include additional elements such as one or more sensors for sensing, for example, the velocity of the flow and/or the pH of the medium in the flow region/swept region/channel.

The control module 172 can be configured to receive signals from and control the selector control module, the detector, and/or the flow controller.

Referring in particular to the embodiment shown in FIG. 1D, a light source 320 may direct light useful for illumination and/or fluorescent excitation into the microfluidic circuit 132. Alternatively, or in addition the light source may direct energy into the microfluidic circuit 132 to stimulate reactions which include providing activation energy needed for DEP configured microfluidic devices to select and move micro-objects. The light source may be any suitable light source capable of projecting light energy into the microfluidic circuit 132, such as a high pressure Mercury lamp, Xenon arc lamp, diode, laser or the like. The diode may be an LED. In one example the LED may be a broad spectrum "white" light LED (e.g. a UHP-T-LED-White by Prizmatix). The light source may include a projector or other device for generating structured light, such as a digital micromirror device (DMD), a MSA (microarray system) or a laser.

D. Motive Modules for Selecting and Moving Micro-Objects Including Biological Cells As described above, the control/monitoring equipment 180 can comprise motive modules for selecting and moving micro-objects (not shown) in the microfluidic circuit 132. A variety of motive mechanisms can be utilized. For example, dielectrophoresis (DEP) mechanisms can be utilized to select and move micro-objects (not shown) in the microfluidic circuit. The support structure 104 and/or cover 122 of the microfluidic device 100 of FIGS. 1A-1C can comprise DEP configurations for selectively inducing DEP forces on micro-objects (not shown) in a fluidic medium (not shown) in the microfluidic circuit 132 and thereby select, capture, and/or move individual micro-objects. The control/monitoring equipment 180 can include one or more control modules for such DEP configurations. Micro-objects, including cells, may alternatively be moved within the microfluidic circuit or exported from the microfluidic circuit using gravity, magnetic force, fluid flow, and/or the like.

One example of a microfluidic device having a DEP configuration that comprises support structure 104 and cover 122 is the microfluidic device 300 illustrated in FIGS. 1D and 1E. While for purposes of simplicity FIGS. 1D and 1E show a side cross-sectional view and a top cross-sectional view of a portion of a flow region 240 of the microfluidic device 300, it should be understood that the microfluidic device 300 may also include one or more isolation chambers, as well as one or more additional flow regions/channels, such as those described herein with respect to microfluidic devices 100 and 400, and that a DEP configuration may be incorporated in any of such regions of the microfluidic device 300. It should be further appreciated that any of the above or below described microfluidic system components may be incorporated in and/or used in combination with microfluidic device 300. For example, a control module 172 including control/monitoring equipment 180 described above in conjunction with microfluidic device 100 of FIGS. 1A-1C may also be used with the microfluidic device 300, including one or more of an image-capture detector, flow controller, and selector control module.

As seen in FIG. 1D, the microfluidic device 300 includes a first electrode 304, a second electrode 310 spaced apart from the first electrode 304, and an electrode activation substrate 308 overlying electrode 310. The respective first electrode 304 and electrode activation substrate 308 define opposing surfaces of the flow region 240, wherein a medium 202 contained in the flow region 240 provides a resistive flow path between electrode 304 and the electrode activation substrate 308. A power source 312 configured to be connected to the first electrode 304 and the second electrode 310 and create a biasing voltage between the electrodes, as required for the generation of DEP forces in the flow region 240, is also shown. The power source 312 can be, for example, an alternating current (AC) power source.

In certain embodiments, the microfluidic device 300 illustrated in FIGS. 1D and 1E can have an optically-actuated DEP configuration, such as an Opto-Electronic Tweezer (OET) configuration. In such embodiments, changing patterns of light 322 from the light source 320, which may be controlled by the selector control module, can be used to selectively activate changing patterns of "DEP electrodes" on targeted locations 314 on the inner surface 242 of the flow region 240. Hereinafter the targeted regions 314 on the inner surface 242 of the flow region 240 are referred to as "DEP electrode regions."

In the example illustrated in FIG. 1E, a light pattern 322' directed onto the inner surface 242 illuminates the cross-hatched DEP electrode regions 314a in the square pattern shown. The other DEP electrode regions 314 are not illuminated and are hereinafter referred to as "dark" DEP electrode regions 314. The electrical impedance through the DEP electrode activation substrate 308 (i.e., from each dark electrode region 314 on the inner surface 242 to the second electrode 310) is greater than the electrical impedance through the medium 202 (i.e., from the first electrode 304, across the medium 202 in the flow region 240, to the dark DEP electrode regions 314 on the inner surface 242). Illuminating the DEP electrode regions 314a, however, reduces the impedance through the electrode activation substrate 308 (i.e., from the illuminated DEP electrode regions 314a on the inner surface 242 to the second electrode 310) to less than the impedance through the medium 202 (i.e., from the first electrode 304, across the medium 202 in the flow region 240, to the illuminated DEP electrode regions 314a on the inner surface 242).

With the power source 312 activated, the foregoing creates an electric field gradient in the medium 202 between the respective illuminated DEP electrode regions 314a and adjacent dark DEP electrode regions 314, which in turn creates localized DEP forces that attract or repel nearby micro-objects (not shown) in the fluid medium 202. In this manner, DEP electrodes that attract or repel micro-objects in the medium 202 can be selectively activated and deactivated in order to manipulate, i.e., move, the micro-objects within the flow region 240 by changing the light patterns 322 projected from the light source 320 into the microfluidic device 300. The light source 320 can be, for example, a laser or other type of structured light source, such as a projector. Whether the DEP forces attract or repel nearby micro-objects can depend on parameters such as, without limitation, the frequency of the power source 312 and the dielectric properties of the medium 202 and/or micro-objects (not shown).

The square pattern 322' of illuminated DEP electrode regions 314a illustrated in FIG. 1E is an example only. Any number of patterns or configurations of DEP electrode regions 314 can be selectively illuminated by a corresponding pattern of light 322 projected from the source 320 into the device 300, and the pattern of illuminated DEP electrode regions 322' can be repeatedly changed by changing the light pattern 322 in order to manipulate micro-objects in the fluid medium 202.

In some embodiments, the electrode activation substrate 308 can be a photoconductive material, and the rest of the inner surface 242 can be featureless. For example, the photoconductive material can be made from amorphous silicon, and can form a layer having a thickness of about 500 nm to about 2 µm in thickness (e.g. substantially 1 micron in thickness). In such embodiments, the DEP electrode regions 314 can be created anywhere and in any pattern on the inner surface 242 of the flow region 240 in accordance with the light pattern 322 (e.g., light pattern 322' shown in FIG. 1E). The number and pattern of the illuminated DEP electrode regions 314a are thus not fixed, but correspond to the respective projected light patterns 322. Examples are illustrated in U.S. Pat. No. 7,612,355, in which un-doped amorphous silicon material is used as an example of photoconductive material that can compose the electrode activation substrate 308.

In other embodiments, the electrode activation substrate 308 can comprise a substrate comprising a plurality of doped layers, electrically insulating layers, and electrically conductive layers that form semiconductor integrated circuits such as is known in semiconductor fields. For example, the electrode activation substrate 308 can comprise an array of photo-transistors. In such embodiments, electric circuit elements can form electrical connections between the DEP electrode regions 314 at the inner surface 242 of the flow region 240 and the second electrode 310 that can be selectively activated by the respective light patterns 322. When not activated, the electrical impedance through each electrical connection (i.e., from a corresponding DEP electrode region 314 on the inner surface 242, through the electrical connection, to the second electrode 310) can be greater than the impedance through the medium 202 (i.e., from the first electrode 304, through the medium 202, to the corresponding DEP electrode region 314 on the inner surface 242). When activated by light in the light pattern 322, however, the electrical impedance though the illuminated electrical connections (i.e., from each illuminated DEP electrode region 314a, through the electrical connection, to the second electrode 310) can be reduced to an amount less than the electrical impedance through the medium 202 (i.e., from the first electrode 304, through the medium 202, to the corresponding illuminated DEP electrode region 314a), thereby activating a DEP electrode at the corresponding DEP electrode region 314 as discussed above. DEP electrodes that attract or repel micro-objects (not shown) in the medium 202 can thus be selectively activated and deactivated at many different DEP electrode regions 314 at the inner surface 242 of the flow region 240 by the light pattern 322. Examples of such configurations of the electrode activation substrate 308 include the phototransistor-based device 300 illustrated in FIGS. 21 and 22 of U.S. Pat. No. 7,956,339.

In other embodiments, the electrode activation substrate 308 can comprise a substrate comprising a plurality of electrodes, which may be either photo-actuated. Examples of such configurations of the electrode activation substrate 308 include the photo-actuated devices 200, 400, 500, and 600 illustrated and described in U.S. Patent Application Publication No. 2014/0124370. In still other embodiments, a DEP configuration of the support structure 104 and/or cover 122 does not rely upon light activation of DEP electrodes at the inner surface of the microfluidic device, but uses selectively addressable and energizable electrodes positioned opposite to a surface including at least one electrode, such as described in U.S. Pat. No. 6,942,776.

In some embodiments of a DEP configured device, the first electrode 304 can be part of a first wall 302 (or cover) of the housing 102, and the electrode activation substrate 308 and second electrode 310 can be part of a second wall 306 (or base) of the housing 102, generally as illustrated in FIG. 1D. As shown, the flow region 240 can be between the first wall 302 and the second wall 306. The foregoing, however, is but an example. In alternative embodiments, the first electrode 304 can be part of the second wall 306 and one or both of the electrode activation substrate 308 and/or the second electrode 310 can be part of the first wall 302. Moreover, the light source 320 can alternatively be located underneath the housing 102. In certain embodiments, the first electrode 304 may be an indium-tin-oxide (ITO) electrode, though other materials may also be used.

When used with the optically-actuated DEP configurations of microfluidic device 300 of FIGS. 1D-1E, a selector control module can thus select a micro-object (not shown) in the medium 202 in the flow region 240 by projecting one or more consecutive light patterns 322 into the device 300 to activate a corresponding one or more DEP electrodes at DEP electrode regions 314 of the inner surface 242 of the flow region 240 in successive patterns that surround and "capture" the micro-object. The selector control module can then move the captured micro-object within the flow region 240 by moving the light pattern 322 relative to the device 300 (or the device 300 (and thus the captured micro-object therein) can be moved relative to the light source 320 and/or light pattern 322). For embodiments featuring electrically-actuated DEP configurations of microfluidic device 300, the selector control module can select a micro-object (not shown) in the medium 202 in the flow region 240 by electrically activating a subset of DEP electrodes at DEP electrode regions 314 of the inner surface 242 of the flow region 240 that form a pattern that surrounds and "captures" the micro-object. The selector control module can then move the captured micro-object within the flow region 240 by changing the subset of DEP electrodes that are being electrically activated.

E. Isolation Chamber Configurations

Examples of isolation chambers 136, 138, and 140 of device 100 are shown in FIGS. 1A-1C. With specific reference to FIG. 1C, each isolation chamber 136, 138, 140 comprises an isolation structure 146 defining an isolation region 144 and a connection region 142 that fluidically connects the isolation region 144 to the flow channel 134. The connection regions 142 each have a proximal opening 152 into the flow channel 134, and a distal opening 154 into the respective isolation region 144. The connection regions 142 are preferably configured so that a maximum penetration depth of a flow of a fluidic medium (not shown) flowing at a maximum velocity (Vmax) in the flow channel 134 does not inadvertently extend into the isolation region 144. A micro-object (not shown) or other material (not shown) disposed in an isolation region 144 of a respective isolation chamber 136, 138, 140 can thus be isolated from, and not substantially affected by, a flow of medium (not shown) in the flow channel 134. The flow channel 134 can thus be an example of a swept region, and the isolation regions of the isolation chambers 136, 138, 140 can be examples of unswept regions. As noted above, the respective flow channel 134 and isolation chambers 136, 138, 140 are configured to contain one or more fluidic media (not shown). In the embodiment shown in FIGS. 1A-1C, the fluid access ports 124 are fluidly connected to the flow channel 134 and allow a fluidic medium (not shown) to be introduced into or removed from the microfluidic circuit 132. Once the microfluidic circuit 132 contains a fluidic medium, flows of specific fluidic media therein can be selectively generated in the flow channel 134. For example, a flow of a medium can be created from one fluid access port 124 functioning as an inlet to another fluid access port 124 functioning as an outlet.

In some modes, the microfluidic isolation regions may each form a dead-end in the microfluidic device. In some aspects, when the flow region and the microfluidic isolation regions are substantially filled with fluidic media: (a) components of the second medium are able to diffuse into the first medium or components of the first medium are able to diffuse into the second medium; and (b) there is substantially no flow of the first medium from the flow region into the isolation region.

FIG. 2 illustrates a detailed view of an example of an isolation chamber 136 of the device 100 of FIGS. 1A-1C. Isolation chambers 138, 140 can be configured similarly. Examples of micro-objects 222 located in isolation chamber 136 are also shown.

As is known, a flow of fluidic medium 202 (indicated by directional arrow 212) in the microfluidic flow channel 134 past a proximal opening 152 of the isolation chamber 136 can cause a secondary flow of the medium 202 (indicated by directional arrow 214) into and/or out of the isolation chamber 136. To isolate the micro-objects 222 in the isolation region 144 of the isolation chamber 136 from the secondary flow 214, the length Lcon of the connection region 142 from the proximal opening 152 to the distal opening 154 is preferably greater than a maximum penetration depth Dp of the secondary flow 214 into the connection region 142 when the velocity of the flow 212 in the flow channel 134 is at a maximum (Vmax). As long as the flow 212 in the flow channel 134 does not exceed the maximum velocity Vmax, the flow 212 and resulting secondary flow 214 are limited to the respective flow channel 134 and connection region 142, and kept out of the isolation region 144 of the isolation chamber 136. The flow 212 in the flow channel 134 will thus not draw micro-objects 222 out of the isolation region 144 of isolation chamber 136.

Moreover, the flow 212 will not move miscellaneous particles (e.g., microparticles and/or nanoparticles) that may be located in the flow channel 134 into the isolation region 144 of the isolation chamber 136. Having the length Lcon of the connection region 142 be greater than the maximum penetration depth Dp can thus prevent contamination of the isolation chamber 136 with miscellaneous particles from the flow channel 134 or from another isolation chamber 138, 140.

Because the flow channel 134 and the connection regions 142 of the isolation chambers 136, 138, 140 can be affected by the flow 212 of medium 202 in the flow channel 134, the flow channel 134 and connection regions 142 can be deemed swept (or flow) regions of the microfluidic circuit 132. The isolation regions 144 of the isolation chambers 136, 138, 140, on the other hand, can be deemed unswept (or non-flow) regions. For example, components (not shown) in a first medium 202 in the flow channel 134 can mix with a second medium 204 in the isolation region 144 substantially only by diffusion of the components of the first medium 202 from the flow channel 134 through the connection region 142 and into the second medium 204 in the isolation region 144. Similarly, components of the second medium 204 (not shown) in the isolation region 144 can mix with the first medium 202 in the flow channel 134 substantially only by diffusion of the components of the second medium 204 from the isolation region 144 through the connection region 142 and into the first medium 202 in the flow channel 134. It should be appreciated that the first medium 202 can be the same medium or a different medium than the second medium 204. Moreover, the first medium 202 and the second medium 204 can start out being the same, then become different, e.g., through conditioning of the second medium by one or more cells in the isolation region 144, or by changing the medium flowing through the flow channel 134.

The maximum penetration depth Dp of the secondary flow 214 caused by the flow 212 in the flow channel 134 can depend on a number of parameters. Examples of such parameters include (without limitation) the shape of the flow channel 134 (e.g., the flow channel can direct medium into the connection region 142, divert medium away from the connection region 142, or simply flow past the connection region 142); a width Wch (or cross-sectional area) of the flow channel 134 at the proximal opening 152; a width Wcon (or cross-sectional area) of the connection region 142 at the proximal opening 152; the maximum velocity Vmax of the flow 212 in the flow channel 134; the viscosity of the first medium 202 and/or the second medium 204, and the like.

In some embodiments, the dimensions of the flow channel 134 and/or isolation chambers 136, 138, 140 are oriented as follows with respect to the flow 212 in the flow channel 134: the flow channel width Wch (or cross-sectional area of the flow channel 134) can be substantially perpendicular to the flow 212; the width Wcon (or cross-sectional area) of the connection region 142 at the proximal opening 152 can be substantially parallel to the flow 212; and the length Lcon of the connection region can be substantially perpendicular to the flow 212. The foregoing are examples only, and the dimensions of the flow channel 134 and isolation chambers 136, 138, 140 can be in additional and/or further orientations with respect to each other.

As illustrated in FIG. 2, the width Wcon of the connection region 142 can be uniform from the proximal opening 152 to the distal opening 154. The width Wcon of the connection region 142 at the distal opening 154 can thus be in any of the below-identified ranges corresponding to the width Wcon of the connection region 142 at the proximal opening 152. Alternatively, the width Wcon of the connection region 142 at the distal opening 154 can be larger (e.g., as shown in the embodiment of FIG. 3) or smaller (e.g., as shown in the embodiment of FIGS. 4A-4C) than the width Wcon of the connection region 142 at the proximal opening 152.

As also illustrated in FIG. 2, the width of the isolation region 144 at the distal opening 154 can be substantially the same as the width Wcon of the connection region 142 at the proximal opening 152. The width of the isolation region 144 at the distal opening 154 can thus be in any of the below-identified ranges corresponding to the width Wcon of the connection region 142 at the proximal opening 152. Alternatively, the width of the isolation region 144 at the distal opening 154 can be larger (e.g., as shown in FIG. 3) or smaller (not shown) than the width Wcon of the connection region 142 at the proximal opening 152.

In some embodiments, the maximum velocity Vmax of a flow 212 in the flow channel 134 is substantially the same as the maximum velocity that the flow channel 134 can maintain without causing a structural failure in the respective microfluidic device (e.g., device 100) in which the flow channel is located. In general, the maximum velocity that a flow channel can maintain depends on various factors, including the structural integrity of the microfluidic device and the cross-sectional area of the flow channel. For the exemplary microfluidic devices disclosed and described herein, a maximum flow velocity Vmax in a flow channel having a cross-sectional area of about 3,500 to 10,000 square microns, is about 1.5 to 15 OL/sec. Alternatively, the maximum velocity Vmax of a flow in a flow channel can be set so as to ensure that isolation regions are isolated from the flow in the flow channel. In particular, based on the width Wcon of the proximal opening of a connection region of a growth chamber, Vmax can be set so as to ensure that the depth of penetration Dp of a secondary flow into the connection region is less than Lcon. For example, for a growth chamber having a connection region with a proximal opening having a width Wcon of about 40 to 50 microns and Lcon of about 50 to 100 microns, Vmax can be set at or about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 4/sec.

In some embodiments, the sum of the length Lcon of the connection region 142 and a corresponding length of the isolation region 144 of an isolation chamber 136, 138, 140 can be sufficiently short for relatively rapid diffusion of components of a second medium 204 contained in the isolation region 144 to a first medium 202 flowing or otherwise contained in the flow channel 134. For example, in some embodiments, the sum of (1) the length Lcon of the connection region 142 and (2) the distance between a biological micro-object located in isolation region 144 of an isolation chamber 136, 138, 140 and the distal opening 154 of the connection region can be one of the following ranges: from about 40 microns to 500 microns, 50 microns to 450 microns, 60 microns to 400 microns, 70 microns to 350 microns, 80 microns to 300 microns, 90 microns to 250 microns, 100 microns to 200 microns, or any range including one of the foregoing end points. The rate of diffusion of a molecule (e.g., an analyte of interest, such as an antibody) is dependent on a number of factors, including (without limitation) temperature, viscosity of the medium, and the coefficient of diffusion DO of the molecule. For example, the DO for an IgG antibody in aqueous solution at about 20° C. is about $4.4 \times 10^{-7}$ cm2/sec, while the kinematic viscosity of cell culture medium is about $9 \times 10^{-4}$ m2/sec. Thus, an antibody in cell culture medium at about 20° C. can have a rate of diffusion of about 0.5 microns/sec. Accordingly, in some embodiments, a time period for diffusion from a biological micro-object located in isolation region 144 into the flow channel 134 can be about 10 minutes or less (e.g., about 9, 8, 7, 6, 5 minutes, or less). The time period for diffusion can be manipulated by changing parameters that influence the rate of diffusion. For example, the temperature of the media can be increased (e.g., to a physiological temperature such as about 37° C.) or decreased (e.g., to about 15° C., 10° C., or 4° C.) thereby increasing or decreasing the rate of diffusion, respectively. Alternatively, or in addition, the concentrations of solutes in the medium can be increased or decreased.

The physical configuration of the isolation chamber 136 illustrated in FIG. 2 is but an example, and many other configurations and variations for isolation chambers are possible. For example, the isolation region 144 is illustrated as sized to contain a plurality of micro-objects 222, but the isolation region 144 can be sized to contain only about one, two, three, four, five, or similar relatively small numbers of micro-objects 222. Accordingly, the volume of an isolation region 144 can be, for example, at least about $3 \times 10^3$, $6 \times 10^3$, $9 \times 10^3$, $1 \times 10^4$, $2 \times 10^4$, $4 \times 10^4$, $8 \times 10^4$, $1 \times 10^5$, $2 \times 10^5$, $4 \times 10^5$, $8 \times 10^5$, $1 \times 10^6$, $2 \times 10^6$, $4 \times 10^6$, $6 \times 10^6$ cubic microns, or more.

As another example, the isolation chamber 136 is shown in FIG. 2 as extending generally perpendicularly from the flow channel 134 and thus forming generally about 90° angles with the flow channel 134. The isolation chamber 136 can alternatively extend from the flow channel 134 at other angles such as, for example, any angle from about 30° to about 150°.

As yet another example, the connection region 142 and the isolation region 144 are illustrated in FIG. 2 as having a substantially rectangular configuration, but one or both of the connection region 142 and the isolation region 144 can have a different configuration, including (without limitation) oval, triangular, circular, hourglass-shaped, and the like.

As still another example, the connection region 142 and the isolation region 144 are illustrated in FIG. 2 as having substantially uniform widths. That is, the width Wcon of the connection region 142 is shown as being uniform along the entire length Lcon from the proximal opening 152 to the distal opening 154. A corresponding width of the isolation region 144 is similarly uniform; and the width Wcon of the connection region 142 and a corresponding width of the isolation region 144 are shown as equal. However, in alternate embodiments, any of the foregoing can be different. For example, a width Wcon of the connection region 142 can vary along the length Lcon, from the proximal opening 152 to the distal opening 154, e.g., in the manner of a trapezoid, or of an hourglass; a width of the isolation region 144 can also vary along the length Lcon, e.g., in the manner of a triangle, or of a flask; and a width Wcon of the connection region 142 can be different than a width of the isolation region 144.

FIG. 3 illustrates an alternate embodiment of an isolation chamber 336, demonstrating some examples of the foregoing variations. While the alternative isolation chamber 336 is described as a replacement for chamber 136 in the microfluidic device 100, it should be appreciated that the isolation chamber 336 can replace any of isolation chambers in any of the microfluidic device embodiments disclosed or described herein. Furthermore, there may be one isolation chamber 336 or a plurality of isolation chambers 336 provided in a given microfluidic device.

The isolation chamber 336 includes a connection region 342 and an isolation structure 346 comprising an isolation region 344. The connection region 342 has a proximal opening 352 to the flow channel 134 and a distal opening 354 to the isolation region 344. In the embodiment illustrated in FIG. 3, the connection region 342 expands such that its width Wcon increases along a length of the connection region Lcon, from the proximal opening 352 to the distal opening 354. Other than having a different shape, however, the connection region 342, isolation structure 346, and isolation region 344 function generally the same as the above-described connection region 142, isolation structure 146, and isolation region 144 of isolation chamber 136 shown in FIG. 2.

For example, the flow channel 134 and the isolation chamber 336 can be configured so that the maximum penetration depth Dp of the secondary flow 214 extends into the connection region 342, but not into the isolation region 344. The length Lcon of the connection region 342 can thus be greater than the maximum penetration depth Dp, generally as discussed above with respect to the connection regions 142 shown in FIG. 2. Also, as discussed above, micro-objects 222 in the isolation region 344 will stay in the isolation region 344 as long as the velocity of the flow 212 in the flow channel 134 does not exceed the maximum flow velocity Vmax. The flow channel 134 and connection region 342 are thus examples of swept (or flow) regions, and the isolation region 344 is an example of an unswept (or non-flow) region.

FIGS. 4A-C depict another exemplary embodiment of a microfluidic device 400 containing a microfluidic circuit 432 and flow channels 434, which are variations of the respective microfluidic device 100, circuit 132 and flow channel 134 of FIGS. 1A-1C. The microfluidic device 400 also has a plurality of growth chambers 436 that are additional variations of the above-described growth chambers 136, 138, 140 and 336. In particular, it should be appreciated that the growth chambers 436 of device 400 shown in FIGS. 4A-C can replace any of the above-described growth chambers 136, 138, 140, 336 in devices 100 and 300. Likewise, the microfluidic device 400 is another variant of the microfluidic device 100, and may also have the same or a different DEP configuration as the above-described microfluidic device 300, as well as any of the other microfluidic system components described herein.

The microfluidic device 400 of FIGS. 4A-C comprises a support structure (not visible in FIGS. 4A-C, but can be the same or generally similar to the support structure 104 of device 100 depicted in FIGS. 1A-1C), a microfluidic circuit structure 412, and a cover (not visible in FIGS. 4A-C, but can be the same or generally similar to the cover 122 of device 100 depicted in FIGS. 1A-1C). The microfluidic circuit structure 412 includes a frame 414 and microfluidic circuit material 416, which can be the same as or generally similar to the frame 114 and microfluidic circuit material 116 of device 100 shown in FIGS. 1A-1C. As shown in FIG. 4A, the microfluidic circuit 432 defined by the microfluidic circuit material 416 can comprise multiple flow channels 434 (two are shown but there can be more) to which multiple growth chambers 436 are fluidically connected.

Each growth chamber 436 can comprise an isolation structure 446, an isolation region 444 within the isolation structure 446, and a connection region 442. From a proximal opening 472 at the flow channel 434 to a distal opening 474 at the isolation structure 436, the connection region 442 fluidically connects the flow channel 434 to the isolation region 444. Generally, in accordance with the above discussion of FIG. 2, a flow 482 of a first fluidic medium 402 in a flow channel 434 can create secondary flows 484 of the first medium 402 from the flow channel 434 into and/or out of the respective connection regions 442 of the growth chambers 436.

As illustrated in FIG. 4B, the connection region 442 of each growth chamber 436 generally includes the area extending between the proximal opening 472 to a flow channel 434 and the distal opening 474 to an isolation structure 446. The length Lcon of the connection region 442 can be greater than the maximum penetration depth Dp of secondary flow 484, in which case the secondary flow 484 will extend into the connection region 442 without being redirected toward the isolation region 444 (as shown in FIG. 4A). Alternatively, at illustrated in FIG. 4C, the connection region 442 can have a length Lcon that is less than the maximum penetration depth Dp, in which case the secondary flow 484 will extend through the connection region 442 and be redirected toward the isolation region 444. In this latter situation, the sum of lengths Lc1 and Lc2 of connection region 442 is greater than the maximum penetration depth Dp, so that secondary flow 484 will not extend into isolation region 444. Whether length Lcon of connection region 442 is greater than the penetration depth Dp, or the sum of lengths Lc1 and Lc2 of connection region 442 is greater than the penetration depth Dp, a flow 482 of a first medium 402 in flow channel 434 that does not exceed a maximum velocity Vmax will produce a secondary flow having a penetration depth Dp, and micro-objects (not shown but can be the same or generally similar to the micro-objects 222 shown in FIG. 2) in the isolation region 444 of a growth chamber 436 will not be drawn out of the isolation region 444 by a flow 482 of first medium 402 in flow channel 434. Nor will the flow 482 in flow channel 434 draw miscellaneous materials (not shown) from flow channel 434 into the isolation region 444 of a growth chamber 436. As such, diffusion is the only mechanism by which components in a first medium 402 in the flow channel 434 can move from the flow channel 434 into a second medium 404 in an isolation region 444 of a growth chamber 436. Likewise, diffusion is the only mechanism by which components in a second medium 404 in an isolation region 444 of a growth chamber 436 can move from the isolation region 444 to a first medium 402 in the flow channel 434. The first medium 402 can be the same medium as the second medium 404, or the first medium 402 can be a different medium than the second medium 404. Alternatively, the first medium 402 and the second medium 404 can start out being the same, then become different, e.g., through conditioning of the second medium by one or more cells in the isolation region 444, or by changing the medium flowing through the flow channel 434.

As illustrated in FIG. 4B, the width Wch of the flow channels 434 (i.e., taken transverse to the direction of a fluid medium flow through the flow channel indicated by arrows 482 in FIG. 4A) in the flow channel 434 can be substantially perpendicular to a width Wcon1 of the proximal opening 472 and thus substantially parallel to a width Wcon2 of the distal opening 474. The width Wcon1 of the proximal opening 472 and the width Wcon2 of the distal opening 474, however, need not be substantially perpendicular to each other. For example, an angle between an axis (not shown) on which the width Wcon1 of the proximal opening 472 is oriented and another axis on which the width Wcon2 of the distal opening 474 is oriented can be other than perpendicular and thus other than 90°. Examples of alternatively angles include angles in any of the following ranges: from about 30° to about 90°, from about 45° to about 90°, from about 60° to about 90°, or the like.

In various embodiments of growth chambers 136, 138, 140, 336, or 436, the isolation region of the growth chamber may have a volume configured to support no more than about $1\times10^3$, $5\times10^2$, $4\times10^2$, $3\times10^2$, $2\times10^2$, $1\times10^2$, 50, 25, 15, or 10 cells in culture. In other embodiments, the isolation region of the growth chamber has a volume to support up to and including about $1\times10^3$, $1\times10^4$, or $1\times10^5$ cells.

In various embodiments of isolation chambers 136, 138, 140, 336, or 436, the isolation region of the isolation chamber may have a volume configured to support no more than about $1\times10^3$, $5\times10^2$, $4\times10^2$, $3\times10^2$, $2\times10^2$, $1\times10^2$, 50, 25, 15, or 10 cells in culture. In other embodiments, the isolation region of the isolation chamber has a volume to support up to and including about $1\times10^3$, $1\times10^4$, or $1\times10^5$ cells.

In various embodiments of isolation chambers 136, 138, 140, 336, or 436, the width Wch of the flow channel 134 at a proximal opening 152 (isolation chambers 136, 138, or 14); the width Wch of the flow channel 134 at a proximal opening 352 (isolation chambers 336); or the width Wch of the flow channel 434 at a proximal opening 472 (isolation chambers 436) can be any of the following ranges: from about 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. The foregoing are examples only, and the width Wch of the flow channel 134 or 434 can be in other ranges (e.g., a range defined by any of the endpoints listed above).

In various embodiments of isolation chambers 136, 138, 140, 336, or 436, the height Hch of the flow channel 134 at a proximal opening 152 (isolation chambers 136, 138, or 140), the flow channel 134 at a proximal opening 352 (isolation chambers 336), or the flow channel 434 at a proximal opening 472 (isolation chambers 436) can be any of the following ranges: from about 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height Hch of the flow channel 134 or 434 can be in other ranges (e.g., a range defined by any of the endpoints listed above).

In various embodiments of isolation chambers 136, 138, 140, 336, or 436, a cross-sectional area of the flow channel 134 at a proximal opening 152 (isolation chambers 136, 138, or 140), the flow channel 134 at a proximal opening 352 (isolation chambers 336), or the flow channel 434 at a proximal opening 472 (isolation chambers 436) can be any of the following ranges: from about 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the flow channel 134 at a proximal opening 152, the flow channel 134 at a proximal opening 352, or the flow channel 434 at a proximal opening 472 can be in other ranges (e.g., a range defined by any of the endpoints listed above).

In various embodiments of isolation chambers 136, 138, 140, 336, or 436, the length of the connection region Lcon can be any of the following ranges: from about 1-200 microns, 5-150 microns, 10-100 microns, 15-80 microns, 20-60 microns, 20-500 microns, 40-400 microns, 60-300 microns, 80-200 microns, and 100-150 microns. The foregoing are examples only, and length Lcon of a connection region 142 (isolation chambers 136, 138, or 140), connection region 342 (isolation chambers 336), or connection region 442 (isolation chambers 436) can be in a different ranges than the foregoing examples (e.g., a range defined by any of the endpoints listed above).

In various embodiments of isolation chambers 136, 138, 140, 336, or 436, the width Wcon of a connection region 142 at a proximal opening 152 (isolation chambers 136, 138, or 140, connection region 342 at a proximal opening 352 (isolation chambers 336), or a connection region 442 at a proximal opening 472 (isolation chambers 436) can be any of the following ranges: from about 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width Wcon of a connection region 142 at a proximal opening 152; connection region 342 at a proximal opening 352; or a connection region 442 at a proximal opening 472 can be different than the foregoing examples (e.g., a range defined by any of the endpoints listed above).

In various embodiments of isolation chambers 136, 138, 140, 336, or 436, the width Wcon of a connection region 142 at a proximal opening 152 (isolation chambers 136, 138, or 140), a connection region 342 at a proximal opening 352 (isolation chambers 336), or a connection region 442 at a proximal opening 472 (isolation chambers 436) can be any of the following ranges: from about 2-35 microns, 2-25 microns, 2-20 microns, 2-15 microns, 2-10 microns, 2-7 microns, 2-5 microns, 2-3 microns, 3-25 microns, 3-20 microns, 3-15 microns, 3-10 microns, 3-7 microns, 3-5 microns, 3-4 microns, 4-20 microns, 4-15 microns, 4-10 microns, 4-7 microns, 4-5 microns, 5-15 microns, 5-10 microns, 5-7 microns, 6-15 microns, 6-10 microns, 6-7 microns, 7-15 microns, 7-10 microns, 8-15 microns, and 8-10 microns. The foregoing are examples only, and the width Wcon of a connection region 142 at a proximal opening 152, a connection region 342 at a proximal opening 352, or a connection region 442 at a proximal opening 472 can be different than the foregoing examples (e.g., a range defined by any of the endpoints listed above).

In various embodiments of isolation chambers 136, 138, 140, 336, or 436, a ratio of the length Lcon of a connection region 142 to a width Wcon of the connection region 142 at the proximal opening 152 (isolation chambers 136, 138, or 140), a ratio of the length Lcon of a connection region 342 to a width Wcon of the connection region 342 at the proximal opening 352 (isolation chambers 336), or a ratio of the length Lcon of a connection region 442 to a width Wcon of the connection region a connection region 442 to a width Wcon of the connection region 442 at the proximal opening 472 (isolation chambers 436) can be greater than or equal to any of the following ratios: about 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length Lcon of a connection region 142 to a width Wcon of the connection region 142 at the proximal opening 152, the ratio of the length Lcon of a connection region 342 to a width Wcon of the connection region 342 at the proximal opening 372; or the ratio of the length Lcon of a connection region 442 to a width Wcon of the connection region 442 at the proximal opening 472 can be different than the foregoing examples.

In various embodiments of microfluidic devices having growth chambers 136, 138, 140, 336, or 436, Vmax can be set at about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 µL/sec.

In various embodiments of microfluidic devices having isolation chambers 136, 138, 140, 336, or 436, the volume of an isolation region 144 (isolation chambers 136, 138, or 140), 344 (isolation chambers 336) or 444 (isolation chambers 436) can be, for example, at least about $3\times10^3$, $6\times10^3$, $9\times10^3$, $1\times10^4$, $2\times10^4$, $4\times10^4$, $8\times10^4$, $1\times10^5$, $2\times10^5$, $4\times10^5$, $8\times10^5$, $1\times10^6$, $2\times10^6$, $4\times10^6$, $6\times10^6$ cubic microns, or more.

In some embodiments, the microfluidic device has isolation chambers 136, 138, 140, 336, or 436, wherein no more than about $1\times10^2$ biological cells may be maintained, and the volume of the isolation chambers may be no more than about $2\times10^6$ cubic microns.

In some embodiments, the microfluidic device has isolation chambers 136, 138, 140, 336, or 436, wherein no more than about $1\times10^2$ biological cells may be maintained, and the volume of the isolation chambers may be no more than about $4\times10^5$ cubic microns.

In yet other embodiments, the microfluidic device has isolation chambers 136, 138, 140, 336, or 436, wherein no more than about 50 biological cells may be maintained, and the volume of the isolation chambers may be no more than about $4\times10^5$ cubic microns.

In various embodiment, the microfluidic device has isolation chambers configured as in any of the embodiments discussed herein where the microfluidic device has about 100 to about 500 isolation chambers; about 200 to about 1000 isolation chambers, about 500 to about 1500 isolation chambers, about 1000 to about 2000 isolation chambers, or about 1000 to about 3500 isolation chambers.

In some other embodiments, the microfluidic device has isolation chambers configured as in any of the embodiments discussed herein where the microfluidic device has about 1500 to about 3000 isolation chambers, about 2000 to about 3500 isolation chambers, about 2000 to about 4000 isolation chambers, about 2500 to about 4000 isolation chambers, or about 3000 to about 4500 isolation chambers.

In some embodiments, the microfluidic device has isolation chambers configured as in any of the embodiments discussed herein where the microfluidic device has about 3000 to about 4500 isolation chambers, about 3500 to about 5000 isolation chambers, about 4000 to about 5500 isolation chambers, about 4500 to about 6000 isolation chambers or about 5000 to about 6500 isolation chambers.

In further embodiments, the microfluidic device has isolation chambers configured as in any of the embodiments discussed herein, where the microfluidic device has about 6000 to about 7500 isolation chambers, about 7000 to about 8500 isolation chambers, about 8000 to about 9500 isolation chambers, about 9000 to about 10,500 isolation chambers, about 10,000 to about 11,500 isolation chambers, about 11,000 to about 12,500 isolation chambers, about 12,000 to about 13,500 isolation chambers, about 13,000 to about 14,500 isolation chambers about 14,000 to about 15,500 isolation chambers, about 15,000 to about 16,500 isolation chambers, about 16,000 to about 17,500 isolation chambers, about 17,000 to about 18,500 isolation chambers.

In various embodiments, the microfluidic device has isolation chambers configured as in any of the embodiments discussed herein, where the microfluidic device has about 18,000 to about 19,500 isolation chambers, about 18,500 to about 20,000 isolation chambers, about 19,000 to about 20,500 isolation chambers, about 19,500 to about 21,000 isolation chambers, or about 20,000 to about 21,500 isolation chambers.

F. Other Properties of the Isolation Chambers

Although the barriers of microfluidic circuit material 116 (FIGS. 1A-1C) and 416 (FIGS. 4A-4C) that define the respective isolation chambers 136, 138, 140 of device 100 (FIGS. 1A-1C) and form the isolation structure 446 of isolation chambers 436 of device 400 (FIGS. 4A-4C) are illustrated and discussed above as physical barriers, it should be appreciated that the barriers can alternatively be created as "virtual" barriers comprising DEP forces activated by light in the light pattern 322.

In some other embodiments, respective isolation chambers 136, 138, 140, 336 and 436 can be shielded from illumination (e.g., by the detector and/or the selector control module directing the light source 320), or can be only selectively illuminated for brief periods of time. Cells and other biological micro-objects contained in the isolation chambers can thus be protected from further (i.e., possibly harmful) illumination after being moved into the isolation chambers 136, 138, 140, 336 and 436.

G. Coating Solutions and Coating Agents

Without intending to be limited by theory, maintenance of a biological micro-object (e.g., a biological cell) within a microfluidic device (e.g., a DEP-configured and/or EW-configured microfluidic device) may be facilitated (i.e., the biological micro-object exhibits increased viability, greater expansion and/or greater portability within the microfluidic device) when at least one or more inner surfaces of the microfluidic device have been conditioned or coated so as to present a layer of organic and/or hydrophilic molecules that provides the primary interface between the microfluidic device and biological micro-object(s) maintained therein. In some embodiments, one or more of the inner surfaces of the microfluidic device (e.g. the inner surface of the electrode activation substrate of a DEP-configured microfluidic device, the cover of the microfluidic device, and/or the surfaces of the circuit material) may be treated with or modified by a coating solution and/or coating agent to generate the desired layer of organic and/or hydrophilic molecules.

The coating may be applied before or after introduction of biological micro-object(s), or may be introduced concurrently with the biological micro-object(s). In some embodiments, the biological micro-object(s) may be imported into the microfluidic device in a fluidic medium that includes one or more coating agents. In other embodiments, the inner surface(s) of the microfluidic device (e.g., a DEP-configured microfluidic device) are treated or "primed" with a coating solution comprising a coating agent prior to introduction of the biological micro-object(s) into the microfluidic device.

In some embodiments, at least one surface of the microfluidic device includes a coating material that provides a layer of organic and/or hydrophilic molecules suitable for maintenance and/or expansion of biological micro-object(s) (e.g. provides a conditioned surface as described below). In some embodiments, substantially all the inner surfaces of the microfluidic device include the coating material. The coated inner surface(s) may include the surface of a flow region (e.g., channel), chamber, or isolation chamber/sequestration pen, or a combination thereof. In some embodiments, each of a plurality of isolation chambers has at least one inner surface coated with coating materials. In other embodiments, each of a plurality of flow regions or channels has at least one inner surface coated with coating materials. In some embodiments, at least one inner surface of each of a plurality of isolation chambers and each of a plurality of channels is coated with coating materials.

Coating agent/Solution. Any convenient coating agent/coating solution can be used, including but not limited to: serum or serum factors, bovine serum albumin (BSA), polymers, detergents, enzymes, and any combination thereof.

Polymer-based coating materials. The at least one inner surface may include a coating material that comprises a polymer. The polymer may be covalently or non-covalently bound (or may be non-specifically adhered) to the at least one surface. The polymer may have a variety of structural motifs, such as found in block polymers (and copolymers), star polymers (star copolymers), and graft or comb polymers (graft copolymers), all of which may be suitable for the methods disclosed herein.

The polymer may include a polymer including alkylene ether moieties. A wide variety of alkylene ether containing polymers may be suitable for use in the microfluidic devices described herein. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers may range in average molecular mass Mw from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a coated surface include Pluronic® L44, L64, P85, and F127 (including F127NF). Another class of alkylene ether containing polymers is polyethylene glycol (PEG Mw<100,000 Da) or alternatively polyethylene oxide (PEO, Mw>100,000). In some embodiments, a PEG may have an Mw of about 1000 Da, 5000 Da, 10,000 Da or 20,000 Da.

In other embodiments, the coating material may include a polymer containing carboxylic acid moieties. The carboxylic acid subunit may be an alkyl, alkenyl or aromatic moiety containing subunit. One non-limiting example is polylactic acid (PLA). In other embodiments, the coating material may include a polymer containing phosphate moieties, either at a terminus of the polymer backbone or pendant from the backbone of the polymer. In yet other embodiments, the coating material may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. In further embodiments, the coating material may include a polymer including amine moieties. The polyamino polymer may include a natural polyamine polymer or a synthetic polyamine polymer. Examples of natural polyamines include spermine, spermidine, and putrescine.

In other embodiments, the coating material may include a polymer containing saccharide moieties. In a non-limiting example, polysaccharides such as xanthan gum or dextran may be suitable to form a material which may reduce or prevent cell sticking in the microfluidic device. For example, a dextran polymer having a size about 3 kDa may be used to provide a coating material for a surface within a microfluidic device.

In other embodiments, the coating material may include a polymer containing nucleotide moieties, i.e. a nucleic acid, which may have ribonucleotide moieties or deoxyribonucleotide moieties, providing a polyelectrolyte surface. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation.

In yet other embodiments, the coating material may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA) and/or serum (or a combination of multiple different sera) comprising albumin and/or one or more other similar proteins as coating agents. The serum can be from any convenient source, including but not limited to fetal calf serum, sheep serum, goat serum, horse serum, and the like. In certain embodiments, BSA in a coating solution is present in a range of form about 1 mg/mL to about 100 mg/mL, including 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, or more or anywhere in between. In certain embodiments, serum in a coating solution may be present in a range of from about 20% (v/v) to about 50% v/v, including 25%, 30%, 35%, 40%, 45%, or more or anywhere in between. In some embodiments, BSA may be present as a coating agent in a coating solution at 5 mg/mL, whereas in other embodiments, BSA may be present as a coating agent in a coating solution at 70 mg/mL. In certain embodiments, serum is present as a coating agent in a coating solution at 30%. In some embodiments, an extracellular matrix (ECM) protein may be provided within the coating material for optimized cell adhesion to foster cell growth. A cell matrix protein, which may be included in a coating material, can include, but is not limited to, a collagen, an elastin, an RGD-containing peptide (e.g. a fibronectin), or a laminin. In yet other embodiments, growth factors, cytokines, hormones or other cell signaling species may be provided within the coating material of the microfluidic device.

In some embodiments, the coating material may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the coating material.

Covalently linked coating materials. In some embodiments, the at least one inner surface includes covalently linked molecules that provide a layer of organic and/or hydrophilic molecules suitable for maintenance/expansion of biological micro-object(s) within the microfluidic device, providing a conditioned surface for such cells.

The covalently linked molecules include a linking group, wherein the linking group is covalently linked to one or more surfaces of the microfluidic device, as described below. The linking group is also covalently linked to a moiety configured to provide a layer of organic and/or hydrophilic molecules suitable for maintenance/expansion of biological micro-object(s).

In some embodiments, the covalently linked moiety configured to provide a layer of organic and/or hydrophilic molecules suitable for maintenance/expansion of biological micro-object(s) may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

In various embodiments, the covalently linked moiety configured to provide a layer of organic and/or hydrophilic molecules suitable for maintenance/expansion of biological micro-object(s) in the microfluidic device may include non-polymeric moieties such as an alkyl moiety, a substituted alkyl moiety, such as a fluoroalkyl moiety (including but not limited to a perfluoroalkyl moiety), amino acid moiety, alcohol moiety, amino moiety, carboxylic acid moiety, phosphonic acid moiety, sulfonic acid moiety, sulfamic acid moiety, or saccharide moiety. Alternatively, the covalently linked moiety may include polymeric moieties, which may be any of the moieties described above.

In some embodiments, the covalently linked alkyl moiety may comprises carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the linking group.

In other embodiments, the covalently linked moiety may include at least one amino acid, which may include more than one type of amino acid. Thus, the covalently linked moiety may include a peptide or a protein. In some embodiments, the covalently linked moiety may include an amino acid which may provide a zwitterionic surface to support cell growth, viability, portability, or any combination thereof.

In other embodiments, the covalently linked moiety may include at least one alkylene oxide moiety, and may include any alkylene oxide polymer as described above. One useful class of alkylene ether containing polymers is polyethylene glycol (PEG Mw<100,000 Da) or alternatively polyethylene oxide (PEO, Mw>100,000). In some embodiments, a PEG may have an Mw of about 1000 Da, 5000 Da, 10,000 Da or 20,000 Da.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. Exemplary reactive pairing moieties may include aldehyde, alkyne or halo moieties. A polysaccharide may be modified in a random fashion, wherein each of the saccharide monomers may be modified or only a portion of the saccharide monomers within the polysaccharide are modified to provide a reactive pairing moiety that may be coupled directly or indirectly to a surface. One exemplar may include a dextran polysaccharide, which may be coupled indirectly to a surface via an unbranched linker.

The covalently linked moiety may include one or more amino groups. The amino group may be a substituted amine moiety, guanidine moiety, nitrogen-containing heterocyclic moiety or heteroaryl moiety. The amino containing moieties may have structures permitting pH modification of the environment within the microfluidic device, and optionally, within the isolation chambers and/or flow regions (e.g., channels).

The coating material providing a conditioned surface may comprise only one kind of covalently linked moiety or may include more than one different kind of covalently linked moiety. For example, the fluoroalkyl conditioned surfaces (including perfluoroalkyl) may have a plurality of covalently linked moieties which are all the same, e.g., having the same linking group and covalent attachment to the surface, the same overall length, and the same number of fluoromethylene units comprising the fluoroalkyl moiety. Alternatively, the coating material may have more than one kind of covalently linked moiety attached to the surface. For example, the coating material may include molecules having covalently linked alkyl or fluoroalkyl moieties having a specified number of methylene or fluoromethylene units and may further include a further set of molecules having charged moieties covalently attached to an alkyl or fluoroalkyl chain having a greater number of methylene or fluoromethylene units, which may provide capacity to present bulkier moieties at the coated surface. In this instance, the first set of molecules having different, less sterically demanding termini and fewer backbone atoms can help to functionalize the entire substrate surface and thereby prevent undesired adhesion or contact with the silicon/silicon oxide, hafnium oxide or alumina making up the substrate itself. In another example, the covalently linked moieties may provide a zwitterionic surface presenting alternating charges in a random fashion on the surface.

H. Fluidic Medium

With regard to the foregoing discussion about microfluidic devices having a flow channel and one or more isolation chambers, a fluidic medium (e.g., a first medium and/or a second medium) can be any fluid that is capable of maintaining a biological micro-object in a substantially viable and/or assayable state. The assayable state will depend on the biological micro-object and the assay being performed. For example, if the biological micro-object is a cell that is being assayed for the secretion of a protein of interest, the cell would be substantially assayable provided that the cell is viable and capable of expressing and secreting proteins. Methods of assaying cells within a microfluidic device having isolation chambers has been described, for example, in US Patent Application Publication No. 2015/0151298 and in U.S. application Ser. No. 15/372,094, filed Dec. 7, 2016, the contents of each of which is incorporated herein by reference in its entirety.

VI. Genetic Engineering

Tumor infiltrating cells can be engineered for expression of at least one pro-inflammatory polypeptide. The pro-inflammatory polypeptide can be, for example, a cytokine, a chemokine, a microbial antigen, an antibody, or fusion proteins thereof. Exemplary cytokines include IL-1, IL-2, IL-6, IL-7, IL-8, IL-15, TNF alpha, IFN (Type 1 or 2), CSF, GM-CSF, and IL-21. Exemplary chemokines include RANTES, IP-10, CXCL9, and CXCL10. Preferably, all such polypeptides are of human origin. Sequences of any of these polypeptides can be found in the Swiss-Prot database and/or the NCBI Protein database, among other sources.

The pro-inflammatory agent can also be a microbial antigen suitable for inducing an immune response. The microbial antigen can include at least one B-cell epitope or at least one T-cell epitope, or both. A preferred type of antigen is a superantigen, such SEA, SEA/E-120, or flagellar proteins. Superantigens are a recognized class of antigens, produced by some pathogenic bacteria or viruses as a defense mechanism, causing nonspecific activation of T cells and cytokine release. The antigens in conventional vaccines, such as flu, pneumococcal, tetanus, diphtheria, pertussis, hepatitis A or B, HPV, measles, mumps and rubella, varicella and meningococcal can also be expressed from TICs to stimulate an immune response proximate to a tumor.

The pro-inflammatory polypeptide can also be an antibody. As in other forms of therapy, the antibody is preferably chimeric, veneered, humanized, human or the like to reduce immunogenicity of the antibody itself. The heavy and light chain variable regions of chimeric, veneered, humanized, or human antibodies can be linked to at least a portion of a human constant region. The choice of constant region depends, in part, on whether antibody-dependent complement and/or cellular mediated cytotoxicity is desired. For example, human isotypes IgG1 and IgG3 have complement-mediated cytotoxicity and human isotypes IgG2 and IgG4 do not. Human IgG1 isotype is a preferred isotype.

Exemplary antibodies include inhibitory antibodies that specifically bind to and inhibit the function of CTLA-4, PD-1, PD-2, PD-L1, PD-L2, 4-1BB, or anti-CD40. Exemplary antibodies include ipilimumab (anti-CTLA-4) and pembrolizumab and nivolumab (anti-PD-1), and binding fragments of such antibodies, particularly scFv, as well as bispecific versions. An exemplary bispecific antibody combines a tumor-specific targeting domain (e.g., anti-HER2 antibody or the like) and a pro-inflammatory domain (e.g., IL-2 or an anti-CD3 antibody).

Antibodies or other naturally heterodimeric proteins can optionally be expressed as a single chain fusion protein in which the two components, heavy and light chain variable regions in the case of an antibody, are expressed fused together.

As well as being engineered to express at least one pro-inflammatory polypeptide, the tumor infiltrating cells can be genetically engineered to express an enzyme that facilitates matrix degradation. Exemplary enzymes include heparanase, collagenase, matrix metalloproteinase (e.g., MMP9), and plasminogen activator (e.g., urokinase). Such enzymes are preferably of human origin, exemplary sequences of which are provided in the Swiss-Prot database and/or the NCBI Protein database, among other sources. Such engineering can be performed by introducing a construct encoding the matrix degrading enzyme operably linked to a promoter expressible in the TICs, and optionally other regulatory sequences, or by activating expression of an endogenous matrix degrading enzyme.

Tumor infiltrating cells can also be engineered to express a receptor that targets the cells to a tumor. Such targeting can be performed, for example, by engineering T cells to express a CAR (Brocker et al., J. Ex. Med 181, 1653-1659 (1995; Ramos et al., Expert Opin Biol. Ther. 11, 855-873 (2011), Hombach et al., J. Immunol. 167, 6123-6131 92001), Maher et al., Nat. Biotech 20, 70-75 (2002), Finney et al., J. Immunol. 172, 104-113 (2004). CARs are engineered receptors including a binding domain (typically a scFv, transmembrane domain and signaling domain (typically CD30. Second generation CARs also include a costimulatory domain from CD38, 4-1BB or OX40 to optimize T cell activation. Third generation CARs also including the signaling domains of a third molecule, such as a TNF-receptor family member, including 4-1BB or OX40. All components are preferably of human origin. The binding domain specifically binds to an antigen expressed on the surface of tumor cells.

Genetic engineering of cells can be performed before or after separating cells on a microfluidic device; and the cells can be propagated before or after genetic engineering. Thus, genetic engineering can be performed on a clonal or mixed population of cells. For example, tumor infiltrating cells can be contacted with a transformation agent (e.g., any of the agents disclosed herein, such as CRISPR/Cas9, TALENs, zinc fingers, retroviruses and other viral vectors, transposons, etc.) prior to introducing the cells into a microfluidic (or nanofluidic) device, then propagated on the device, optionally after isolating individual tumor infiltrating cells into separate isolation chambers. In such embodiments, an assessment of the tumor cell-antigen specificity of the tumor infiltrating cells can be evaluated while propagating the cells on the device. Alternatively, tumor infiltrating cells can be contacted with a transformation agent while the cells are in the microfluidic (or nanofluidic) device, either before or after assessing the ability of the cells to specifically recognize and/or respond to tumor cell antigen(s). In such embodiments, the tumor infiltrating cells can be loaded into isolation chambers, either individually or in groups, and then the transformation agent can be flowed into the microfluidic device and incubated with the cells under conditions conducive to successful transformation. In still other alternatives, tumor infiltrating cells can be contacted with a transformation agent after selection within and export from the microfluidic device. In such embodiments, assessment of whether the cells have been successfully transformed can be performed using either conventional macrofluidic techniques or microfluidic techniques (e.g., by reintroducing the cells into a microfluidic device, isolating individual cells, and growing up single cell clones for nucleic acid analysis).

In certain embodiments, a clonal population of cells can be selected after genetic engineering. Moreover, a set of clonal populations of cells can be optionally pooled after genetic engineering and selection.

The tumor infiltrating cells can be genetically engineered to directly express the at least one pro-inflammatory polypeptide, for example, by introducing a construct encoding a pro-inflammatory polypeptide to be expressed, typically operably linked to one or more regulatory elements, such as a promoter. Optionally, the one or more regulator elements can include a promoter and one or more transcriptional enhancers. The promoter can be inducible, such as a tetracyclin-inducible, glucocorticoid-inducible, doxycycline-inducible, metal-inducible, or cumate-inducible promoter. Optionally, the pro-inflammatory polypeptide is linked to a masking moiety via a proteolytic cleavage site when initially expressed (see, e.g., WO 2009/025846). Cleavage at the proteloytic cleavage site by a protease expressed by a target tumor increases activity of the polypeptide at its intended site of action, thereby improving the activity-to-side effects profile.

The tumor infiltrating cells can also be genetically engineered to indirectly express the at least one pro-inflammatory polypeptide by introducing a construct encoding an agent, such as a transcription factor or a signaling protein involved in transcriptional regulation, that induces or represses the activity of an endogenous gene. For example, the tumor infiltrating cell could be genetically engineered to express a variant of NFkB that caused increased expression of pro-inflammatory polypeptides.

Regardless of whether the expression of the at least one pro-inflammatory polypeptide is direct or indirect, the genetic engineering can be accomplished using, for example, zinc finger proteins, siRNAs, TALENs, and/or Cas-CRISPR. These techniques facilitate site-specific DNA cleavage, to thereby induce targeted mutagenesis, induce targeted deletions of cellular DNA sequences, and facilitate targeted recombination and integration at a predetermined chromosomal locus. See, for example, Burgess (2013) Nature Reviews Genetics 14:80-81, Urnov et al. (2010) Nature 435(7042):646-51; US 20030232410; 20050208489; 20050026157; 20050064474; 20060188987; 20090263900; 20090117617; 20100047805; 20110207221; 20110301073 and WO 2007/014275, 20140170753, 20140170753.

Alternatively, the genetic engineering can be performed by transfection of a vector encoding a pro-inflammatory polypeptide and screening (optionally with drug selection). The construct can be viral in origin, such as a lentiviral vector or a retroviral vector. Such vectors can transduce cells without producing immunogenic viral proteins or having the transgene becoming a permanent part of the host cell genome.

Lentiviruses are a genus of retroviruses that are capable of infecting dividing and non-dividing cells. Several examples of lentiviruses include HIV (human immunodeficiency virus), including HIV type 1 and HIV type 2, visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. A lentiviral genome is generally organized into a 5' long terminal repeat (LTR), the gag gene, the pol gene, the env gene, the accessory genes (nef, vif, vpr, vpu) and a 3' LTR. The viral LTR is divided into three regions called U3, R and U5. The U3 region contains the enhancer and promoter elements. The U5 region contains the polyadenylation signals. The R (repeat) region separates the U3 and U5 regions and transcribed sequences of the R region appear at both the 5' and 3' ends of the viral RNA. See, for example, "RNA Viruses: A Practical Approach" (Cann, Ed., Oxford University Press, (2000)), Narayan and Clements J. Gen. Virology 70:1617-1639 (1989), Fields et al. Fundamental Virology Raven Press. (1990), Miyoshi et al., J Virol. 72(10):8150-7 (1998), and U.S. Pat. No. 6,013,516.

Gammaretrovirus are a genus of the retroviridae family. Exemplary gammaretroviruses include mouse stem cell virus, murine leukemia virus, feline leukemia virus, feline sarcoma virus, and avian reticuloendotheliosis viruses.

Viral vectors can be introduced into a cell packaged as virions. A packaging cell line provides the viral proteins that are required in trans for the packaging of the viral genomic RNA into viral particles. Examplary packaging cell lines include 293 (ATCC CCL X), HeLa (ATCC CCL 2), D17 (ATCC CCL 183), MDCK (ATCC CCL 34), BHK (ATCC CCL-10) and Cf2Th (ATCC CRL 1430), as described, for example, in U.S. Pat. No. 6,218,181.

The coding sequence for the pro-inflammatory polypeptide can be expressed from a retroviral promoter, such as the retroviral 5' long terminal repeat (LTR) promoter or promoters, typically used for expression in mammalian cells, such as a CMV, SV40, EF1A, PGK, CAGG, UBC promoter, or NFAT (nuclear factor of activated T cells, see Zhang et al., Mol. Thera 19, 751-759 (2011)).

Non-viral DNA transfection or transposons can also be used to genetically engineer tumor infiltrating cells. Non-viral delivery systems include, for example, electroporation, lipid-based delivery systems including liposomes, "naked" DNA, and delivery using polycyclodextrin compounds.

If more than one polypeptide is expressed in a tumor infiltrating cell, the polypeptide can be introduced on the same or different constructs.

After genetic engineering, cells are propagated. Conditions appropriate for cell culture include an appropriate media (e.g., Minimal Essential Media, RPMI Media 1640, or X-vivo 15 (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFp, and TNF-alpha or other additives for the growth of cells including surfactant, plasmanate, and reducing agents such as N-acetyl-cysteine and 2-mercaptoethanol. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of cells. Antibiotics, e.g., penicillin and streptomycin, are included only in experimental cultures, not in cultures of cells that are to be infused into a subject. Optionally TICs are stimulated with the antigen of the cancer in vitro. The target cells are maintained under conditions necessary to support growth, for example, an appropriate temperature (e.g., 37° C.) and atmosphere (e.g., air plus 5% CO2. Preferably, the yield of cells is at least $10^4$, $10^5$, $10^6$ or $10^7$ cells. Adequate yields for treatment can sometimes be obtained after 1-3 days. Sometimes cells are cultured in rapamycin (to limit differentiation and/or exhaustion of T cells during culture, and/or maintain a subset of cells at the memory T cell stage of differentiation). If the cells have been separated into clonal isolates, individual clonal isolates can optionally be pooled before administration to a patient.

Following or during culturing of engineered TICs, a sample of TICs can be tested for proper integration and expression of the transgene transformed into the TICs. Such testing can be by standard techniques, such as sequencing and/or blotting.

Figure 5:
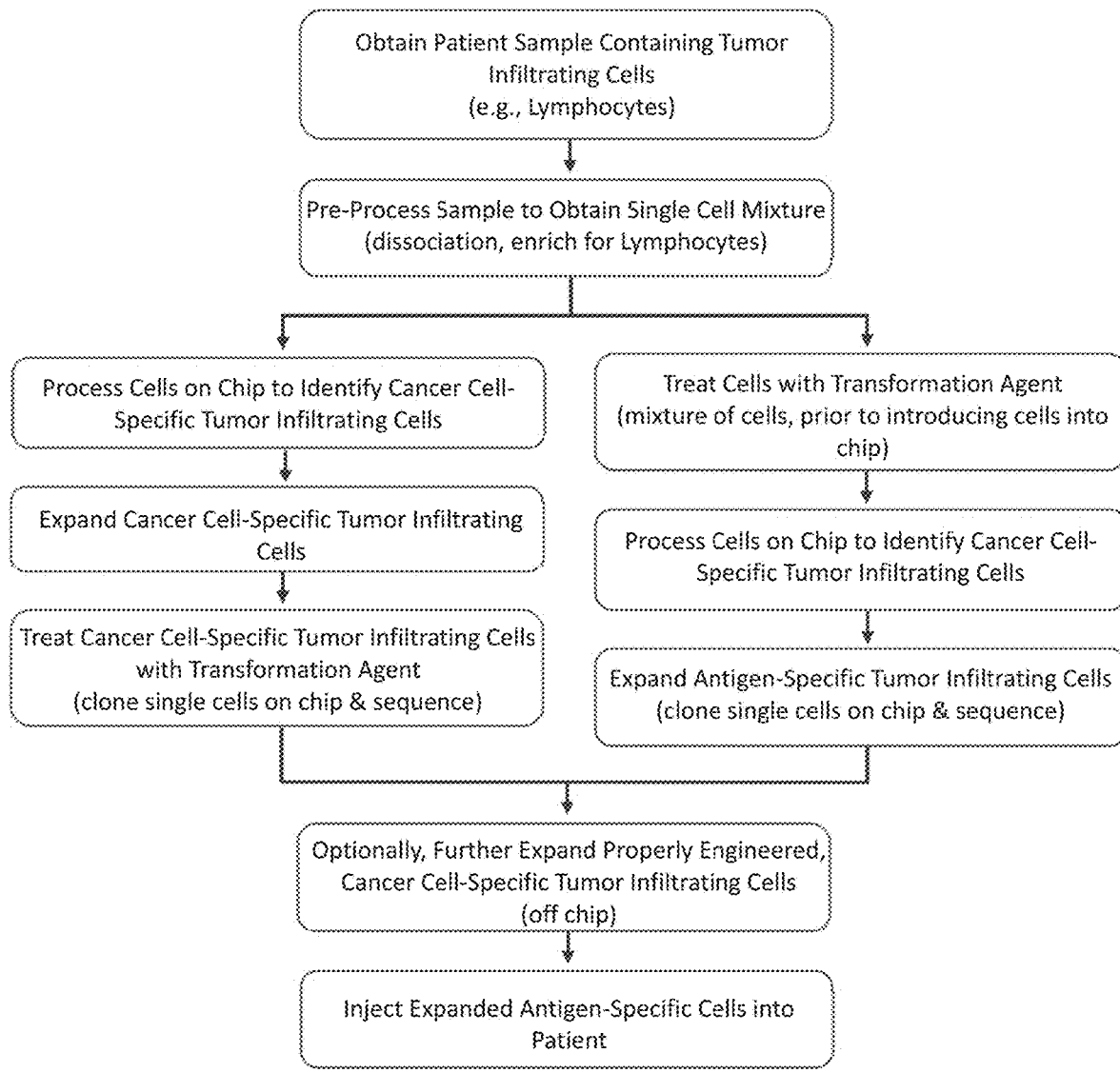
FIG. 5 shows exemplary workflows that can be practiced as embodiments of the invention.

FIG. 5 illustrates alternative work flows for genetic engineering of TICs. In the work flow on the left TICs are separated and expanded before genetic transformation. In the work flow on the right, tumor cells are genetically engineered before isolation of TICs.

VII. Methods of Treatment

After propagation, genetically engineered tumor infiltrating cells are administered to a patient in an effective regime to treat a cancer. Any of the cancer types mentioned above are treatable, among others. The cancer can be a primary or secondary cancer and can be localized or metastatic. Preferably, the genetically engineered tumor infiltrating cells are administered to the same patient as that from who the cells were originally obtained (autologous treatment). If the cells are administered to a different patient (allogenic treatment), the patient typically has a cancer of the same type as that from which the tumor infiltrating cells were obtained. Also, for a patient who is not the source of the tumor infiltrating cells, the patient and cells are preferably checked for HLA compatibility to avoid rejection. Preferably at least five, and more preferably all 6, major HLA antigen are matched.

Genetically engineered tumor infiltrating cells are administered in an effective regime, meaning a dosage, route of administration, and frequency of administration that delays the onset, reduces the severity, inhibits further deterioration, and/or ameliorates at least one sign or symptom of a disorder. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Genetically engineered tumor infiltrating cells can be administered systemically or can be injected directly into a tumor. Intravenous, intra-arterial, or subcutaneous delivery is preferred for systemic administration.

Before administering the genetically engineered tumor infiltrating cells to a patient, the patient can undergo treatment to deplete endogenous immune cells, particularly immune-suppressive cells (see, e.g., Dudley et al., J. Clin. Oncol. 23, 2346-2357 (2005); J. Clin. Oncol. 26, 5233-5239 (2008)). Lympho-depletion enhances engraftment of transferred cells. Host conditioning may reduce tumor burden, improving the ratio of cells administered to target cells, reduce the population of inhibiting regulatory T cells, and induce production of metastatic cytokines to facilitate proliferation of transferred cells. Typical regimes for host conditioning include cyclophosphamide with or without fludarabine or irradiation.

If the genetically engineered tumor infiltrating cells to be administered express a polypeptide from an inducible promoter, an inducer (e.g., tetracyclin for a tetracyclin-inducible promoter) is co-administered with the cells to induce expression from the promoter in situ. Co-administration means the cells and inducer are administered sufficiently proximal in time that the inducer induces expression of the pro-inflammatory polypeptide encoded by the cells at such time as augments the action of the cells on the cancer they are targeted against. For example, the inducer can be administered shortly after the cells, which could be the same day, e.g., 1, 2, 3, 4, 5, 6 hours or more after the cells. The inducer can also be administered at a time when some or most (e.g., at least 50%, 60%, 70%, 80%, 85%, 90%, 95%, or more) of the cells administered to the patient have successfully infiltrated tumors. In addition, the inducer can be administered periodically, such as daily, every 2, 3, 4, 5, 6, or 7 days, weekly, etc.

Treatment with genetically engineered tumor infiltrating cells can be combined with one or more other treatments to make the environment of the tumors being treated more pro-inflammatory. The second treatment may be, for example, an adjuvant promoting an immune response, such as QS-21 or Ribi, and/or a pro-inflammatory cytokine. Examples of such cytokines are lymphokines, monokines, and traditional polypeptide hormones. Included among cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor; hepatic growth factor; fibroblast growth factor; prolactin; placental lactogen; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-$\alpha$; platelet-growth factor; transforming growth factors (TGFs) such as TGF-$\alpha$ and TGF-$\beta$; insulinlike growth factor-I and -II; erythropoietin (EPO); osteoinductive factors; interferons such as interferon-$\alpha$, -$\beta$ and -$\gamma$ colony stimulating factors (CSFs) such as macrophage-CSF (M-CSF); granulocyte-macrophage-CSF (GM-CSF); and granulocyte-CSF (G-CSF); interleukins (ILs) such as IL-1, IL-la, IL-2, IL-3, IL-4, IL-5, IL-6, IL-7, IL-8, IL-9, IL-10, IL-11, IL-12; a tumor necrosis factor such as TNF-$\alpha$ or TNF-$\beta$; and other polypeptide factors including LIF and kit ligand (KL).

Some of the same types of pro-inflammatory polypeptide that can be expressed from the cell can also be administered systemically. Some cytokines, such as IL-7 and IL-15, can promote proliferation of administered cells and inhibit proliferation of endogenous suppressive T cells.

The cells can be administered as a one-time dose or repeatedly at a frequency that can be daily, weekly, monthly, quarterly, or at irregular intervals in response to changes in the patient's condition or progression of the disorder being treated. The number of dosages administered depends on whether the cancer can be put in permanent remission or merely reduced in severity or put in temporary remission. For some cancers between 1 and 10 doses are often sufficient. Sometimes a single bolus dose, optionally in divided form, is sufficient. Treatment can be repeated for recurrence of cancer. For persistently recurring cancer, TICs can be administered at regular intervals, e.g., weekly, fortnightly, monthly, quarterly, every six months, for at least 1, 5 or 10 years, or the life of the patient.

Pharmaceutical compositions for parenteral administration can be manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, cells can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively, cells can be stored frozen or in the cold before use.

Treatment with TICs can be combined with other treatments effective against the cancer being treated, such as chemotherapy, radiation, stem cell treatment, surgery, or treatment with other biologics such as Herceptin™ (trastuzumab) against the HER2 antigen, Avastin™ (bevacizumab) against VEGF, or antibodies to the EGF receptor, such as (Erbitux™, cetuximab) and Vectibix™ (panitumumab), anti-CTLA, anti-PD-1, anti-PD2 anti-PD-L1, or anti-PD-L2. Chemotherapy agents include BRAF inhibitors, chlorambucil, cyclophosphamide or melphalan, carboplatinum, daunorubicin, doxorubicin, idarubicin, mitoxantrone, methotrexate, fludarabine, cytarabine, etoposide, topotecan, vincristine, and vinblastine.

All patent filings, websites, other publications, accession numbers and the like cited above or below are incorporated by reference in their entirety, for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1. Membrane Preparation and Bead Conjugation Protocol

The following protocol demonstrates the feasibility of obtaining samples containing proteins (and other biomolecules), and particularly membrane bound or membrane associated proteins, from samples cells of interest. The protocol is performed on Jurkat cells to enable testing of the resulting samples for proteins known to be present in such cells. The protocol could be readily extended to other cell types, including cancer cells isolated from a tumor biopsy, thereby yielding samples containing tumor cell-specific (or other cell type-specific) antigens useful for screening immunological cells (such as T cells, NK cells, etc.) for their reactivity to the antigens.

Materials:
Jurkat cells (ATCC TIB-152)
LiDS-Sample Buffer: 0.02 g/mL LiDS, 10% glycerol, 0.51 mM EDTA, 247 mM Tris, pH8.5 (ThermoFisher B0008)
Qiashredder (Qiagen 79654)
DPBS (containing calcium and magnesium, ThermoFisher 14040-182)
UltraPure Water (ThermoFisher 10977-015)
EZ-Link Sulfo-NHS-SS-Biotin (ThermoFisher 21328): store at −20° C., take out and warm at RT ~30 min before use; spin down briefly to collect everything at the bottom of the tube; immediately before use, add 164 µL ultrapure water to 1 tube containing 1 mg Sulfo-NHS-SS-Biotin and pipette up and down several times to dissolve (results in a 10 mM solution)
Complete Ultra mini (Sigma 5892791001): Prepare 20× solution: dissolve 1 tablet in 500 µL water by vortexing (stable for 4 weeks at 4° C. or −20° C.)
Minute Plasma Membrane Protein Isolation Kit (Invent Biotechnologies SM-005): Before use, thaw Solutions A and B, and add protease inhibitors:
for each sample 500 µL Buffer A+25 µL 20× protease inhibitors (store on ice)
for each sample 200 µL Buffer B+10 µL 20× protease inhibitor (store on ice)
prepare 1 filter cartridge for each sample on ice
BSA: Chromatopur Bovine Albumin (MP Biomedicals 02180561)
Streptavidin coated magnetic microspheres (Bangs Laboratories CM01N Lot #11806), wash and block before use:
Vortex beads, take out 300 µL/sample and transfer into 1.5 mL tube
Wash with PBS
Resuspend in 0.5% BSA and incubate at 4° C. (rotating) for at least 1 h
Wash with PBS, resuspend in 500 µL DPBS (+protease inhibitors)/sample
Anti-alpha 1 Sodium Potassium ATPase (Na/K-ATPase) antibody (Abcam ab7671)
Anti-human CD3 antibody, clone SK7 (BioLegend 344802)
Anti-human CD45 antibody, clone H130 (BioLegend 304002)
F(ab')2-Goat anti-Mouse IgG (H+L), Alexa Fluor 488 (ThermoFisher A-11017)

Figure 6:
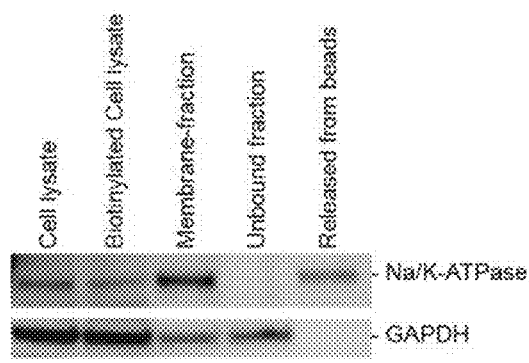
FIG. 6 shows a Western blot of various fractions from Jurkat cells.

A. Biotinylation of Membrane Proteins:
Count Jurkat cells
Prepare an aliquot for Western Blot analysis:
centrifuge 2×10$^6$ cells
wash with PBS
lyse in LiDS-Sample Buffer and centrifuge through a Qiashredder column to shear DNA
store at 4° C. for a few days, longer at −80° C.
Wash multiples of 15×10$^6$ cells three times with DPBS by centrifugation
Resuspend each pellet in 500 µL DPBS, transfer into a 1.5 mL tube and add 10 µL of freshly prepared 10 mM Sulfo-NHS-SS-Biotin
Rotate 30 min at RT
Wash three times with cold DPBS and proceed with cell pellets to enrich the membrane fractions
Process 1 sample for Western Blot analysis (see above).
FIG. 6 shows an exemplary Western blot stained for Na/K-ATPase, a protein present in the plasma membrane, and GAPDH, a cytosolic protein.

Enrichment of the Membrane Fraction Using Minute Plasma Membrane Isolation Kit:
Perform all steps on ice, centrifuge at 4° C.
1. Resuspend pellets in Buffer A: 200 µl for <5×10$^6$ cells, 500 µl for >5×10$^6$ cells
2. Incubate on ice for 10 min
3. Vortex vigorously for 10-30 sec, immediately transfer to the filter cartridge on ice 4. Cap the filter cartridge, centrifuge 30 sec at 16,000 g (increase to 2 min if cell lysate does not go through)
5. Resuspend the pellet in collection tube, transfer to the same filter and centrifuge again
6. Discard filter, resuspend pellet by vigorously vortexing for 10 sec
7. Centrifuge 1 min at 700 g (to pellet intact nuclei)
8. Centrifuge supernatant in a fresh 1.5 ml tube 30 min at 16,000 g/4° C. (4 supernatant contains cytosol, pellet=total membrane protein fraction)
9. Resuspend pellet in 200 µl buffer B by vortexing, or pipetting up and down
10. Centrifuge 20 min at 7,800 g/4° C.→pellet contains organelle membrane proteins
11. Carefully transfer supernatant (membrane fraction) into a fresh 2.0 ml tube Bind Membrane Fractions to Streptavidin-Coated Magnetic Microspheres:
1. Add 80 µL of each membrane fraction to 500 µL beads
2. Rotate o/n at 4° C.
3. Save unbound fraction for analysis by Western Blot
4. Rotate 30 min in 0.5% BSA/PBS+protease inhibitors
5. Wash with PBS
6. Resuspend in 250 µL 0.1% BSA/PBS+protease inhibitors Release Membrane Fractions from Beads (Cleave S—S Bond Using DTT):
1. Take out an aliquot of 50 µL beads
2. put on magnet and remove solution
3. Resuspend beads in 50 µL LiDS-Sample Buffer containing 50 mM DTT (1× Reducing Agent, ThermoFisher B0009)
4. Incubate 2 hr at RT (mix every ~30 min)

Figure 7:
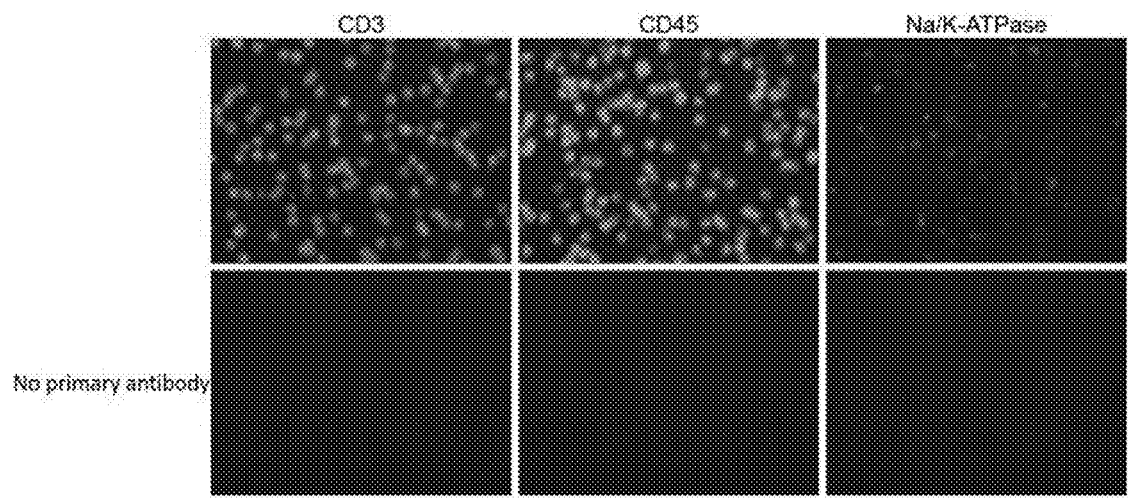
FIG. 7 shows beads coated with Jurkat cell membrane fractions stained with anti-CD3, anti-CD45 or anti-Na/K-ATPase antibodies.
Figure 8:
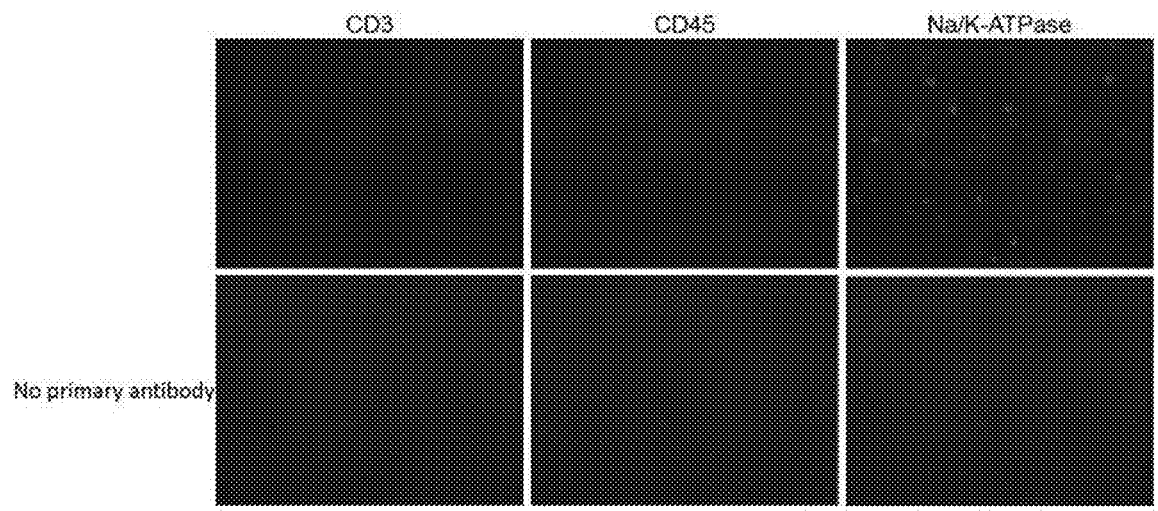
FIG. 8 shows beads coated with HEK293 cells stained with the same antibodies as in FIG. 7.

Antibody Staining:
1. Take 50 µL aliquots of beads (from step 24) for each antibody in following dilutions
CD3 (1:200)
CD45 (1:100)
Na/K-ATPase (1:100)
No primary antibody
2. Rotate 30 min at 4° C.
3. Add 800 µL PBS to wash, wash 1× additionally with PBS
4. Incubate in secondary antibody (Alexa488-conjugated goat anti-mouse) for 30 min at 4° C. (rotating, volume: 200 µL in 0.5% BSA/PBS+protease inhibitors) 1:300
5. Add 800 µL PBS to wash, wash 1× additionally with PBS
6. Resuspend in 20 µL 0.5% BSA/PBS+protease inhibitors
7. Image on fluorescence microscope FIG. 7 shows beads coated with a Jurkat cell membrane fraction stained for CD3, CD45 or Na/K-ATPase. CD3 and CD45 are both strongly represented compared with NA/K-ATPase, which appears as fainter spots. FIG. 8 shows a comparison with HEK293 cells. Here Na/K-ATPase stains the same, but CD3 and CD45 are absent.

The results demonstrate that proteins isolated from cell membrane preparations can be successfully coupled to beads. Such beads could be mixed with immunological cells to determine which cells are reactive to antigens (whether protein or otherwise) present in the cell membrane preparations.

Example 2. Isolation of Tumor Infiltrating Cells from a Total Tumor Biopsy

A tumor biopsy was obtained from a patient suffering from cancer. The tumor biopsy was mechanically dissociated, resulting in the recovery of $7 \times 10^5$ cells having 15% viability. The cells were incubated overnight with anti-CD3/anti-CD28 magnetic beads (DYNABEADS™, Thermofisher Scientific, Cat. No. 11453D). The next day, non-adherent cells were collected and flowed into an OptoFluidic™ microfluidic device configured with Opto-Select™ technology (Berkeley Lights, Inc.). The microfluidic device included a microfluidic channel and a plurality of NanoPen™ chambers fluidically connected thereto. The T cell/bead resuspension was introduced into the microfluidic device by flowing the resuspension through a fluidic inlet and into the microfluidic channel. The flow was stopped and cells/beads were randomly loaded into the NanoPen™ chambers (a type of isolation chamber/sequestration pen, as described herein) by tilting the chip and allowing gravity to pull the T cells/beads into the chambers. T cell culture medium containing RPMI+10% FBS, 2% human serum, and 6000 U IL2 was perfused through the microfluidic channel of the microfluidic device for a period of three (3) days.

Following the three-day culture period, the cells loaded into the NanoPen™ chambers were analyzed for growth. Out of a total of 3087 NanoPen™ chambers that were loaded on day 0, cell growth was observed in 439 (or 14.2%) of the chambers.

The results of this experiment demonstrate that tumor infiltrating cells (TICS) responsive to T cell culture medium can be successfully isolated from total tumor biopsies and expanded in an OptoFluidic™ microfluidic device.

Example 3. Isolation of T Cells from a Tumor Draining Lymph Node

A fine needle aspirate (FNA) from a tumor-draining lymph node was obtained from the same patient as in Example 2. The FNA was mechanically dissociated, and the resulting material was filtered and spun down. $2.3 \times 10^6$ cells having a 91% viability were recovered. The cells were incubated overnight with anti-CD3/anti-CD28 magnetic beads (DYNABEADS™, Thermofisher Scientific, Cat. No. 11453D). The next day, non-adherent cells were collected and stained with anti-CD4 and anti-CD8 antibodies labeled with a PE-CF594 fluorescent dye. Cells that were CD4+ or CD8+ were isolated by FACS and flowed into an OptoFluidic™ microfluidic device configured with Opto-Select™ technology (Berkeley Lights, Inc.). The microfluidic device included a microfluidic channel and a plurality of NanoPen™ chambers fluidically connected thereto. Single cells were subsequently loaded into individual NanoPen™ chambers using the Opto-Select™ technology (which uses DEP force, as described herein). A total of 466 NanoPen™ chambers were loaded with single cells. T cell culture medium containing RPMI+10% FBS, 2% human serum, and 6000 U IL2 was perfused through the microfluidic channel of the microfluidic device for a period of three (3) days.

Following the three-day culture period, the cells were analyzed for growth. A total of 80 T cells loaded into NanoPen™ chambers on day 0 (about 17%) were observed to form clonal colonies by day 3.

The results of this experiment demonstrate that T cells located within a tumor-proximal lymph node can be isolated and successfully expanded into clonal populations in an OptoFluidic™ microfluidic device. T cells located in a tumor draining lymph node are considered likely tumor infiltrating lymphocytes (TILs).

Example 4. Isolation of Tumor Infiltrating T Cells from a Renal Cell Carcinoma Biopsy A renal cell carcinoma (RCC) biopsy was obtained from a patient. The RCC biopsy was mechanically dissociated, resulting in the recovery of 6.6×10⁶ cells having 70% viability. The resulting cells were FACS sorting for CD45+ cells, resulting in the isolation of 1.7×10⁶ cells having 74% viability. The CD45+ cells were incubated overnight with anti-CD3/anti-CD28 magnetic beads (DYNABEADS™, Thermofisher Scientific, Cat. No. 11453D). The next day, non-adherent cells were collected and flowed into an Opto-Fluidic™ microfluidic device configured with Opto-Select™ technology (Berkeley Lights, Inc.). The microfluidic device included a microfluidic channel and a plurality of NanoPen™ chambers fluidically connected thereto, and further included internal surfaces conditioned with covalently-linked polyethylene glycol (PEG). T cells/beads were randomly loaded into the NanoPen™ chambers by tilting the microfluidic device and allowing gravity to pull the T cells/beads into the chambers. After loading the T cells/beads into the NanoPen™ chambers, T cell culture medium containing RPMI+10% FBS, 2% human serum, and 6000 U IL2 for a period of four (4) days, after which the cells were analyzed for CD4/CD8 expression and growth.

Various NanoPen™ chambers that were loaded on day 0 exhibit growth of CD4+/CD8+ cells in the NanoPen™ chambers. The results of this experiment demonstrate that tumor infiltrating lymphocytes (TILs) can be successfully isolated from RCC biopsies and expanded in an OptoFluidic™ microfluidic device.

Example 5. Human T Cell Expansion in a Nanofluidic Device

CD3+ human T lymphocytes isolated from peripheral blood were mixed with anti-CD3/anti-CD28 magnetic beads (DYNABEADS™, Thermo Fisher Scientific, Inc.) at a ratio of 1 bead/1 cell. The mixture was incubated for 5 hours in a 5% CO2 incubator at 37° C. Following the incubation, the T cell/bead mixture was resuspended and introduced into an OptoFluidic™ microfluidic device configured with Opto-Select™ technology (Berkeley Lights, Inc.). The microfluidic device included a microfluidic channel and a plurality of NanoPen™ chambers fluidically connected thereto. The T cell/bead resuspension was introduced into the microfluidic device by flowing the resuspension through a fluidic inlet and into the microfluidic channel. The flow was stopped and T cells/beads were randomly loaded into NanoPen™ chambers by tilting the microfluidic device and allowing gravity to pull the T cells/beads into the chambers. After loading the T cells/beads into the NanoPen™ chambers, T cell culture medium containing RPMI, 10% FBS, 2% Human AB serum, and 50 U/ml IL2 (R&D Systems) was perfused through the microfluidic channel of the microfluidic device for a period of 4 days. The NanoPen™ chambers, and any T cells and beads contained therein, were imaged every 30 minutes for the entire 4-day culture.

Figure 9:
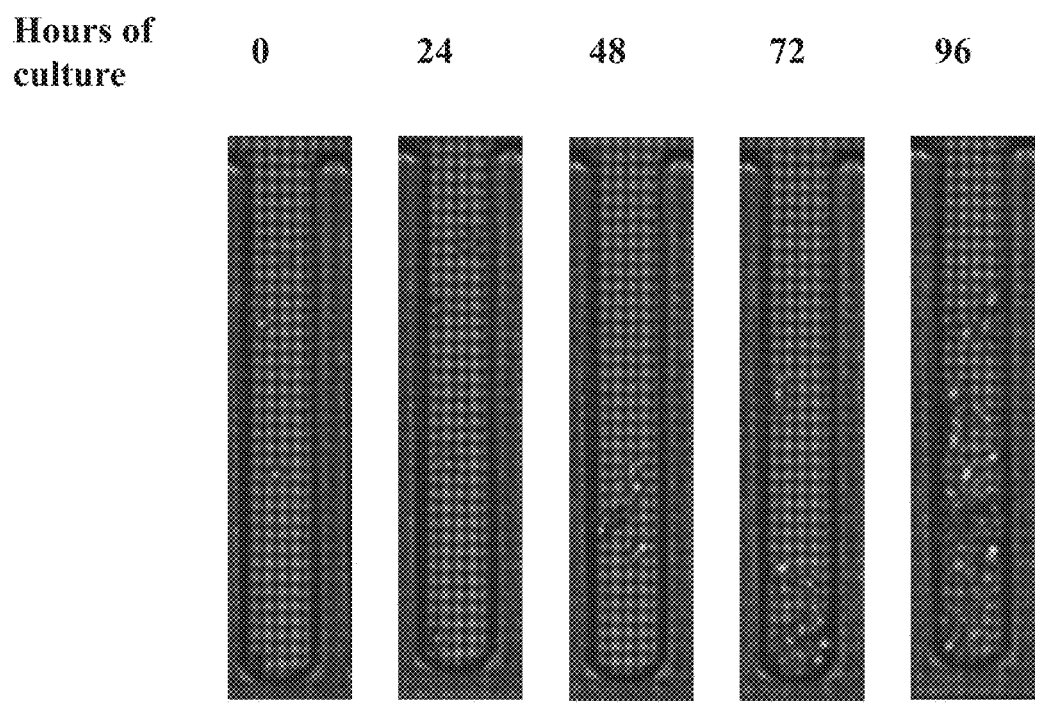
FIG. 9 provides a series of time-lapse images of a single isolation chamber in a microfluidic chip containing human T lymphocytes cultured with anti-CD3/anti-CD28 T cell-activating beads. The images show the isolation chamber at 0, 24, 48, 72, and 96 hours of culture.

FIG. 9 is a series of time-lapse images of a single NanoPen™ chambers at 0, 24, 48, 72, and 96 hours of culture, in which CD3+ human T lymphocytes were successfully expanded within the microfluidic device in accordance with the foregoing method. As can be seen, a small number of T cells at time t=0 resulted in an oligo-clonal population of T cells after 96 hours of on-chip culture.

Example 6. Selective Expansion of Human T Cells in a Nanofluidic Device

Human CD14+ monocytes isolated from peripheral blood were cultured for 7 days in DC culture medium containing RPMI, 10% FBS, 2% Human AB serum, 100 ng/ml GM-CSF, and 50 ng/ml IL-4 (R&D Systems) to promote differentiation of dendritic cells (DCs). 250 ug/ml LPS (R&D Systems) was added to the culture medium during the last 2 days of culture to promote DC activation.

Allogeneic donor T lymphocytes were mixed with DCs from the foregoing culture at a ratio of ~10 T cells/1 DC and incubated for 5 hours in a 5% CO2 incubator at 37° C. Following the incubation, the T cells/DCs mixture was resuspended and introduced into an OptoFluidic™ microfluidic device configured with Opto-Select™ technology (Berkeley Lights, Inc.). The microfluidic device included a microfluidic channel and a plurality of NanoPen™ chambers fluidically connected thereto. The T cells/DCs resuspension was introduced into the microfluidic device by flowing the resuspension through a fluidic inlet and into the microfluidic channel. The flow was stopped and T cells/DCs were randomly loaded into NanoPen™ chambers by tilting the device and allowing gravity to pull the T cells/DCs into the chambers.

After loading the T cells/DCs into the NanoPen™ chambers, T cell culture medium containing RPMI, 10% FBS, 2% Human AB serum, and 50 U/ml IL2 (R&D Systems) was perfused through the microfluidic channel(s) of the chip for a period of 4 days. The NanoPen™ chambers, and any T cells and DCs contained therein, were imaged every 30 minutes for the entire 4-day culture period.

Figure 10A:
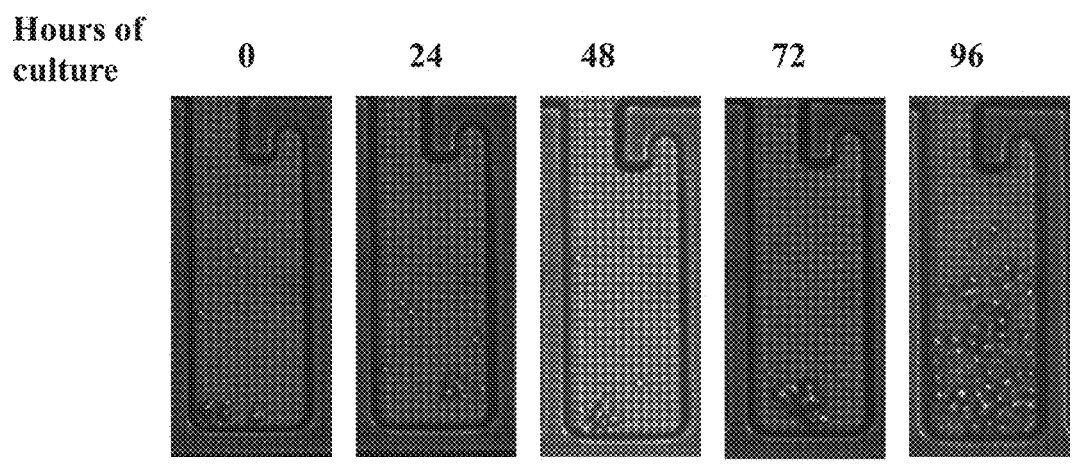
FIG. 10A provides a series of time-lapse images of a single isolation chamber in a microfluidic chip containing human T lymphocytes cultured with allogeneic dendritic cells (DCs). The images show the isolation chamber at 0, 24, 48, 72, and 96 hours of culture.

FIG. 10A is a series of time-lapse images of a single NanoPen™ chamber at 0, 24, 48, 72, and 96 hours of culture, in which CD3+ human T lymphocytes were selectively expanded on chip in accordance with the foregoing method. As can be seen, the DCs stimulated significant expansion of the T cells after 96 hours of on-chip culture. However, only 1%-2% of nanowells initially seeded with at least one T cell and at least one DC exhibited T cell expansion, demonstrating that the expansion observed in FIG. 10A was selective.

Figure 11A:
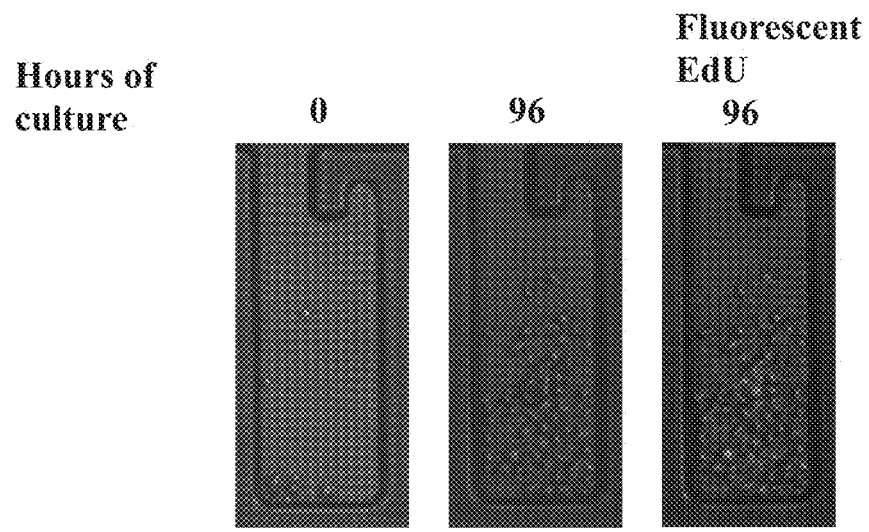
FIG. 11A provides an image showing the incorporation of EdU (fluorescence signal) in the T cells in the isolation chamber of FIG. 10A. EdU incorporation is shown (red) for the 96-hour culture time point and is overlaid on a brightfield image of the selectively expanded T cells.

During the last 16 hours of the 4-day culture period, the culture medium used to perfuse the chip was supplemented with Click-It EdU reagent (Thermo Fisher Scientific, Inc.), allowing the T cells to take up the reagent and incorporate it into their DNA. Following the culture period, the cells were washed, fixed with 3.7% formaldehyde, and permeabilized with 0.1% Triton-X. EdU incorporation was detected by monitoring fluorescence in the Texas Red channel. FIG. 11A provides an image showing the EdU fluorescence signal overlaid on a bright-field image of the selectively expanded T cells.

Example 7. Antigen-Specific Expansion of Human T Cells in a Nanofluidic Device Human CD14+ monocytes isolated from peripheral blood were cultured for 7 days in DC culture medium containing RPMI, 10% FBS, 2% Human AB serum, 100 ng/ml GM-CSF, and 50 ng/ml IL-4 (R&D Systems) to promote differentiation of dendritic cells (DCs). 250 ug/ml LPS (R&D Systems) was added to the culture medium during the last 2 days of culture to promote DC activation. At the same time as the addition of the LPS, the DCs were also pulsed with 10 uM Tetanus toxin (TT) antigen (Sigma-Aldrich Co.) and 10 uM Epstein Barr Virus (EBV) antigen (EastCoast Bio, Inc.).

Autologous donor T lymphocytes were mixed with TT- and EBV-pulsed DCs from the foregoing culture at a ratio of ~10 T cells/1 DC and incubated for 5 hours in a 5% CO2 incubator at 37° C. Following the incubation, the T cells/DCs mixture was resuspended and introduced into a Opto-Fluidic™ microfluidic device configured with Opto-Select™ technology (Berkeley Lights, Inc.). The microfluidic device included a microfluidic channel and a plurality of NanoPen™ chambers fluidically connected thereto. The T cells/DCs resuspension was introduced into the microfluidic device by flowing the resuspension through a fluidic inlet and into the microfluidic channel. The flow was stopped and T cells/DCs were randomly loaded into NanoPen™ chambers by tilting the device and allowing gravity to pull the T cells/DCs into the chambers.

After loading the T cells/DCs into the NanoPen™ chambers, T cell culture medium containing RPMI, 10% FBS, 2% Human AB serum, and 50 U/ml IL2 (R&D Systems) was perfused through the microfluidic channel(s) of the chip for a period of 5 days. The NanoPen™ chambers and any T cells and beads contained therein were imaged every 30 minutes for the entire 5-day culture period.

Figure 10B:
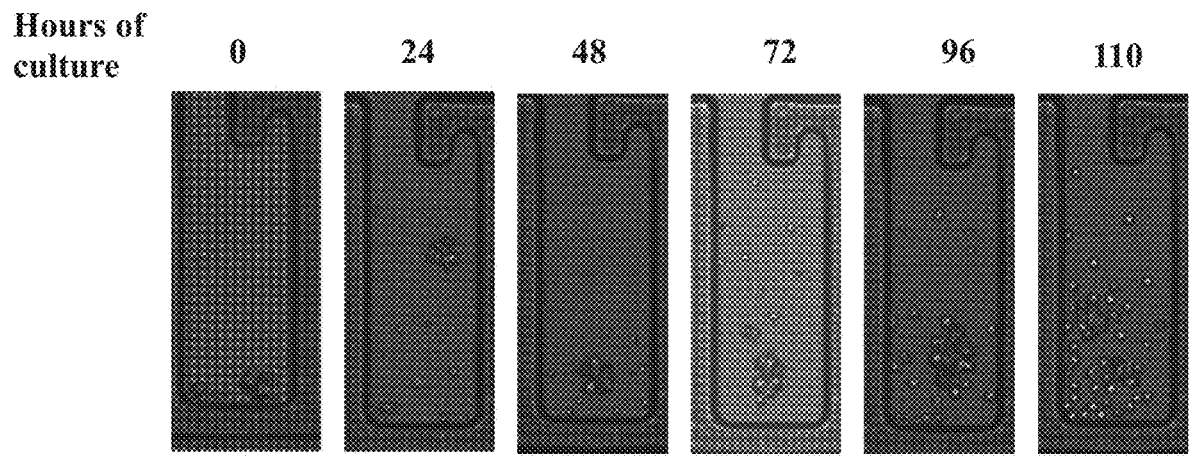
FIG. 10B provides a series of time-lapse images of a single isolation chamber in a microfluidic chip containing human T lymphocytes cultured with dendritic cells (DCs) that have been pulsed with tetanus toxin and Epstein bar virus antigens. The images show the isolation chamber at 0, 24, 48, 72, 96, and 110 hours of culture.

FIG. 10B is a time-lapse series of images of a single NanoPen™ chamber at 0, 24, 48, 72, 96, and 110 hours of culture, in which CD3+ human T lymphocytes were selectively expanded on chip in accordance with the foregoing method. As seen, the DCs stimulated significant expansion of the T cells after 110 hours of on-chip culture. However, only 1%-2% of chambers initially seeded with at least one T cell and at least one DC exhibited T cell expansion, demonstrating that the expansion observed in FIG. 10B was antigen specific.

Figure 11B:
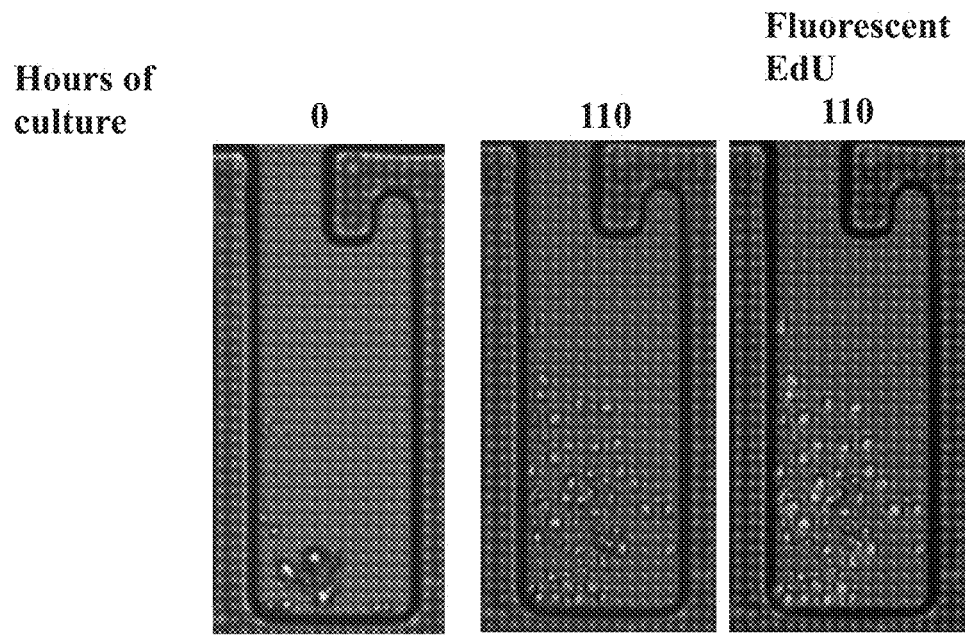
FIG. 11B provides an image showing the incorporation of EdU (fluorescence signal) in the T cells in the isolation chamber of FIG. 10B. EdU incorporation is shown (red) for the 110-hour culture time point and is overlaid on a brightfield image of the selectively expanded T cells.

During the last 16 hours of the 5-day culture period, the culture medium used to perfuse the chip was supplemented with Click-It EdU reagent (Thermo Fisher Scientific, Inc.), allowing the T cells to take up the reagent and incorporate it into their DNA. Following the culture period, the cells were washed, fixed with 3.7% formaldehyde, and permeabilized with 0.1% Triton-X. EdU incorporation was detected by monitoring fluorescence in the Texas Red channel. FIG. 11B provides an image showing the EdU fluorescence signal overlaid on a bright-field image of the selectively expanded T cells.

Example 8. Culturing and Export of T Lymphocytes on a Conditioned Microfluidic Surface Materials. CD3+ cells from AllCells Inc. and mixed with anti-CD3/anti-CD28 magnetic beads (DYNABEADS™, Thermofisher Scientific, Cat. No. 11453D) at a ratio of 1 bead/1 cell. The mixture was incubated in the same medium as the culturing experiment itself, for 5 hours in a 5% CO2 incubator at 37° C. Following the incubation, the T cell/bead mixture was resuspended for use.

Culture medium. RPMI-1640 (GIBCO®, ThermoFisher Scientific, Cat. No. 11875-127), 10% FBS, 2% Human AB serum (50 U/ml IL2; R&D Systems).

System and Microfluidic device. System and Microfluidic device: Manufactured by Berkeley Lights, Inc. The system included at least a flow controller, temperature controller, fluidic medium conditioning and pump component, light source for light activated DEP configurations, mounting stage for the microfluidic device, and a camera. The microfluidic device was an OptoFluidic™ device configured with Opto-Select™ technology. The microfluidic device included a microfluidic channel and a plurality of NanoPen™ chambers fluidically connected thereto, with the chambers having a volume of about $7 \times 10^5$ cubic microns. In addition, the microfluidic device had a covalently linked dextran conditioned surface Priming regime. 250 microliters of 100% carbon dioxide was flowed in at a rate of 12 microliters/sec. This was followed by 250 microliters of PBS containing 0.1% Pluronic® F27 (Life Technologies® Cat #P6866), flowed in at 12 microliters/sec. The final step of priming included 250 microliters of PBS, flowed in at 12 microliters/sec. Introduction of the culture medium follows.

Perfusion regime. The perfusion method was either of the following two methods:

1. Perfuse at 0.01 microliters/sec for 2 h; perfuse at 2 microliters/sec for 64 sec; and repeat.
2. Perfuse at 0.02 microliters/sec for 100 sec; stop flow 500 sec; perfuse at 2 microliters/sec for 64 sec; and repeat.

The T cell (plus bead) suspension was introduced into the microfluidic device by flowing the resuspension through a fluidic inlet and into the microfluidic channel. The flow was stopped and T cells/beads were randomly loaded into the NanoPen™ chambers by tilting the device and allowing gravity to pull the T cells/beads into the chambers.

Figure 12A:
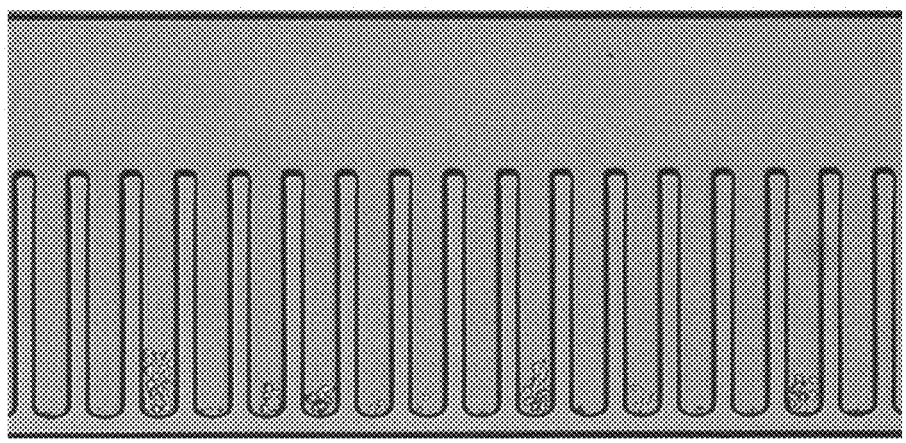
FIGS. 12A and 12B are photographic representations of an embodiment of culturing T cells in a microfluidic device having at least one conditioned surface.

After loading the T cells/beads into the NanoPen™ chambers, the culture medium was perfused through the microfluidic channel of the microfluidic device for a period of 4 days. FIG. 12A showed the growth of T cells on the dextran conditioned surface of the NanoPen™ chambers of the microfluidic device. The growth of T cells on the dextran conditioned surface was improved relative to a non-conditioned surface of a similar microfluidic device (data not shown).

Figure 12B:
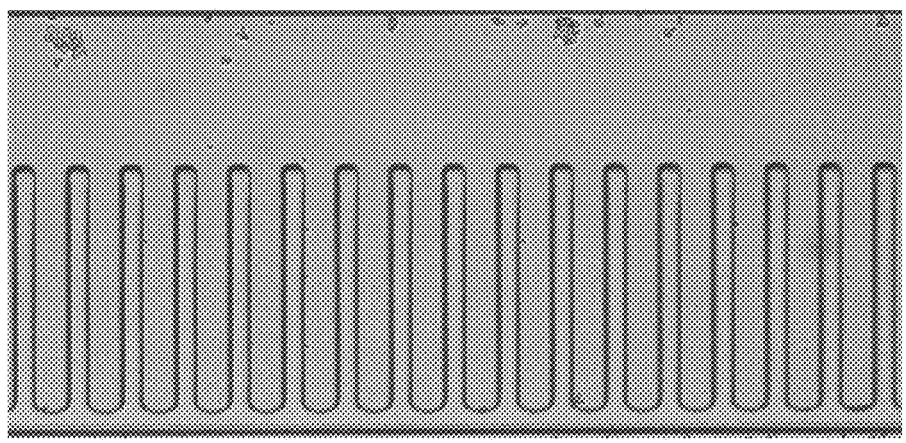

The T cells were then removed from the NanoPen™ chambers by gravity (e.g., tilting the microfluidic device). FIG. 12B shows the extent of removal from the growth chamber at the end of a twenty minute period, demonstrating excellent ability to export the expanded T cells into the flow channel, which was improved over that of removal of T cells from a non-conditioned surface of a similar microfluidic device. The T cells were then exported from the microfluidic device (not shown).

Example 9. Genetic Engineering of Human T Cells

Human T cells were genetically modified to remove functional PD-1 using the CRISPR/Cas9 technology. The genetic editing was accomplished according to the protocol of Schumann et al. (2015), Proc. Nat'l Acad. Sci. 112(33): 10437-442. Following the genetic editing, the resulting T cells were introduced into a OptoFluidic™ microfluidic device configured with Opto-Select™ technology (Berkeley Lights, Inc.). The microfluidic device included a microfluidic channel and a plurality of NanoPen™ chambers fluidically connected thereto. T cells were loaded into NanoPen™ chambers, after which T cells culture medium was perfused through the microfluidic channel to allow for T cell expansion. Following several days of culture, the T cells were observed to have expanded within the NanoPen™ chambers (see FIG. 13A). As shown in FIG. 13B, staining of the T cell populations with a fluorescently-labeled anti-PD-1 antibody revealed that most of the T cells growing in the microfluidic device lacked expression of PD-1 and therefore had been successfully modified.

The results of this experiment demonstrate that T cells can be genetically modified and subsequently expanded successfully within a microfluidic device.

Example 10. Method of Treating Melanoma with Genetically Engineered T Cells

Step 1: Obtain one or more melanoma tumor biopsies from a patient suffering from melanoma.

Step 2: Dissociate the tumor biopsy to obtain a mixture of single tumor-derived cells.

Step 3: Sort the tumor-derived cells by FACS or MACS selection using anti-CD8 and/or anti-CD4 antibodies to obtain an enriched population of tumor infiltrating T cells. (Alternatively, or in addition, a negative selection to remove non-lymphocytes can be employed.)

Step 4: Transfect the enriched population of tumor infiltrating T cells with an IL-2-encoding construct.
  Use CRISPR-Cas9 technology to target the IL-2-encoding construct to a pre-selected region of the genome.
  Optionally, the construct can include a tetracycline-inducible promoter.

Step 5: Label, select, and isolate T cells from the transfected cell population.
  Label the transfected cell population with fluorescently-labeled anti-CD4 and/or anti-CD8 antibodies. (Alternatively, fluorescently-labeled anti-CD3 antibodies can be used).
  Flow labeled cells into the flow channel of a Berkeley Lights™ microfluidic device and stop the flow.
  Select fluorescently-labeled cells and place them individually into isolation chambers in the Berkeley Lights™ microfluidic device.
  Resume the flow of fluid in the microfluidic device, thereby flowing any remaining, undesired cells out of the microfluidic device.

Step 6: Expand individual, isolated T cells into clonal populations on chip (i.e., within the microfluidic device).
  Incubate isolated T cells for 1-3 days on chip.
  Optionally, place one or more melanoma tumor cells (from the patient) into each isolation chamber that has an isolated T cells prior to incubation.
  Optionally, culture the T cells in the presence of rapamycin (to limit differentiation and/or exhaustion of T cells during culture, and/or maintain a subset of cells at the memory T cell stage of differentiation).

Step 7: For individual T cells that form clonal colonies, export 1-2 cells for genomic analysis
  Detect cells that carry a properly integrated construct (e.g., use genomic DNA sequence)
  Optionally, detect cells in which the IL-2 transgene construct is functionally active. For example, analyze cDNA for IL-2 expression. If inducible tetracycline promoter is used, TILs can be exposed to tetracycline prior to analysis of cDNA.
  Optionally, detect expression of T cell markers (e.g., using cDNA sequence)

Step 8: Export and pool desired T cell clones that carry a properly integrated, functionally active transgene construct.

Step 9: Inject the pooled T cell clones into the patient that provided the melanoma tumor biopsy.
  Inject $10^3$-$10^5$ genetically engineered T cells.

Step 10: Optionally, if tetracycline-inducible promoter is used, wait for genetically engineered T cells to reach melanoma tumors, then administer tetracycline to patient.

Example 11. Method of Treating Melanoma with Genetically Engineered Stem Memory T Cells (TSCMs)

Follow essentially the same protocol as Example 10, except:
  At Step 7: Identify T cell clones that express stem memory T cell markers.
  At Step 8: Pool TSCM clones that carry properly integrated, functionally active transgene constructs.
  At Step 9: Inject $10^3$-$10^4$ genetically engineered TSCMs into the patient that provided the melanoma tumor biopsy.

Example 12. Method of Treating Melanoma with Genetically Engineered T Effector Memory Cells (TEMs)

Follow essentially the same protocol as Example 10, except:
  At Step 7: Identify T cell clones that express T effector memory cell markers.
  At Step 8: Pool TEM clones that carry properly integrated, functionally active transgene constructs.
  At Step 9: Inject $10^4$-$10^5$ genetically engineered TEMs into the patient that provided the melanoma tumor biopsy.

Example 13. Method of Treating Melanoma with Genetically Engineered TSCMs and TEMs Follow essentially the same protocol as Example 10, except:
  At Step 7: Identify T cell clones that express stem memory T cell markers and T cell clones that express T effector memory cell markers.
  At Step 8: Pool TSCM and TEM clones that carry properly integrated, functionally active transgene constructs.
  At Step 9: Inject $10^4$-$10^5$ genetically engineered TSCM and TEM cells into the patient that provided the melanoma tumor biopsy.

Example 14. Method of Treating Melanoma with Genetically Engineered B Cells

Follow the same protocol as Example 10, except:
  At Step 2: Sort cells by FACS or MACS selection using anti-CD19 antibodies.
  At Step 5: Label the transfected cells with anti-CD20 antibodies.
  Alternatives to anti-CD20 antibodies at step 4 include antibodies to any of IgM, IgD, CD38, CD27, CD138, PNA, and GL7.
  At Step 6: Expand individual, isolated B cells on chip.
  At Step 7: Export 1-2 B cells for genomic analysis
  At Step 8: Export and pool desired plasma B cell clones that carry a properly integrated, functionally active transgene construct.
  At Step 9: Inject $10^4$-$10^5$ genetically engineered plasma B cells.

Example 15. Method of Treating Melanoma with Genetically Engineered TILs that Express an Anti-CTLA Antibody Follow essentially the same protocol as any one of Examples 10-14, except:
  At Step 4: Transfect the TILs with a construct that encodes an anti-CTLA-4 antibody.

Example 16. Method of Treating Melanoma with Genetically Engineered TILs that Express an Anti-CD3 Antibody Follow essentially the same protocol of any one of Examples 10-14, except:

At Step 4: Transfect the TILs with a construct that encodes an anti-CD3 antibody.

Example 17. Method of Treating Melanoma with Genetically Engineered TILs that Express a Bacterial Superantigen Follow essentially the same protocol of any one of Examples 10-14, except:
At Step 4: Transfect the TILs with a construct that encodes the SEA superantigen.

Example 18. Method of Treating Melanoma with Genetically Engineered TILs that Express a Pro-Inflammatory Polypeptide and a Matrix Degrading Enzyme Follow essentially the same protocol of any one of Examples 10-17, except:
At Step 4: Transfect the TILs with a construct that further encodes a heparanase enzyme.

PARTIAL LISTING OF THE EMBODIMENTS

1. An isolated tumor-infiltrating cell genetically engineered to provide increased expression of a pro-inflammatory protein other than a chimeric antigen receptor (CAR).

2. The isolated tumor-infiltrating cell of embodiment 1, genetically engineered for expression of an exogenous nucleic acid encoding a transcriptional activator that increases expression of the pro-inflammatory protein.

3. The isolated tumor-infiltrating cell of embodiment 1, genetically engineered for expression of an exogenous nucleic acid encoding the pro-inflammatory protein.

4. The isolated tumor-infiltrating cell of embodiment 2 or 3, further comprising a nucleic acid encoding a CAR.

5. The isolated tumor-infiltrating cell of any one of embodiments 1-4, wherein the tumor-infiltrating cell is derived from a cell isolated from a solid tumor biopsy.

6. The isolated tumor-infiltrating cell of any one of embodiments 1-4, wherein the tumor-infiltrating cell is derived from a cell isolated from peripheral blood or a lymphoid tissue.

7. The isolated tumor-infiltrating cell of any one of embodiments 1-6, wherein the cell is a leukocyte.

8. The isolated tumor-infiltrating cell of any one of embodiments 1-6, wherein the cell is a T cell, macrophage, or NK cell.

9. The isolated tumor-infiltrating cell of any one of embodiments 1-6, wherein the cell expresses at least one marker selected from the group consisting of CD3, CD4, CD8, T-bet, GATA-3, CD25, Foxp3, ROR-gammaT, CD38, and CD40.

10. The isolated tumor-infiltrating cell of any one of embodiments 1-6, wherein the cell expresses at least one marker selected from the group consisting of CD56, CD16, F480, siglec3, and gamma receptor.

11. The isolated tumor-infiltrating cell of embodiment 3, wherein the exogenous nucleic acid encodes a cytokine.

12. The isolated tumor-infiltrating cell of embodiment 11, wherein the cytokine is selected from the group consisting of IL-2, IL-7, IL-15, IFN (type 1 or 2), CSF, GM-CSF, TNF-alpha, and IL-21.

13. The isolated tumor-infiltrating cell of embodiment 3, wherein the exogenous nucleic acid encodes an antibody.

14. The isolated tumor-infiltrating cell of embodiment 13, wherein the antibody is selected from the group consisting of anti CTLA-4, anti-PD-1, and anti-PD-L1.

15. The isolated tumor-infiltrating cell of embodiment 3, wherein the exogenous nucleic acid encodes a chemokine.

16. The isolated tumor-infiltrating cell of embodiment 15, wherein the chemokine is selected from the group consisting of RANTES, IP-10, CXCL9, and CXCL10.

17. The isolated tumor-infiltrating cell of embodiment 3, wherein the exogenous nucleic acid encodes a microbial antigen.

18. The isolated tumor-infiltrating cell of embodiment 17, wherein the microbial antigen is selected from the group consisting of SEA, SEA/E-120, and a bacterial flagellar protein.

19. The isolated tumor-infiltrating cell of any one of embodiments 1-18, wherein the pro-inflammatory protein is expressed as a fusion protein.

20. The isolated tumor-infiltrating cell of any one of embodiments 2-19, wherein the exogenous nucleic acid is operably linked to an inducible promoter.

21. The isolated tumor-infiltrating cell of embodiment 20, wherein the inducible promoter is a tetracycline-inducible promoter.

22. The isolated tumor-infiltrating cell of any one of embodiments 1-21, further comprising a nucleic acid encoding a matrix degrading enzyme.

23. The isolating tumor-infiltrating cell of embodiment 22, wherein the matrix degrading enzyme is selected from the group consisting of heparinase, collagenase, a matrix metalloproteinase, and plasminogen activator.

24. The isolating tumor-infiltrating cell of embodiment 22, wherein the matrix degrading enzyme is MMP9 or urokinase.

25. A method of preparing a tumor-infiltrating cell, the method comprising: obtaining a sample from a patient; isolating tumor-infiltrating cells from the sample; and transforming the tumor-infiltrating cells with an exogenous nucleic acid encoding a pro-inflammatory polypeptide other than a chimeric antigen receptor (CAR) or a transcription factor that induces expression of the pro-inflammatory polypeptide.

26. The method of embodiment 25, wherein the sample comprises a tumor biopsy or a fine needle aspirate (FNA).

27. The method of embodiment 25, wherein the sample comprises peripheral blood or a lymphoid tissue biopsy.

28. The method of any one of embodiments 25-27, wherein the step of isolating tumor-infiltrating cells from the sample comprises dissociating the sample into single cells.

29. The method of any one of embodiments 25-28, wherein the tumor-infiltrating cells are tumor-infiltrating lymphocytes (TILs).

30. The method of embodiment 29, wherein the TILS are cytotoxic T cells or T helper cells.

31. The method of any one of embodiments 25-30, wherein the step of isolating the tumor-infiltrating cells comprises contacting the sample, or cells dissociated therefrom, with an agent that specifically binds to a cell type-specific cell surface marker.

32. The method of embodiment 31, wherein the agent is an anti-CD4 and/or anti-CD8 antibody.

33. The method of embodiment 31 or 32, wherein the agent is attached to a solid support.

34. The method of any one of embodiments 25-33, wherein the step of isolating tumor-infiltrating cells comprises performing FACS or MACS.

35. The method of any one of embodiments 25-34, further comprising: introducing the isolated tumor-infiltrating cells into a microfluidic device; and placing one or more isolated tumor-infiltrating cells into each of a plurality of isolation chambers located within the microfluidic device.

36. The method of embodiment 35, wherein the microfluidic device is a nanofluidic device.

37. The method of embodiment 35 or 36, wherein the step of placing the one or more isolated tumor-infiltrating cells into isolation chambers comprises using an electrokinetic force to move the cells into the plurality of isolation chambers.

38. The method of embodiment 37, wherein the electrokinetic force is a dielectrophoretic force.

39. The method of any one of embodiments 35 to 38, wherein the steps of introducing and placing the one or more isolated tumor-infiltration cells are performed after the step of transforming the tumor-infiltrating cells.

40. The method of any one of embodiments 25-39, wherein the step of transforming the tumor-infiltrating cells comprises transforming the cells with a viral vector.

41. The method of embodiment 40, wherein the viral vector is a lentiviral vector.

42. The method of any one of embodiments 25-39, wherein the step of transforming the tumor-infiltrating cells comprises introducing CRISPR-Cas9, a TALEN, or a zinc finger protein into the cells.

43. The method of any one of embodiments 35-42, further comprising culturing the transformed cells within the isolation chambers of the microfluidic device.

44. The method of embodiment 43, wherein the transformed cells are cultured individually in separate isolation chambers to thereby produce clonal populations of transformed cells.

45. The method of any one of embodiments 25-44, further comprising culturing the transformed cells in the presence of rapamycin.

46. The method of any one of embodiments 25-45, further comprising administering a transformed cell to a patient.

47. The method of embodiment 46, wherein the patient receiving the transformed cell is the same patient from whom the sample was obtained.

48. A method of treating a patient having a cancer, the method comprising administering to the patient an effective regime of a genetically engineered tumor-infiltrating cell of any one of embodiments 1-24.

49. The method of embodiment 48, wherein the cancer is a melanoma, a breast cancer, a genitourinary cancer, a cancer of the nervous system, an intestinal cancer, or a lung cancer.

50. The method of embodiment 48 or 49, wherein the genetically engineered tumor-infiltrating cells comprise an exogenous nucleic acid operably linked to an inducible promoter, and wherein the method further comprises administering to the patient an agent capable of inducing expression of the exogenous nucleic acid.

51. The method of embodiment 50, wherein the exogenous nucleic acid comprises a tetracycline-inducible promoter and the agent administered to the patient is tetracycline.

52. The method of any one of embodiments 48-51, wherein at least $10^3$ genetically engineered tumor-infiltrating cells are administered to the patient.

53. The method of any one of embodiments 48-51, wherein $10^3$-$10^5$ genetically engineered tumor-infiltrating cells are administered to the patient.

54. The method of embodiment 52 or 53, wherein the genetically engineered tumor-infiltrating cells administered to the patient comprise a mixture of genetically engineered tumor-infiltrating cell populations, each population clonally derived from a single genetically engineered tumor-infiltrating cell.

55. The method of embodiment 54, wherein at least 95% of the cells in the mixture are from one of the clonal populations of genetically engineered tumor-infiltrating cells.

56. A composition comprising a mixture of genetically engineered tumor-infiltrating cell populations, each population clonally derived from a single genetically engineered tumor-infiltrating cell of any one of embodiments 1-24.

57. The composition of embodiment 56, containing substantially no other cells than the cells from one of the clonal populations of genetically engineered tumor-infiltrating cells.

58. The composition of embodiment 56, wherein at least 95% of the cells in the mixture are from one of the clonal populations of genetically engineered tumor-infiltrating cells.

59. The composition of any one of embodiments 56-58, wherein the composition comprises at least $10^4$ cells.

60. The composition of any one of embodiments 56-59 further comprising a pharmaceutically acceptable carrier.

What is claimed is:

1. An isolated tumor-infiltrating cell genetically engineered to provide increased expression of a pro-inflammatory protein other than a chimeric antigen receptor (CAR), wherein the tumor-infiltrating cell is derived from a cell isolated from a solid tumor biopsy and 1s genetically engineered for expression of an exogenous nucleic acid encoding the pro-inflammatory protein; and wherein the tumor-infiltrating cell further comprises a nucleic acid encoding a matrix degrading enzyme, wherein the matrix degrading enzyme 1s chosen from a matrix metalloproteinase and plasminogen activator, wherein the cell is selected from a T cell or a natural killer (NK) cell, and wherein the pro-inflammatory protein encoded by the exogenous nucleic acid comprises
  a. an IL-21 cytokine;
  b. a chemokine chosen from RANTES, IP-10, CXCL9, and CXCL10; or
  c. a fusion protein comprising any of the foregoing cytokines and chemokines.

2. The isolated tumor-infiltrating cell of claim 1, further comprising a nucleic acid encoding a CAR.

3. The isolated tumor-infiltrating cell of claim 1, wherein the cell is a T cell or wherein the cell expresses at least one marker from CD3, CD4, and CD8.

4. A composition comprising a mixture of genetically engineered tumor-infiltrating cell populations, each population clonally derived from a single genetically engineered tumor-infiltrating cell of claim 1.

5. A composition comprising a mixture comprising clonal genetically engineered tumor-infiltrating cell populations, wherein at least 95% of the cells in the mixture are from one of the clonal populations, each clonal population being derived from a single genetically engineered tumor-infiltrating cell of claim 1.

6. The isolated tumor-infiltrating cell of claim 1, wherein the cell is a NK cell or wherein the cell expresses at least one marker chosen from CD56 and CD16.

7. A method of treating a patient having a cancer, the method comprising administering to the patient a genetically engineered tumor-infiltrating cell of claim 1.

8. The method of claim 7, wherein the cancer is a melanoma, a breast cancer, or a lung cancer.

9. The method of claim 7, wherein the genetically engineered tumor infiltrating cells comprises an exogenous nucleic acid operably linked to an inducible promoter, and wherein the method further comprises administering to the patient an agent capable of inducing expression of the exogenous nucleic acid, further wherein the exogenous nucleic acid comprises a tetracycline-inducible promoter and the agent administered to the patient is tetracycline.

* * * * *

UNITED STATES PATENT AND TRADEMARK OFFICE
CERTIFICATE OF CORRECTION

PATENT NO.         : 11,273,177 B2
APPLICATION NO.    : 15/488139
DATED              : March 15, 2022
INVENTOR(S)        : Kevin T. Chapman et al.

Page 1 of 1

It is certified that error appears in the above-identified patent and that said Letters Patent is hereby corrected as shown below:

In the Claims

Claim 1, Column 60, Line 32 should read:
--isolated from a solid tumor biopsy and is genetically--

Claim 1, Column 60, Line 37 should read:
--degrading enzyme is chosen from a matrix metallaproteinase--

Claim 9, Column 61, Line 4 should read:
--engineered tumor infiltrating cell comprises an exogenous--

Signed and Sealed this
Twenty-fourth Day of May, 2022

Katherine Kelly Vidal
*Director of the United States Patent and Trademark Office*